US010689454B2

United States Patent
Ellmark et al.

(10) Patent No.: US 10,689,454 B2
(45) Date of Patent: *Jun. 23, 2020

(54) ANTI-CD137 ANTIBODIES AND USES THEREOF

(71) Applicant: ALLIGATOR BIOSCIENCE AB, Lund (SE)

(72) Inventors: Peter Ellmark, Lund (SE); Sara Fritzell, Lund (SE); Christina Furebring, Lund (SE); Jessica Petersson, Lund (SE); Anna Sall, Lund (SE); Karin Enell Smith, Lund (SE); Laura Varas, Lund (SE); Laura Von Schantz, Lund (SE); Niina Veitonmaki, Lund (SE)

(73) Assignee: ALLIGATOR BIOSCIENCE AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,374

(22) Filed: Jul. 17, 2019

(65) Prior Publication Data

US 2019/0352414 A1 Nov. 21, 2019

Related U.S. Application Data

(63) Continuation of application No. 16/461,544, filed as application No. PCT/EP2017/079930 on Nov. 21, 2017.

(30) Foreign Application Priority Data

Nov. 21, 2016 (GB) .................................. 1619648.7

(51) Int. Cl.
| | | |
|---|---|---|
| *A61P 35/00* | (2006.01) | |
| *G01N 33/53* | (2006.01) | |
| *C07K 16/28* | (2006.01) | |
| *A61K 39/00* | (2006.01) | |

(52) U.S. Cl.
CPC .......... *C07K 16/2878* (2013.01); *A61P 35/00* (2018.01); *G01N 33/53* (2013.01); *A61K 2039/505* (2013.01); *C07K 2317/21* (2013.01); *C07K 2317/24* (2013.01); *C07K 2317/33* (2013.01); *C07K 2317/565* (2013.01); *C07K 2317/75* (2013.01); *C07K 2317/92* (2013.01); *G01N 2333/70596* (2013.01)

(58) Field of Classification Search
CPC ...... C07K 16/2878; A61P 35/00; G01N 33/53
USPC ................... 424/173.1; 530/388.1
See application file for complete search history.

(56) References Cited

U.S. PATENT DOCUMENTS

| 4,235,871 A | 11/1980 | Papahadjopoulos et al. |
| 4,816,567 A | 3/1989 | Cabilly et al. |
| 5,851,451 A | 12/1998 | Takechi et al. |

FOREIGN PATENT DOCUMENTS

| EP | 0213303 B1 | 3/1987 |
| WO | 2016/029073 A2 | 2/2016 |
| WO | 2016/134358 A1 | 8/2016 |
| WO | 2016/185016 A1 | 11/2016 |

OTHER PUBLICATIONS

Kohler, et al. "Continuous cultures of fused cells secreting antibody of predefined specificity" Nature (1975) 256:495-497.
Koide, et al. "Monobodies: Antibody Mimics Based on the Scaffold of the Fibronectin Type III Domain" Meth. Mol. Biol. (2007) 352:95-109.
Kozbor, et al. "Specific Immunoglobulin Production and Enhanced Tumorigenicity Following Ascites Growth of Human Hybridomas" J. Immunol. Methods (1985) 81:31-42.
Krause, et al. "Grafting of thrombopoietin-mimetic peptides into cystine knot miniproteins yields high-affinity thrombopoietin antagonists and agonists" FEBS J. (2007) 274:86-95.
Kwong, et al. "Localized immunotherapy via liposome-anchored Anti-CD137 + IL-2 prevents lethal toxicity and elicits local and systemic antitumour immunity" Cancer Res. (2013) 73:1547-1558.
Labrijn, et al. "Therapeutic IgG4 antibodies engage in Fab-arm exchange with endogenous human IgG4 in vivo" Nat. Biotechnol. (2009) 27(8):767-71.
Lazar, et al. "Engineered antibody Fc variants with enhanced effector function" Proc. Natl. Acad. Sci. (2006) 103 (11):4005-4010.
Lee, et al. "4-1BB promotes the survival of CD8+ T lymphocytes by increasing expression of Bcl-xL and Bfl-1" J. Immunol. (2002) 169:4882-4888.
Lee, et al. "4-1BB and OX40 dual costimulation synergistically stimulate primary specific CD8 T cells for robust effector function" J. Immunol. (2004) 173:3002-3012.
Li, et al. "Monocyte surface expression of Fcgamma receptor RI (CD64), a biomarker reflecting type-I interferon levels in systemic lupus erythematosus" Arthritis Res. Ther. (2010) 12(3):R90.
Li, et al. "Inhibitory Fcgamma receptor engagement drives adjuvant and anti-tumour activities of agonistic CD40 antibodies" Science (2011) 333:1030-1034.
Li, et al. "A Higher Frequency of CD14+ CD169+ MonocyteslMacrophages in Patients with Colorectal Cancer" PLoS One (2015) 10(10):e0141817.

(Continued)

*Primary Examiner* — Yan Xiao
(74) *Attorney, Agent, or Firm* — Robert C. Netter, Jr.; Dann, Dorfman, Herrell & Skillman

(57) ABSTRACT

The present invention relates to antibodies (and fragments, variants, fusions and derivatives thereof) with binding specificity for domain 2 of human CD137 which are capable of inhibiting the binding of a reference antibody to human CD137. The antibodies and fragments have utility in the treatment of diseases such as cancer. The invention also relates to pharmaceutical compositions, uses, methods and kits comprising such antibodies.

17 Claims, 13 Drawing Sheets

Specification includes a Sequence Listing.

(56) References Cited

OTHER PUBLICATIONS

Lu, et al. "Structure of FcγRI in complex with Fc reveals the importance of glycan recognition for high-affinity IgG binding" Proc. Natl. Acad. Sci. (2015) 112(3):833-8.
Marks, et al. "By-passing Immunization: Human Antibodies from V-gene Libraries Displayed on Phage" J. Mol. Biol. (1991) 222:581-597.
McMillin, et al. "Complete regression of large solid tumours using engineered drug-resistant hematopoietic cells and anti-CD137 immunotherapy" Hum. Gene Ther. (2006) 17:798-806.
Melero, et al. "Monoclonal antibodies against the 4-1BB T-cell activation molecule eradicate established tumours" Nat. Med. (1997) 3:682-685.
Melero, et al. "Agonist Antibodies to TNFR Molecules That Costimulate T and NK cells" Clin. Cancer Res. (2013) 19:1044-1053.
Melero, et al. "Clinical Development of Immunostimulatory Monoclonal Antibodies and Opportunities for Combination" Clin. Cancer Res. (2013) 19:997-1008.
Meziere, et al. "In Vivo T Helper Cell Response to Retro-Inverso Peptidomimetics" J. Immunol. (1997) 159:3230-3237.
Miller, et al. "4-1BB-specific monoclonal antibody promotes the generation of tumour-specific immune responses by direct activation of CD8 T cells in a CD40-dependent manner" J. Immunol. (2002) 169:1792-1800.
Morales-Kastresana, et al. "Combined immunostimulatory monoclonal antibodies extend survival in an aggressive transgenic hepatocellular carcinoma mouse model" Clin. Cancer Res. (2013) 19:6151-6162.
Morimura, et al. "Monocyte subpopulations in human gliomas: expression of Fc and complement receptors and correlation with tumor proliferation" Acta Neuropathol. (1990) 80(3):287-94.
Neuberger, et al., "Antibody Engineering" Proc. 8th Intl. Biotech. Symposium Part 2:792-799.
Niu, et al. "Cytokine-mediated disruption of lymphocyte trafficking, hemopoiesis, and induction of lymphopenia, anemia, and thrombocytopenia in anti-CD137-treated mice" J. Immunol. (2007) 178:4194-4213.
Norton, et al. "Gut macrophage phenotype is dependent on the tumor microenvironment in colorectal cancer" Clin. Transl. Immunology (2016) 5(4):e76.
Nygren, P.A. "Alternative binding proteins: Athbody binding proteins developed from a small three-helix bundle scaffold" FEBS J. (2008) 275:2668-2676.
Orlandi, et al. "Cloning immunoglobulin variable domains for expression by the polymerase chain reaction" Proc. Natl. Acad. Sci. (1989) 86:3833-3837.
Overdijk, et al. "Crosstalk between human IgG isotypes and murine effector cells" J. Immunol. (2012) 189(7):3430-8.
Palazon, et al. "The HIF-1a Hypoxia Response in Tumour-Infiltrating T Lymphocytes Induces Functional CD137 (4-1BB) for Immunotherapy" Cancer Discovery (2012) 2:608-623.
Palazon, et al. "Agonist anti-CD137 mAb act on tumour endothelial cells to enhance recruitment of activated T lymphocytes" Cancer Res. (2011) 71(3):801-11.
Pan, et al. "OX40 ligation enhances primary and memory cytotoxic T lymphocyte responses in an immunotherapy for hepatic colon metastases" Mol. Ther. (2002) 6:528-536.
Peipp, et al. "Antibody fucosylation differentially impacts cytotoxicity mediated by NK and PMN effector cells" Blood (2008) 112(6):2390-9.
Porembka, et al. "Pancreatic adenocarcinoma induces bone marrow mobilization of myeloid-derived suppressor cells which promote primary tumor growth" Cancer Immunol. Immunother. (2012) 61(9):1373-85.
Presta, L.G., "Antibody Engineering" Curr. Op. Struct. Biol. (1992) 2:593-596.
Pulle, et al. "IL-15-dependent induction of 4-1BB promotes antigen-independent CD8 memory T cell survival" J. Immunol. (2006) 176:2739-2748.
Rabu, et al. "Production of recombinant human trimeric CD137L (4-1BBL). Cross-linking is essential to its T cell co-stimulation activity" J. Biol. Chem. (2005) 280:41472-41481.
Raju, T.S. "Terminal sugars of Fc glycans influence antibody effector functions of IgGs" Curr. Opin. Immunol. (2008) 20(4):471-8.
Richards, et al. "Optimization of antibody binding to FcgRIIa enhances macrophage phagocytosis of tumor cells" Mol. Cancer Ther. (2008) 7(8):2517-27.
Riechmann, et al. "Reshaping human antibodies for therapy" Nature (1998) 332:323-329.
Roussel, et al. "Mass cytometry deep phenotyping of human mononuclear phagocytes and myeloid-derived suppressor cells from human blood and bone marrow" J. Leukoc. Biol. (2017) 102(2):437-447.
Ryan, et al. "Antibody targeting of B-cell maturation antigen on malignant plasma cells" Mol. Cancer Ther. (2007) 6:3009-3018.
Sallin, et al. "The anti-lymphoma activities of anti-CD137 monoclonal antibodies are enhanced in FcgammaRIII(−/−) mice" Cancer Immunol. Immunother. (2014) 63:947-958.
Sanmamed, et al. "Agonists of Co-stimulation in Cancer Immunotherapy Directed Against CD137, OX40, GITR, CD27, CD28, and ICOS" Semin. Oncol. (2015) 42:640-655.
Schlehuber, et al. "Lipocalins in drug discovery: from natural ligand-binding proteins to 'anticalins'" Drug Discovery Today (2005) 10:23-33.
Shields, et al. "High Resolution Mapping of the Binding Site on Human IgG1 for FcgRI, FcgRII, FcgRIII, and FcRn and Design of IgG1 Variants with Improved Binding to the FcgR" J. Biol. Chem. (2001) 276(9):6591-604.
Shuford, et al. "4-1BB costimulatory signals preferentially induce CD8+ T cell proliferation and lead to the amplification in vivo of cytotoxic T cell responses" J. Exp. Med. (1997) 186:47-55.
Silverman, et al. "Multivalent avimer proteins evolved by exon shuffling of a family of human receptor domains" Nat. Biotechnol. (2005) 23:1556-1561.
So, et al. "Immune regulation and control of regulatory T cells by OX40 and 4-1BB" Cytokine Growth Factor Rev. (2008) 19:253-262.
Solito, et al. "Myeloid-derived suppressor cell heterogeneity in human cancers" Ann. NY Acad. Sci. (2014) 1319:47-65.
St. Rose, et al. "CD134/CD137 dual costimulation-elicited IFN-gamma maximizes effector T-cell function but limits Treg expansion" Immunol. Cell Biol. (2013) 91:173-183.
Steurer, et al. "Ex Vivo Coating of Islet Cell Allografts with Murine CTLA4/Fc Promotes Graft Tolerance" J. Immunol. (1995) 155(3):1165-74.
Stewart, et al. "The role of Fc gamma receptors in the activity of immunomodulatory antibodies for cancer" J. Immunother. (2014) 2:29.
Strohl, W.R. "Optimization of Fc-mediated effector functions of monoclonal antibodies" Curr. Opin. Biotechnol. (2009) 20(6):685-91.
Sun, et al. "Co-stimulation agonists as a new immunotherapy for autoimmune diseases" Trends Mol. Med. (2003) 9 (11):483-9.
Taraban, et al. "Expression and costimulatory effects of the TNF receptor superfamily members CD134 (OX40) and CD137 (4-1BB), and their role in the generation of anti-tumour immune responses" Eur. J. Immunol. (2002) 32:3617-3627.
Uno, et al. "Eradication of established tumours in mice by a combination antibody-based therapy" Nat. Med. (2006) 12:693-698.
Vaccaro, et al. "Engineering the Fc region of immunoglobulin G to modulate in vivo antibody levels" Nat. Biotechnol. (2005) 23(10):1283-8.
Veber, et al. "Conformationally restricted bicyclic analogs of somatostatin" Proc. Natl. Acad. Sci. (1978) 75:2636.
Verhoeyen, et al. "Reshaping human antibodies: grafting an antilysozyme activity" Science (1988) 239:1534-1536.
Vidarsson, et al. "IgG subclasses and allotypes: from structure to effector functions" Front. Immunol. (2014) 5:520.
Vinay, et al. "Immunotherapy of cancer with 4-1BB" Mol. Cancer Ther. (2012) 11:1062-1070.

(56) References Cited

OTHER PUBLICATIONS

Wang, et al. "NK Cell-Mediated Antibody-Dependent Cellular Cytotoxicity in Cancer Immunotherapy" Front. Immunol. (2015) 6:368.
Wei, et al. "Combinatorial PD-1 blockade and CD137 activation has therapeutic efficacy in murine cancer models and synergizes with cisplatin" PLoS One (2013) 8:e84927.
Westwood, et al. "Three agonist antibodies in combination with high-dose IL-2 eradicate orthotopic kidney cancer in mice" J. Transl. Med. (2010) 8:42.
Westwood, et al. "Combination anti-CD137 and anti-CD40 antibody therapy in murine myc-driven hematological cancers" Leuk. Res. (2014) 38:948-954.
Westwood, et al. "Routes of delivery for CpG and anti-CD137 for the treatment of orthotopic kidney tumours in mice" PLoS One (2014) 9:e95847.
White, et al., "Interaction with FcγRIIB is critical for the agonistic activity of anti-CD40 monoclonal antibody" J. Immunol. (2011) 187:1754-1763.
White, et al., "Fcγ receptor dependency of agonistic CD40 antibody in lymphoma therapy can be overcome through antibody multimerization" J. Immunol. (2014) 193:1828-1835.
White, et al. "Conformation of the human immunoglobulin G2 hinge imparts superagonistic properties to immunostimulatory anticancer antibodies" Cancer Cell (2015) 27(1):138-48.
Wilcox, et al. "Provision of antigen and CD137 signaling breaks immunological ignorance, promoting regression of poorly immunogenic tumours" J. Clin. Invest. (2002) 109:651-659.
Wilson, et al. "An Fcgamma receptor dependent mechanism drives antibody-mediated target-receptor signaling in cancer cells" Cancer Cell (2011) 19:101-113.
Winter, et al. "Man-made antibodies" Nature (1991) 349:293-299.
Wyzgol, et al. "Trimer stabilization, oligomerization, and antibody-mediated cell surface immobilization improve the activity of soluble trimers of CD27L, CD40L, 41BBL, and glucocorticoid-induced TNF receptor ligand" J. Immunol. (2009)183:1851-1861.
Yamane-Ohnuki, et al. "Production of therapeutic antibodies with controlled fucosylation" MAbs (2009) 1(3):230-26.
Zhang, et al. "Targeted and untargeted CD137L fusion proteins for the immunotherapy of experimental solid tumours" Clin. Cancer Res. (2007) 13:2758-2767.
Zhang, et al. "Circulating and tumor-infiltrating myeloid-derived suppressor cells in patients with colorectal carcinoma" PLoS One (2013) 8(2):e57114.
Ryan, et al., "Enhancing the safety of antibody-based immunomodulatory cancer therapy without compromising therapeutic benefit: Can we have our cake and eat it too?" Expert Opinion on Biological Therapy (2016) 16(5):655-674.
Vinay, et al., "Therapeutic potential of anti-CD137 (4-1 BB) monoclonal antibodies" Expert Opinion on Therapeutic Targets (2016) 20(3):361-373.
Segal, et al., "Results from an Integrated Safety Analysis of Urelumab, an Agonist Anti-CD137 Monoclonal Antibody" Clin. Cancer Res. (2016) 23(8):1929-36.
Peters, et al., "Engineering an Improved IgG4 Molecule with Reduced Disulfide Bond Heterogeneity and Increased Fab Domain Thermal Stability" J. Biol. Chem. (2012) 287(29):24525-24533.
Bolanos-Mateo, et al., "Focusing and sustaining the antitumor CTL effector killer response by agonist anti-CD137 mAb" J. ImmunoTherapy Cancer (2014) 2(Suppl 3):P95.
Sanchez-Paulete, et al., "Deciphering CD137 (4-1BB) signaling in T-cell costimulation for translation into successful cancer immunotherapy" Eur. J. Immunol. (2016) 46:513-522.
Akhmetzyanova, et al., "CD137 Agonist Therapy Can Reprogram Regulatory T Cells into Cytotoxic CD4+ T Cells with Antitumour Activity" J. Immunol. (2016) 196:484-492.
Almeida, et al., "Comparative analysis of the morphological, cytochemical, immunophenotypical, and functional characteristics of normal human peripheral blood lineage(−)/CD16(+)/HLA-DR(+)/CD14(−/lo) cells, CD14(+) monocytes, and CD16(−) dendritic cells" Clin. Immunol. (2001) 100(3):325-38.
Angov, E., "Codon usage: Nature's roadmap to expression and folding of proteins" Biotechnol. J. (2011) 6:650-659.
Armour, et al., "Recombinant human IgG molecules lacking Fcgamma receptor I binding and monocyte triggering activities" Eur. J. Immunol. (1999) 29(8):2613-24.
Ascierto, et al., "Clinical experiences with anti-CD137 and anti-PD1 therapeutic antibodies" Semin. Oncol. (2010) 37:508-516.
Attucci, et al. "EPI-hNE4, a Proteolysis-Resistant Inhibitor of Human Neutrophil Elastase and Potential Anti-Inflammatory Drug for Treating Cystic Fibrosis" J. Pharmacol. Exp. Ther. (2006) 318:803-809.
Baessler, et al., "CD137 ligand mediates opposite effects in human and mouse NK cells and impairs NK-cell reactivity against human acute myeloid leukemia cells" Blood (2010) 115(15):3058-69.
Bartkowiak, et al. "4-1BB Agonists: Multi-Potent Potentiators of Tumour Immunity" Front. Oncol. (2015) 5:117.
Binz, et al., "High-affinity binders selected from designed ankyrin repeat protein libraries" Nat. Biotechnol. (2004) 22:575-582.
Boerner, et al., "Production of Antigen-Specific Human Monoclonal Antibodies From in Vitro-Primed Human Splenocytes" J. Immunol. (1991) 147:86-95.
Borghouts, et al., "Peptide aptamers: Recent developments for cancer therapy" Expert Opin. Biol. Ther. (2005) 5 (6):783-797.
Bronte, et al., "Recommendations for myeloid-derived suppressor cell nomenclature and characterization standards" Nat. Commun. (2016) 7:12150.
Bruhns, et al., "Specificity and affinity of human Fcgamma receptors and their polymorphic variants for human IgG subclasses" Blood (2009) 113(16):3716-25.
Bulliard, et al., "OX40 engagement depletes intratumoural Tregs via activating FcγRs, leading to antitumour efficacy" Immunol. Cell Biol. (2014) 92(6):475-80.
Cavnar, et al., "KIT oncogene inhibition drives intratumoral macrophage M2 polarization" J. Exp. Med. (2013) 210 (13):2873-86.
Cheeseman, et al., "Expression Profile of Human Fc Receptors in Mucosal Tissue: Implications for Antibody-Dependent Cellular Effector Functions Targeting HIV-1 Transmission" PLoS One (2016) 11(5):e0154656.
Cole, et al., "Human monoclonal antibodies" Mol. Cell. Biol. (1984) 62:109-120.
Cote, et al., "Generation of human monoclonal antibodies reactive with cellular antigens" Proc. Natl. Acad. Sci. (1983) 80:2026-2030.
Curran, et al., "Combination CTLA-4 blockade and 4-1BB activation enhances tumour rejection by increasing T-cell infiltration, proliferation, and cytokine production" PLoS One (2011) 6:e19499.
Dubrot, et al., "Treatment with anti-CD137 mAbs causes intense accumulations of liver T cells without selective antitumour immunotherapeutic effects in this organ" Cancer Immunol. Immunother. (2010) 59:1223-1233.
Elliott, et al., "Human Tumor-Infiltrating Myeloid Cells: Phenotypic and Functional Diversity" Front Immunol. (2017) 8:86.
Eruslanov, et al. "Circulating and tumor-infiltrating myeloid cell subsets in patients with bladder cancer" Int. J. Cancer (2012) 130(5):1109-19.
Eruslanov, et al. "Tumor-associated neutrophils stimulate T cell responses in early-stage human lung cancer" J. Clin. Invest (2014) 124(12):5466-80.
Gauttier, et al., "Agonistic anti-CD137 antibody treatment leads to antitumour response in mice with liver cancer" Int. J. Cancer (2014) 135:2857-2867.
Gebauer, et al., "Engineered protein scaffolds as next-generation antibody therapeutics" Curr. Opin. Chem. Biol. (2009) 13(3):245-255.
Gray, et al., "Optimising anti-tumour CD8 T-cell responses using combinations of immunomodulatory antibodies" Eur. J. Immunol. (2008) 38:2499-2511.
Griesinger, et al., "Characterization of distinct immunophenotypes across pediatric brain tumor types" J. Immunol. (2013) 191(9):4880-8.

(56) References Cited

OTHER PUBLICATIONS

Grugan, et al. "Tumor-associated macrophages promote invasion while retaining Fc-dependent anti-tumor function" J. Immunol. (2012) 189(11):5457-66.

Guilliams, et al. "The function of Fcγ receptors in dendritic cells and macrophages" Nat. Rev. Immunol. (2014) 14 (2):94-108.

Guo, et al. "Combined TIM-3 blockade and CD137 activation affords the long-term protection in a murine model of ovarian cancer" J. Transl. Med. (2013) 11:215.

Hansen, et al. "Tumour-associated macrophages are related to progression in patients with metastatic melanoma following interleukin-2 based immunotherapy" Acta Oncol. (2006) 45(4):400-5.

Hey, et al., "Artificial, non-antibody binding proteins for pharmaceutical and industrial applications" Trends Biotechnol. (2005) 23:514-522.

Hinton, et al. "Engineered Human IgG Antibodies with Longer Serum Half-lives in Primates" J. Biol. Chem. (2004) 279(8):6213-6.

Hogarth, et al. "Fc receptor-targeted therapies for the treatment of inflammation, cancer and beyond" Nat. Rev. Drug Discov. (2012) 11(4):311-31.

Kohrt, et al. "Targeting CD137 enhances the efficacy of cetuximab" J. Clin. Invest. (2014) 124(6):2668-2682.

Hoogenboom, et al. "By-passing Immunisation: Human Antibodies from Synthetic Repertoires of Germline VH Gene Segments Rearranged in Vitro" J. Mol. Biol. (1991) 227:381-388.

Horton, et al. "Fc-engineered anti-CD40 antibody enhances multiple effector functions and exhibits potent in vitro and in vivo antitumor activity against hematological malignancies" Blood (2010) 116(16):3004-3012.

Hruz, et al."Genevestigator v3: a reference expression database for the meta-analysis of transcriptomes" Adv. Bioinformatics (2008) 2008:420747.

Hu, et al., "Tumor-associated macrophages in cancers" Clin. Transl. Oncol. (2016) 18(3):251-8.

Idusogie, et al. "Mapping of the C1q Binding Site on Rituxan, a Chimeric Antibody with a Human IgG1 Fc" J. Immunol. (2000) 164(8):4178-84.

Iida, et al. "Two mechanisms of the enhanced antibody-dependent cellular cytotoxicity (ADCC) efficacy of non-fucosylated therapeutic antibodies in human blood" BMC Cancer (2009) 9:58.

Jefferis, R. "Glycosylation as a strategy to improve antibody-based therapeutics" Nat. Rev. Drug Discov. (2009) 8 (3)226-34.

Jones, et al., "Replacing the complementarity determining regions in a human antibody with those from a mouse" Nature (1986) 321:522-525.

Kim, et al. "Divergent effects of 4-1BB antibodies on antitumour immunity and on tumour-reactive T-cell generation" Cancer Res. (2001) 61:2031-2037.

FIGURE 2

| Gene ID | Domain: 1　　2　　3　　4<br>Module:　　A ∣ B ∣ A ∣ B ∣ A ∣ B<br>Signal peptide |
|---|---|
| 1550 | |
| 1551 | |
| 1552 | |
| 1553 | |
| 1554 | |
| 1555 | |

ANTI-CD137 ANTIBODIES AND USES THEREOF

This application is a continuation application of U.S. patent application Ser. No. 16/461,544, filed May 16, 2019, which is a § 371 application of PCT/EP2017/079930, filed Nov. 21, 2017, which in turn claims priority to GB Application No. 1619648.7, filed Nov. 21, 2016. The entire disclosure of each of the foregoing applications is incorporated by reference herein.

Incorporated herein by reference in its entirety is the Sequence Listing being concurrently submitted via EFS-Web as a text file named SeqList.txt, created Jul. 17, 2019, and having a size of 36,236 bytes.

FIELD OF INVENTION

The present invention relates to antibody-based polypeptides with binding specificity for CD137, which have utility in the treatment of diseases such as cancer. The invention also relates to pharmaceutical compositions, uses, methods and kits comprising such antibodies.

BACKGROUND

CD137 (4-1BB, TNFRSF9) is a TNF receptor (TNFR) superfamily member and is expressed on activated $CD4^+$ and $CD8^+$ T cells, Treg, DC, monocytes, mast cells and eosinophils. CD137 activation plays an important role in $CD8^+$ T cell activation and survival (Lee et al., 2002; Pulle et al., 2006). It sustains and augments, rather than initiates, effector functions and preferentially supports Th1 cytokine production (Shuford et al., 1997). In $CD4^+$ T cells, CD137 stimulation initially results in activation and later in activation-induced cell death, explaining why CD137 agonistic antibodies have shown therapeutic effect in tumour immunity as well as in autoimmunity (Zhang, J C I, 2007, Sun, Trends Mol Med, 2003). CD137 also suppresses Treg function (So, Cytokine Growth Factor Rev, 2008). Activation of CD137 is dependent on receptor oligomerization (Rabu et al., 2005; Wyzgol et al., 2009).

CD137 agonistic antibody has been shown to activate endothelial cells in the tumour environment, leading to upregulation of ICAM-1 and VCAM-1 and improved T cell recruitment (Palazon, Cancer Res, 2011).

CD137 is upregulated on NK cells activated by cytokines or CD16, in mice or humans, respectively (see Melero, CCR 19 (5)1044-53, 2013 and references cited therein). CD137 has been shown to activate NK cells in mice as well as humans, potentiating ADCC (Kohrt et al., 2014), though there are reports suggesting opposite effects on NK cells in mice and humans, leading to NK cell activation in mice and inhibition in humans (Baessler, Blood, 2010).

Several studies have demonstrated induction of tumour immunity by treatment with agonistic CD137 antibody (Dubrot et al., 2010; Gauttier et al., 2014; Kim et al., 2001; McMillin et al., 2006; Melero et al., 1997; Miller et al., 2002; Sallin et al., 2014; Taraban et al., 2002; Uno et al., 2006; Vinay and Kwon, 2012; Wilcox et al., 2002). In addition, it synergizes with several immunomodulators, including CpG, TRAIL, CD40, OX-40, DR5, PD-1/PD-L1, CTLA-4 Tim-3, IL-2, IL-12 (Curran et al., 2011; Gray et al., 2008; Guo et al., 2013; Kwong et al., 2013; Lee et al., 2004; Morales-Kastresana et al., 2013; Pan et al., 2002; St Rose et al., 2013; Uno et al., 2006; Wei et al., 2013; Westwood et al., 2010; Westwood et al., 2014a; Westwood et al., 2014b) in pre-clinical models.

Two CD137 antibodies are in clinical development. Urelumab (BMS-66513) is a fully human IgG4 antibody developed by Bristol-Myers Squibb. Several phase I and II studies in various indications are currently ongoing. The other CD137 antibody in development is PF-05082566, a fully human IgG2 antibody developed by Pfizer. It is currently in phase I development in lymphoma and various solid cancers.

The agonistic effect of CD137 antibodies is affected by the isotype of the Fc region. The antibodies tested in the clinic are either IgG2 or IgG4. Like most TNFR family members, CD137 depends on cross linking for activation (Wilson 2011, Cancer Cell). The CD137L expressed on the membrane of an APC may induce significant multiple cross linking of the receptor. An antibody can by itself only cross link two CD137 receptors, and to induce a strong signal, further cross linking via FcγRs expressed on other cells (in trans) may be necessary for induction of a strong CD137 mediated signal. An exception to this may be IgG2 antibodies, which induce a cross linking independent signaling by an unknown mechanism (White et al, 2015 Cancer Cell). T cells do not express FcγRs, and the FcγR mediated cross linking in vivo is thought to be mediated by monocytes, macrophages, DCs and potentially B cells and other cell types. It has been suggested that interaction with the inhibitory FcγR FcγRIIB plays a major role for this effect in mouse models for CD40 agonists (Li 2011, Science), whereas for OX40 antibodies, interactions with activating receptors may be of greater importance (Bulliard 2014, Imm and Cell Biol). For CD137 antibodies, FcγRII is not critical (Sanmamed 2015, Semin Onc). The translational relevance of this is uncertain, since the human FcγR distribution as well as the affinity of different IgG isotypes to different FcγR differs from mice. Further, human IgG1 binds to mFcγRIIb with relatively low affinity, similar to mIgGIIa and considerably lower than mIgG1, the latter having the most potent effect in vivo (Li Science 2011, Overdijk 2012 JI, Horton et al 2008, White et al 2011 and 2014).

Another factor to take into account is that engagement of FcγR receptors may also induce ADCC, antibody-dependent cellular phagocytosis (ADCP) and complement-dependent cytotoxicity (CDC) on cells coated with antibodies (for simplicity ADCC below includes ADCP and CDC). Typically, human IgG1 is a strong inducer of NK/Macrophage dependent ADCC, depending on the nature of the target, the cell type and the receptor density. IgG4 antibodies may also induce ADCC but to a lower extent than IgG1 (Wang 2015, Front Imm; Vidarson 2014 Front Imm).

The effect of a CD137 agonistic antibody with different isotypes may thus be affected by the balance between 1) inducing cross linking, which results in a stronger immune activation, and 2) inducing ADCC, which may lead to killing of both effector T cells (predominantly CD8 T cells) and Tregs. The net effect of 1) and 2) will likely depend on the distribution of CD137 expressing cells, the possibility of the target cells to engage with FcγR expressing immune cells, the receptor density and affinity and the sensitivity of Teff vs Treg to ADCC. The CD137 expression is high both on CD8 and Tregs in melanoma tumours (Quezada, presentation SITC 2015). The IgG4 format would allow for FcγRI mediated cross linking by macrophages and monocytes, yet minimizing NK mediated ADCC of effector CD8 T cells.

However, as outlined above, it is difficult to translate comparison of different human Fc in mouse models due to differences in expression and affinity between murine and human FcRs. Further, the functional consequence in vivo of antibodies blocking the binding of the CD137L to CD137 is currently debated.

Several studies have demonstrated induction of tumour immunity by treatment with agonistic CD137 mAb (Dubrot et al., 2010; Gauttier et al., 2014; Kim et al., 2001; McMillin et al., 2006; Melero et al., 1997; Miller et al., 2002; Sallin et al., 2014; Taraban et al., 2002; Uno et al., 2006; Vinay and Kwon, 2012; Wilcox et al., 2002). Two different antibodies are commonly used for in vivo studies in mice, Lob12.3 and 3H3 (Shuford 1997 J Exp Med).

The toxicity seen in mouse models has been detected following repeated dosing in a time dependent but not dose dependent manner (Ascierto 2010 Semin Onc, Dubrot 2010 Can Imm, Niu 2007 JI). The toxicity includes skin toxicity and liver toxicity: aspartate amino transferase/alanine amino transferase ratio (ASAT/ALAT) and cytokine release. This suggests that either the toxicity requires CD137 mediated pre-activation of immune cell populations (likely T cells) or it depends on secondary effects caused by antidrug-antibodies (ADA) response, potentially forming aggregations of CD137 antibodies that may lead to enhanced cross-linking. The toxicities seen in mice are reversible and seems to depend on TNFa/CD8 cell dependent manner (Ascierto 2010 Sem Onc). Toxicology studies in monkeys showed that both single and repeated dosing of up to 100 mg/kg once weekly for four weeks was tolerable with no skin or liver toxicity detected (Ascierto 2010, Semin Onc).

Prolonged and continuous activation through TNF receptor family members may lead to immune exhaustion. Therefore, it may be of advantage to administer such antibodies in a manner allowing resting periods for the cells expressing the receptors. One approach to increase the resting period in a specific dosing protocol is to reduce the half-life of an antibody by for example decreasing the binding to the neonatal Fc receptor (FcRn). This could, depending on the administration route, also reduce the toxicity associated with the treatment.

There remains a need for improved anti-tumour therapies, particularly anti-CD137 antibodies suitable for clinical use and with improved properties, such as reduced toxicity.

SUMMARY OF INVENTION

A first aspect of the invention provides an antibody or an antigen-binding fragment thereof ('antibody polypeptides') with binding specificity for domain 2 of CD137, wherein the antibody or antigen-binding fragment is a CD137 agonist and is capable of inhibiting the binding of reference antibody '1630/1631' to human CD137.

A second aspect of the invention, provides an antibody or an antigen-binding fragment thereof ('antibody polypeptides') with binding specificity for domain 2 of CD137, wherein the antibody or antigen-binding fragment is a CD137 agonist and is capable of inhibiting the binding of reference antibody '2674/2675' to human CD137.

In one embodiment of the above aspects of the invention, the antibody or antigen binding fragment is capable of inhibiting the binding of reference antibody '1630/1631' and/or '2674/2675' to human CD137.

According to the first aspect of the invention, antibody polypeptides are provided which are capable of inhibiting the binding of one or more reference antibodies to human CD137.

For the avoidance of doubt, the following disclosures are applicable to both the first and second aspect of the invention.

By "CD137" we specifically include the human CD137 protein, for example as described in GenBank Accession No. AAH06196.1 (the sequence of which is set out in SEQ ID NO: 11, below). CD137 is also known in the scientific literature as 4-1BB and TNFRSF9.

Human CD137, amino acid sequence: >gi|571321| gb|AAA53133.1| 4-1BB [Homo sapiens]

[SEQ ID NO: 11]
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL

By "domain 2" corresponds to amino acids 66 to 107 of human CD137 (see bold, underlined region in SEQ ID NO:11 above).

Thus, the antibody polypeptides of the invention have specificity for CD137. By "specificity" we mean that the antibody polypeptide is capable of binding to CD137 in vivo, i.e. under the physiological conditions in which CD137 exists within the human body. Preferably, the antibody polypeptide does not bind to any other protein in vivo. Such binding specificity may be determined by methods well known in the art, such as ELISA, immunohistochemistry, immunoprecipitation, Western blots and flow cytometry using transfected cells expressing CD137.

The antibody preferably binds to human CD137 with a Kd value which is less than $10 \times 10^{-9}$M or less than $7 \times 10^{-9}$M, more preferably less than 4, or $2 \times 10^{-9}$M, most preferably less than $1.2 \times 10^{-9}$M. Advantageously, the antibody polypeptide is capable of binding selectively to CD137, i.e. it bind at least 10-fold more strongly to CD137 than to any other proteins. The anti-CD137 antibody preferably specifically binds to CD137, i.e. it binds to CD137 but does not bind, or binds at a lower affinity, to other molecules. Therefore, typically, the Kd for the antibody with respect to human CD137 will be 2-fold, preferably 5-fold, more preferably 10-fold less than Kd with respect to the other, non-target molecule, such as murine CD137, other TNFR superfamily members, or any other unrelated material or accompanying material in the environment. More preferably, the Kd will be 50-fold less, even more preferably 100-fold less, and yet more preferably 200-fold less.

Methods for measuring the overall affinity (KD) and on-rate (ka) and off-rate (kd) of an interaction (such as an interaction between an antibody and a ligand) are well known in the art. Exemplary in vitro methods are described in the accompanying Examples. It is also conceivable to use flow cytometry based methods (Sklar et al., Annu Rev Biophys Biomol Struct, (31), 97-119, 2002).

The term CD137 as used herein typically refers to human CD137. The antibody may have some binding affinity for CD137 from other mammals, such as CD137 from a non-human primate, for example *Macaca fascicularis* (cynomolgus monkey). The antibody preferably does not bind to murine CD137 and/or does not bind to other human TNFR superfamily members, for example human OX40 or CD40.

Typically, the invention provides an antibody or antigen-binding fragment with affinity for CD137 in its native state, and in particular for CD137 localised on the surface of a cell.

By "localised on the surface of a cell" it is meant that CD137 is associated with the cell such that one or more region of CD137 is present on the outer face of the cell surface. For example, CD137 may be inserted into the cell plasma membrane (i.e. orientated as a transmembrane protein) with one or more regions presented on the extracellular surface. This may occur in the course of expression of CD137 by the cell. Thus, in one embodiment, "localised on the surface of a cell" may mean "expressed on the surface of a cell." Alternatively, CD137 may be outside the cell with covalent and/or ionic interactions localising it to a specific region or regions of the cell surface.

The antibodies and antigen-binding fragments thereof as defined herein are CD137 agonists. For example, they may be capable of inducing the release of interferon-gamma from CD8+ T cells. Agonistic activity of anti-CD137 antibodies may be evaluated in a T cell assay based on primary CD8+ T cells (see Examples).

Thus, the antibody may modulate the activity of a cell expressing CD137, wherein said modulation is an increase or decrease in the activity of said cell. The cell is typically a T cell. The antibody may increase the activity of a CD4+ or CD8+ effector cell, or may decrease the activity of, or deplete, a regulatory T cell (T reg). In either case, the net effect of the antibody will be an increase in the activity of effector T cells, particularly CD4+, CD8+ or NK effector T cells. Methods for determining a change in the activity of effector T cells are well known and are as described earlier.

The antibody preferably causes an increase in activity in a CD8+ T cell in vitro, optionally wherein said increase in activity is an increase in proliferation, IFN-γ production and/or IL-2 production by the T cell. The increase is preferably at least 2-fold, more preferably at least 10-fold and even more preferably at least 25-fold higher than the change in activity caused by an isotype control antibody measured in the same assay.

As outlined above, antibody polypeptides which are capable of inhibiting the binding of one or more reference antibodies to human CD137 are provided. The reference antibodies described herein are reference antibody 1630/1631 and reference antibody 2674/2675.

By reference antibody "1630/1631" we mean an intact IgG antibody comprising heavy and light chains having the amino acid sequences of SEQ ID NOS: 17 and 18, respectively.

1630/1631 - Full sequence Heavy chain
[SEQ ID NO: 17]
EVQLLESGGGLVQPGGSLRLSCAASGFTFGYSYMSWVRQAPGKGLEWVSS

IGSGSSYTYYADSVKGRFTISRDNSKNTLYLQMNSLRAEDTAVYYCARVY

SSPGIDYWGQGTLVTVSSASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK

1630/1631 - Full sequence Light chain
[SEQ ID NO: 18]
DIQMTQSPSSLSASVGDRVTITCRASQSISSYLNWYQQKPGKAPKLLIYA

ASSLQSGVPSRFSGSGSGTDFTLTISSLQPEDFATYYCQQYYTWVPFTFG

QGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

By reference antibody "2674/2675" we mean an intact IgG antibody comprising heavy and light chains having the amino acid sequences of SEQ ID NOS: 29 and 30, respectively.

2674/2675 - Full sequence heavy chain
[SEQ ID NO: 29]
EVQLLESGGGLVQPGGSLRLSCAASGFNFGYSYMSWVRQAPGKGLEWVSS

IGSTSSHTYYADSVKGRFTISRDNSKNTLYLQMNSLRAEDTAVYYCARVY

SSPGIDYWGQGTLVTVSSASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK

2674/2675 - Full sequence light chain
[SEQ ID NO: 30]
DIQMTQSPSSLSASVGDRVTITCRASQSIGSTLNWYQQKPGKAPKLLIYG

ASSLQSGVPSRFSGSGSGTDFTLTISSLQPEDFATYYCQQYYTWVPFTFG

QGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

As discussed below, the reference antibody '1630/1631' binds to domain 2 of CD137. Reference antibody 2674/2675 also binds to domain 2 of CD137. Thus, it will be appreciated that the antibody or an antigen-binding fragment of the invention also binds to domain 2 of CD137.

By "capable of inhibiting the binding of reference antibody '1630/1631' to human CD137" we mean that the presence of the antibody polypeptides of the invention inhibits, in whole or in part, the binding of '1630/1631' to human CD137. Similarly, by "capable of inhibiting the binding of reference antibody '2674/2675' to human CD137" we mean that the presence of the antibody polypeptides of the invention inhibits, in whole or in part, the binding of '2674/2675' to human CD137. Such competitive binding inhibition can be determined using assays and methods well known in the art, for example using BIAcore chips with immobilised CD137 and incubating with the reference antibody '1630/1631' or '2674/2675' with and without an antibody polypeptide to be tested. Alternatively, a pair-wise mapping approach can be used, in which the reference antibody '1630/1631' or '2674/2675' is immobilised to the surface of the BIAcore chip, CD137 antigen is bound to the immobilised antibody, and then a second antibody is tested for simultaneous CD137-binding ability (see 'BIAcore Assay Handbook', GE Healthcare Life Sciences, 29-0194-00 AA 05/2012; the disclosures of which are incorporated herein by reference).

In a further alternative, competitive binding inhibition can be determined using flow cytometry. For example, to test whether a test antibody is able to inhibit the binding of the 1630/1631 or 2674/2675 reference antibody to a cell surface antigen, cells expressing the antigen can be pre-incubated with the test antibody for 20 min before cells are washed and incubated with the reference 1630/1631 or 2674/2675 antibody conjugated to a fluorophore, which can be detected by flow cytometry. If the pre-incubation with the test antibody reduces the detection of the reference 1630/1631 or 2674/2675 antibody in flow cytometry, the test antibody inhibits the binding of the reference antibody to the cell surface antigen. If the antibody to be tested exhibits high affinity for CD137, then a reduced pre-incubation period may be used (or even no pre-incubation at all).

In a further alternative, competitive binding inhibition can be determined using an ELISA (e.g. as described in Example 8).

By "an antibody or an antigen-binding fragment thereof" we include substantially intact antibody molecules, as well as chimaeric antibodies, humanised antibodies, isolated human antibodies, single chain antibodies, bispecific antibodies, antibody heavy chains, antibody light chains, homodimers and heterodimers of antibody heavy and/or light chains, and antigen-binding fragments and derivatives of the same. Suitable antigen-binding fragments and derivatives include, but are not necessarily limited to, Fv fragments (e.g. single chain Fv and disulphide-bonded Fv), Fab-like fragments (e.g. Fab fragments, Fab' fragments and F(ab)$_2$ fragments), single variable domains (e.g. V$_H$ and V$_L$ domains) and domain antibodies (dAbs, including single and dual formats [i.e. dAb-linker-dAb]). The potential advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

For example, the antigen-binding fragment may comprise an scFv molecule, i.e. wherein the V$_H$ and V$_L$ partner domains are linked via a flexible oligopeptide.

The phrase "an antibody or an antigen-binding fragment thereof" is also intended to encompass antibody mimics (for example, non-antibody scaffold structures that have a high degree of stability yet allow variability to be introduced at certain positions). Those skilled in the art of biochemistry will be familiar with many such molecules, as discussed in Gebauer & Skerra, 2009, *Curr Opin Chem Biol* 13(3): 245-255 (the disclosures of which are incorporated herein by reference). Exemplary antibody mimics include: affibodies (also called Trinectins; Nygren, 2008, *FEBS J*, 275, 2668-2676); CTLDs (also called Tetranectins; *Innovations Pharmac. Technol.* (2006), 27-30); adnectins (also called monobodies; *Meth. Mol. Biol.*, 352 (2007), 95-109); anticalins (Drug Discovery Today (2005), 10, 23-33); DARPins (ankyrins; *Nat. Biotechnol.* (2004), 22, 575-582); avimers (*Nat. Biotechnol.* (2005), 23, 1556-1561); microbodies (*FEBS J*, (2007), 274, 86-95); peptide aptamers (*Expert. Opin. Biol. Ther.* (2005), 5, 783-797); Kunitz domains (*J. Pharmacol. Exp. Ther.* (2006) 318, 803-809); affilins (*Trends. Biotechnol.* (2005), 23, 514-522); affimers (Avacta Life Sciences, Wetherby, UK).

Persons skilled in the art will further appreciate that the invention also encompasses modified versions of antibodies and antigen-binding fragments thereof, whether existing now or in the future, e.g. modified by the covalent attachment of polyethylene glycol or another suitable polymer (see below).

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299, the disclosures of which are incorporated herein by reference) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120, the disclosures of which are incorporated herein by reference).

Suitable methods for the production of monoclonal antibodies are also disclosed in "*Monoclonal Antibodies: A manual of techniques*", H Zola (CRC Press, 1988, the disclosures of which are incorporated herein by reference) and in "*Monoclonal Hybridoma Antibodies: Techniques and Applications*", J G R Hurrell (CRC Press, 1982, the disclosures of which are incorporated herein by reference).

Likewise, antibody fragments can be obtained using methods well known in the art (see, for example, Harlow & Lane, 1988, "*Antibodies: A Laboratory Manual*", Cold Spring Harbor Laboratory, New York, the disclosures of which are incorporated herein by reference). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

The antibodies of the invention are defined by reference to the variable regions of reference antibodies 1630/1631 and 2674/2675.

The reference antibody designated '1630/1631' comprises:
(a) a heavy chain variable region having the amino acid sequence of SEQ ID NO: 1:

[SEQ ID NO: 1]
EVQLLESGGGLVQPGGSLRLSCAASGFTFGYSYMSWVRQAPGKGLEWVSS

IGSGSSYTYYADSVKGRFTISRDNSKNTLYLQMNSLRAEDTAVYYCARVY

SSPGIDYWGQGTLVTVSS and
(b) a light chain variable region having the amino acid sequence of SEQ ID NO: 2:

[SEQ ID NO: 2]
DIQMTQSPSSLSASVGDRVTITCRASQSISSYLNWYQQKPGKAPKLLIYA

ASSLQSGVPSRFSGSGSGTDFTLTISSLQPEDFATYYCQQYYTWVPFTFG

QGTKLEIK

The reference antibody designated '2674/2675' comprises:
(a) a heavy chain variable region having the amino acid sequence of SEQ ID NO: 19:

[SEQ ID NO: 19]
EVQLLESGGGLVQPGGSLRLSCAASGFNFGYSYMSWVRQAPGKGLEWVSS

IGSTSSHTYYADSVKGRFTISRDNSKNTLYLQMNSLRAEDTAVYYCARVY

SSPGIDYWGQGTLVTVSS and
(b) a light chain variable region having the amino acid sequence of SEQ ID NO: 20:

[SEQ ID NO: 20]
DIQMTQSPSSLSASVGDRVTITCRASQSIGSTLNWYQQKPGKAPKLLIYG

ASSLQSGVPSRFSGSGSGTDFTLTISSLQPEDFATYYCQQYYTWVPFTFG

QGTKLEIK

The term "amino acid" as used herein includes the standard twenty genetically-encoded amino acids and their corresponding stereoisomers in the 'D' form (as compared to the natural 'L' form), omega-amino acids and other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as "alanine" or "Ala" or "A", the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the antibody polypeptides as defined herein comprise or consist of L-amino acids.

It will be appreciated by persons skilled in the art that the binding specificity of an antibody or antigen-binding fragment thereof is conferred by the presence of complementarity determining regions (CDRs) within the variable regions of the constituent heavy and light chains, such as those CDRs described herein.

It will be further appreciated by persons skilled in the art that any intact IgG antibody comprising the above variable regions may be used as the reference antibody to identify antibody polypeptides of the invention that competitively inhibit 1630/1631 or 2674/2675 binding to CD137. Preferably however, reference antibody 1630/1631 consists of heavy and light chains as defined in SEQ ID NOs:17 and 18, respectively, and reference antibody 2674/2675 consists of heavy and light chains as defined in SEQ ID NOs:29 and 30, respectively Competitive binding typically arises because the test antibody binds at, or at least very close to, the epitope on the antigen to which binds the reference antibody (in this case, 1630/1631 or 2674/2675). However, it will be appreciated by persons skilled in the art that competitive binding may also arise by virtue of steric interference; thus, the test antibody may bind at an epitope different from that to which the reference antibody binds but may still be of sufficient size or configuration to hinder the binding of the reference antibody to the antigen.

The antibodies and antigen-binding fragments of the present invention were identified after screening of anti-CD137 antibodies, on the basis of exhibiting properties that make them particularly suitable as diagnostic and therapeutic agents for cancer.

Thus, in one embodiment, the antibody or antigen-binding fragment exhibits one or more of the following properties:
a) the ability to stimulate CD137 and activate T cells and other immune cells via a cross-linking dependent mechanism (e.g. to induce release of interferon-gamma from CD8+ T cells; see Examples); and/or
b) cross-reactivity with cynomolgus CD137 (see Examples).

For example, the antibody or antigen-binding fragment may exhibit both of the above properties.

As described above, the antibodies of the invention may have a cross linking dependent mechanism. By "cross linking dependent mechanism", we include an Fc cross linking dependent mechanism wherein the antibody has to bind both CD137 and an Fc receptor in order to stimulate CD137. As such, the antibody has to be capable of binding both CD137 and an Fc receptor.

In a preferred embodiment, the Fc receptor that is targeted is an FcγR. Examples of FcγRs include, FcγRI, FcγRIIA and FcγRIIB Thus, in one embodiment, the FcγR may be FcγRIIA. By FcγRIIA, we include both the R131 and H131 allotypes of FcγRIIA. Thus, in one embodiment, the FcγR to be targeted is the R131 allotype of FcγRIIA.

In an alternative embodiment, the antibody could be Fc crosslinking independent, such that it can stimulate CD137 in the absence of binding to an Fc receptor.

Thus, exemplary antibodies 2674/2675 and 1630/1631 are FcγR-crosslinking dependent agonistic antibodies targeting the co-stimulatory CD137 receptor. They are therefore only active in tissues or tumours containing cells expressing CD137 and FcγR. By "tumours containing cells expressing CD137 and FcγR" we include tumours or tumour draining lymph nodes comprising tumour cells and/or tumour infiltrating immune cells (such as monocytes, macrophages, dendritic cells, NK cells, T cells, B cells and granulocytes) expressing CD137 and FcγR. It will be appreciated that CD137 and FcγR may be expressed on separate cells within the tumour and/or co-expressed in the same cells. Reference antibodies 2674/2675 and 1630/1631 will thus provide a tumour directed immune activation in indications associated with cells that express both CD137 and FcγR in the tumour micro environment; this contrasts with FcγR independent CD137 agonists (e.g. Urelumab), which capable of inducing systemic immune activation. The tumour localizing effect of antibodies 2674/2675 and 1630/1631 will primarily depend on the number of tumour infiltrating macrophages/myeloid cells expressing different FcγRs.

It is known that IgG4 binds with high affinity to FcγRI and with moderate/low affinity to FcγRIIa and FcγRIIb. FcγRI and FcγRIIa are expressed on monocytes and FcγRIIb is expressed with a high density on B cells. Crosslinking of antibodies 2674/2675 and 1630/1631 will preferentially occur intratumorally as well as in adjacent draining lymph nodes. Systemically in the blood, where serum IgG levels are high, the availability of free non-blocked FcγRs are believed to be too low for an effective crosslinking to occur. Therefore, the risk for a systemic immune activation of is believed to be low which improves the risk-benefit profile compared to other CD137 mAbs.

Patient selection and a biomarker rationale for treatment with antibodies of the invention, such as 2674/2675 and 1630/1631, may be guided by tumour types that have infiltrating cells expressing CD137 and FcγRs. Thus, the antibodies of the invention may be for use in patients selected on the basis of having a tumour containing cells expressing CD137 and FcγRs (i.e. a as companion diagnostic test).

By "infiltrating cells" we include tumour infiltrating immune cells such as monocytes, macrophages, dendritic cells, NK cells, T cells, B cells and granulocytes Advantageously, the antibody or antigen-binding fragment is capable of inducing tumour immunity. Tumour immunity can be demonstrated using methods well known in the art, for example by re-challenging mice that have been cured from a given tumour by CD317 antibody treatment with the same tumour. If tumour immunity has been induced by the antibody therapy, then the tumour is rejected upon re-challenge.

In one embodiment, the antibody or antigen binding fragment substantially incapable of inducing the following upon binding to cells expressing CD137:
 a) antibody-dependent cellular cytotoxicity (ADCC);
 b) antibody-dependent cellular phagocytosis (ADCP); and/or
 c) complement-dependent cytotoxicity (CDC).

In one embodiment, the antibody or antigen-binding fragment is capable of binding to an epitope on the extracellular domain of CD137 which overlaps, at least in part, with the epitope on CD137 to which reference antibody 1630/1631 and/or 2674/2675 is capable of binding. Thus, the antibody or antigen-binding fragment may be capable of binding to an epitope located at/within domain 2 of CD137.

In one embodiment, the antibody polypeptide of the invention comprises or consists of an intact antibody (such as an IgG1 or IgG4 antibody). In a preferred embodiment, the antibody is an IgG4 antibody.

In an alternative embodiment, the antibody polypeptide of the invention comprises or consists of an antigen-binding fragment selected from the group consisting of Fv fragments (e.g. single chain Fv and disulphide-bonded Fv), Fab-like fragments (e.g. Fab fragments, Fab' fragments and F(ab)$_2$ fragments) and domain antibodies (e.g. single $V_H$ variable domains or $V_L$ variable domains). In particular, the antibody polypeptide may be a scFv.

In a further embodiment, as discussed above, the polypeptide of the invention comprises or consists of an antibody mimic selected from the group comprising or consisting of affibodies, tetranectins (CTLDs), adnectins (monobodies), anticalins, DARPins (ankyrins), avimers, iMabs, microbodies, peptide aptamers, Kunitz domains and affilins.

In one embodiment, the antibody or antigen binding fragment thereof according to the first or second aspect of the invention comprises:
 a) a heavy chain CDR1 sequence with the consensus sequence G, F, T/N, F, G, Y, S, Y;
 b) a heavy chain CDR2 sequence with the consensus sequence I, G, S, G/T, S, S, Y/H, T; and
 c) a heavy chain CDR3 sequence with the sequence ARVYSSPGIDY.

In one embodiment, the antibody or antigen binding fragment thereof comprises:
 a) a light chain CDR1 sequence with the consensus sequence Q, S, I, S/G, S, Y/T;
 b) a light chain CDR2 sequence with the consensus sequence A/G, A, S; and
 c) a light chain CDR3 sequence with the sequence QQYYTWVPFT.

In a preferred embodiment, the antibody or antigen-binding fragment thereof according to the first aspect of the invention comprises a heavy chain variable region comprising the following CDRs:
 a) GFTFGYSY [SEQ ID NO: 3] or an amino acid sequence containing up to 3 amino acid mutations compared to SEQ ID NO: 3, for example 1, 2 or 3 mutations;
 b) IGSGSSYT [SEQ ID NO: 4] or an amino acid sequence containing up to 3 amino acid mutations compared to SEQ ID NO: 4, for example 1, 2 or 3 mutations; and
 c) ARVYSSPGIDY [SEQ ID NO: 5] or an amino acid sequence containing up to 3 amino acid mutations compared to SEQ ID NO: 5, for example 1, 2 or 3 mutations.

Thus, the antibody or antigen-binding fragment thereof may comprise a heavy chain variable region comprising the CDRs of SEQ ID NOs 3, 4 and 5.

For example, the antibody or antigen-binding fragment thereof may comprise a heavy chain variable region having the amino acid sequence of the corresponding region of the 1630/1631 reference antibody, i.e. SEQ ID NO:1.

In an alternative preferred embodiment, the antibody or antigen-binding fragment thereof according to the first or second aspect of the invention comprises a heavy chain variable region comprising the following CDRs:
 a) GFNFGYSY [SEQ ID NO: 21] or an amino acid sequence containing up to 3 amino acid mutations compared to SEQ ID NO: 21, for example 1, 2 or 3 mutations;
 b) IGSTSSHT [SEQ ID NO: 22] or an amino acid sequence containing up to 3 amino acid mutations compared to SEQ ID NO: 22, for example 1, 2 or 3 mutations; and
 c) ARVYSSPGIDY [SEQ ID NO: 23] or an amino acid sequence containing up to 3 amino acid mutations compared to SEQ ID NO: 23, for example 1, 2 or 3 mutations.

Thus, the antibody or antigen-binding fragment thereof may comprise a heavy chain variable region comprising the CDRs of SEQ ID NOs 21, 22 and 23.

For example, the antibody or antigen-binding fragment thereof may comprise a heavy chain variable region having the amino acid sequence of the corresponding region of the 2674/2675 reference antibody, i.e. SEQ ID NO:19.

However, it will be appreciated (in relation to either embodiment, 1630/1631 or 2674/2675) that a low level of mutation (typically, just one, two or three amino acids) within a CDR sequence may be tolerated without loss of the specificity of the antibody or antigen-binding fragment for CD137.

For example, in an alternative embodiment, the antibody or antigen-binding fragment thereof may comprise a heavy chain variable region comprising the CDRs as defined above, wherein the H1 and H2 CDRs are mutated versions of SEQ ID NO: 3 and 4, respectively, and wherein the H3 CDR is SEQ ID NO: 5.

In a further alternative embodiment, the antibody or antigen-binding fragment thereof may comprise a heavy chain variable region comprising the CDRs as defined above, wherein the H1 and H2 CDRs are mutated versions of SEQ ID NO: 21 and 22, respectively, and wherein the H3 CDR is SEQ ID NO: 23.

Percent identity can be determined by, for example, the LALIGN program (Huang and Miller, *Adv. Appl. Math.* (1991) 12:337-357, the disclosures of which are incorporated herein by reference) at the Expasy facility site (http://www.ch.embnet.org/software/LALIGN_form.html) using as parameters the global alignment option, scoring matrix BLOSUM62, opening gap penalty −14, extending gap penalty −4. Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (as described in Thompson et al., 1994, *Nucl. Acid Res.* 22:4673-4680, which is incorporated herein by reference). The parameters used may be as follows:

Fast pair-wise alignment parameters: K-tuple (word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Alternatively, the BESTFIT program may be used to determine local sequence alignments.

In a further preferred embodiment, the antibody or antigen-binding fragment thereof according to the first aspect of the invention comprises a light chain variable region comprising the following CDRs:
a) QSISSY [SEQ ID NO: 6] or an amino acid sequence containing up to 3 amino acid mutations compared to SEQ ID NO: 6, for example 1, 2 or 3 mutations;
b) AAS [SEQ ID NO: 7] or an amino acid sequence containing up to 2 amino acid mutations compared to SEQ ID NO: 7; for example 1 or 2 mutations and
c) QQYYTWVPFT [SEQ ID NO: 8] or an amino acid sequence containing up to 3 amino acid mutations compared to SEQ ID NO: 8, for example 1, 2 or 3 mutations.

Thus, the antibody polypeptide may comprise a light chain variable region comprising the CDRs of SEQ ID NOs 6, 7 and 8.

For example, the antibody or antigen-binding fragment thereof may comprise a light chain variable region having the amino acid sequence of the corresponding region of the 1630/1631 reference antibody, i.e. SEQ ID NO: 2.

In an alternative embodiment, the antibody or antigen-binding fragment thereof may comprise a light chain variable region comprising the CDRs as defined above, wherein the L1 and L2 CDRs are mutated versions of SEQ ID NO: 6 and 7, respectively, and wherein the L3 CDR is SEQ ID NO:8.

In a further preferred embodiment, the antibody or antigen-binding fragment thereof according to the first or second aspect of the invention comprises a light chain variable region comprising the following CDRs:
a) QSIGST [SEQ ID NO: 24] or an amino acid sequence containing up to 3 amino acid mutations compared to SEQ ID NO: 24, for example 1, 2 or 3 mutations;
b) GAS [SEQ ID NO: 25] or an amino acid sequence containing up to 2 amino acid mutations compared to SEQ ID NO: 25; for example 1 or 2 mutations and
c) QQYYTWVPFT [SEQ ID NO: 26] or an amino acid sequence containing up to 3 amino acid mutations compared to SEQ ID NO: 26, for example 1, 2 or 3 mutations.

Thus, the antibody polypeptide may comprise a light chain variable region comprising the CDRs of SEQ ID NOs 24, 25 and 26.

For example, the antibody or antigen-binding fragment thereof may comprise a light chain variable region having the amino acid sequence of the corresponding region of the 1630/1631 reference antibody, i.e. SEQ ID NO: 20.

In an alternative embodiment, the antibody or antigen-binding fragment thereof may comprise a light chain variable region comprising the CDRs as defined above, wherein the L1 and L2 CDRs are mutated versions of SEQ ID NO: 24 and 25, respectively, and wherein the L3 CDR is SEQ ID NO: 26.

It will be appreciated by persons skilled in the art that for human therapy, human or humanised antibodies are preferably used. Humanised forms of non-human (e.g. murine) antibodies are genetically engineered chimaeric antibodies or antibody fragments having preferably minimal-portions derived from non-human antibodies. Humanised antibodies include antibodies in which complementary determining regions of a human antibody (recipient antibody) are replaced by residues from a complementary determining region of a non-human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596, the disclosures of which are incorporated herein by reference).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567, the disclosures of which are incorporated herein by reference) by substituting human complementarity determining regions with corresponding rodent complementarity determining regions. Accordingly, such humanised antibodies are chimeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies. Chimeric antibodies are discussed by Neuberger et al (1998, 8th *International Biotechnology Symposium* Part 2, 792-799).

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: *Monoclonal antibodies and Cancer*

*Therapy*, Alan R. Liss, pp. 77; Boerner et al., 1991. *J. Immunol.* 147:86-95, the disclosures of which are incorporated herein by reference).

It will be appreciated by persons skilled in the art that humanised antibodies or antigen-binding fragments of the invention may further comprise a heavy chain constant region, or part thereof (see below).

In one embodiment, the antibody polypeptide comprises a CH1, CH2 and/or CH3 region of an IgG heavy chain (such as an IgG1, IgG2, IgG3 or IgG4 heavy chain). Thus, the antibody polypeptide may comprise part or all of the constant regions from an IgG4 heavy chain. For example, the antibody polypeptide may be a Fab fragment comprising CH1 and CL constant regions, combined with any of the above-defined heavy and light variable regions respectively.

Likewise, the above-defined antibodies or antigen-binding fragments of the invention may further comprise a light chain constant region, or part thereof (see below). For example, the antibody polypeptide may comprise a CL region from a kappa or lambda light chain.

In one embodiment, the antibodies or antigen-binding fragments of the invention comprise an antibody Fc-region. It will be appreciated by a skilled person that the Fc portion may be from an IgG antibody, or from a different class of antibody (such as IgM, IgA, IgD or IgE). In one embodiment, the Fc region is from an IgG1, IgG2, IgG3 or IgG4 antibody. Advantageously, however, the Fc region is from an IgG4 antibody.

The Fc region may be naturally-occurring (e.g. part of an endogenously produced antibody) or may be artificial (e.g. comprising one or more point mutations relative to a naturally-occurring Fc region). A variant of an Fc region typically binds to Fc receptors, such as FcγR and/or neonatal Fc receptor (FcRn) with altered affinity providing for improved function and/or half-life of the polypeptide. The biological function and/or the half-life may be either increased or a decreased relative to the half-life of a polypeptide comprising a native Fc region. Examples of such biological functions which may be modulated by the presence of a variant Fc region include antibody dependent cell cytotoxicity (ADCC), antibody-dependent cellular phagocytosis (ADCP), complement-dependent cytotoxicity (CDC), and/or apoptosis.

Thus, the Fc region may be naturally-occurring (e.g. part of an endogenously produced human antibody) or may be artificial (e.g. comprising one or more point mutations relative to a naturally-occurring human Fc region).

As is well documented in the art, the Fc region of an antibody mediates its serum half-life and effector functions, such as complement-dependent cytotoxicity (CDC), antibody-dependent cellular cytotoxicity (ADCC) and antibody-dependent cell phagocytosis (ADCP).

Engineering the Fc region of a therapeutic monoclonal antibody or Fc fusion protein allows the generation of molecules that are better suited to the pharmacology activity required of them (Strohl, 2009, *Curr Opin Biotechnol* 20(6): 685-91, the disclosures of which are incorporated herein by reference).

(a) Engineered Fc Regions for Increased Half-Life

One approach to improve the efficacy of a therapeutic antibody is to increase its serum persistence, thereby allowing higher circulating levels, less frequent administration and reduced doses.

The half-life of an IgG depends on its pH-dependent binding to the neonatal receptor FcRn. FcRn, which is expressed on the surface of endothelial cells, binds the IgG in a pH-dependent manner and protects it from degradation.

Some antibodies that selectively bind the FcRn at pH 6.0, but not pH 7.4, exhibit a higher half-life in a variety of animal models.

Several mutations located at the interface between the CH2 and CH3 domains, such as T250Q/M428L (Hinton et al., 2004, *J Biol Chem.* 279(8):6213-6, the disclosures of which are incorporated herein by reference) and M252Y/S254T/T256E+H433K/N434F (Vaccaro et al., 2005, *Nat. Biotechnol.* 23(10):1283-8, the disclosures of which are incorporated herein by reference), have been shown to increase the binding affinity to FcRn and the half-life of IgG1 in vivo.

(b) Engineered Fc Regions for Altered Effector Function

Depending on the therapeutic antibody or Fc fusion protein application, it may be desired to either reduce or increase the effector function (such as ADCC).

For antibodies that target cell-surface molecules, especially those on immune cells, abrogating effector functions may be required for certain clinical indications.

The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions (Bruhns et al., 2009, *Blood.* 113(16):3716-25, the disclosures of which are incorporated herein by reference).

FcγRI Binding Affinity of IgG4 Vs IgG2

Bruhns et al performed a series of experiments that evaluated the specificity and affinity of the known human FcγRs, and their polymorphic variants, for the different human IgG subclasses (Bruhns et al., 2009, *Blood.* 113(16): 3716-25, the disclosures of which are incorporated herein by reference). In this study, it was clearly demonstrated that while IgG2 had no detectable affinity for FcγRI, IgG1, IgG3 and IgG4 all displayed a binding affinity for FcγRI in the nanomolar range (Bruhns et al., 2009, *Blood.* 113(16):3716-25, Lu et al., 2015, *Proc Natl Acad Sci USA.* 112(3):833-8, the disclosures of which are incorporated herein by reference). A summary of the relative binding affinities between the major human FcγRs and their variants and IgG isotypes is summarized in Table A. (Stewart et al. 2014, *J Immunother.* 2(29), the disclosures of which are incorporated herein by reference)

TABLE A

Binding affinity between human FcγRs and IgG isotypes.

| FcγR | IgG1 | IgG2 | IgG4 |
|---|---|---|---|
| FcγRI | ++++ | − | ++++ |
| FcγRIIA H131 | +++ | ++ | ++ |
| FcγRIIA R131 | +++ | + | ++ |
| FcγRIIB | ++ | − | ++ |
| FcγRIIIA V158 | +++ | + | ++ |
| FcγRIIIA F158 | ++ | − | ++ |

However, cellular activation influences the affinity of FcγRI for IgG immune complexes and the data generated by surface plasmon resonance in the Bruhns paper may not correctly reproduce what occurs at an inflammatory site. A review paper by Hogarth et al (Hogarth et al. 2012, *Nat Rev Drug Discov* 11(4):311-31, the disclosures of which are incorporated herein by reference) summarizes this as well as other studies focusing on FcγR binding for IgG.

FcγRI Expression on Myeloid Cell Subsets

Human FcγRs are primarily expressed by cells of the myeloid lineage, which has been demonstrated in numerous studies for circulating myeloid cell subsets. Classical monocytes, generally identified as CD14+ CD16− display high levels of FcγRII (CD32), intermediate levels of FcγRI and low levels of FcγRIII (CD16) (Almeida et al. 2001, 100(3): 325-38, Cheeseman et al. 2016, PLoS One 11(5):e0154656, the disclosures of which are incorporated herein by reference). CD14− CD16+ non-classical monocytes, however, display high levels of FcγRIII, intermediate levels of FcγRII and low levels of FcγRI (Almeida et al. 2001). A summary and compilation of several published microarray data sets showing the expression of human FcγR genes on different myeloid cell subsets confirms these observations (Guilliams et al. 2014, Nat Rev Immunol. 14(2):94-108, the disclosures of which are incorporated herein by reference).

Once within tissues, monocytes differentiate towards macrophages and, depending on environmental cues, these macrophages obtain specific phenotypes. In a study by Roussel et al (Roussel et al. 2017, J Leukoc Biol. 102(2): 437-447, the disclosures of which are incorporated herein by reference), peripheral blood monocytes were polarized towards different macrophage lineages by using various inflammatory stimuli and the expression profile of these cells evaluated. Here, IFN-γ stimulated monocytes resulted in a highly elevated expression specifically of CD64. A similar observation was made in SLE patients where increased CD64 expression was detected on circulating CD14+ monocytes, which correlated with expression of interferon-stimulated genes (Li et al. 2010, Arthritis Res Ther 12(3): R90, the disclosures of which are incorporated herein by reference).

Myeloid Cell Infiltration within Various Human Tumors

Various myeloid cell subsets such as inflammatory monocytes, monocytic myeloid-derived suppressor cells (MDSC) and macrophages have, in numerous studies, been shown to accumulate in cancer patients (Solito et al. 2014, Ann N Y Acad Sci 1319:47-65., Hu et al. 2016, Clin Transl Oncol. 18(3):251-8, the disclosures of which are incorporated herein by reference). Although recent attempts have aimed at proposing strategies to standardize the characterization of these cells (Bronte et al. 2016, Nat Commun. 7:12150, the disclosures of which are incorporated herein by reference), many phenotypic definitions of these cell populations can still be found throughout the literature (Elliott et al. 2017, Front Immunol. 8:86, the disclosures of which are incorporated herein by reference). Most commonly, these cells are defined by the expression of the markers CD11b, CD14, CD33 and the low expression of HLA-DR (monocytic MDSC) (Bronte et al. 2016). Additionally, tumor-associated macrophages (TAM) are commonly identified by the expression of CD64 and CD68 (M1-polarized, anti-tumorigenic), or CD163 and CD206 (M2-polarized, pro-tumorigenic) (Elliott et al. 2017).

A recent review by Elliott et al (referenced above) summarizes the numerous phenotypes used to identify myeloid cell subsets in cancer patients. Most of these studies have focused their analyses on circulating cells and increased frequencies of myeloid CD11b+ cells have been observed in the blood of patients with e.g. bladder, breast, colorectal, hepatocellular, pancreatic, prostate and renal cell carcinoma (Solito et al. 2014, Elliott et al. 2017). Other studies have also attempted to characterize the level of infiltration of these cells into tumor tissue. In colorectal tumors, a high frequency of CD14+ CD169+ cells was observed. These cells also expressed CD163 and CD206 and were thus suggested to be M2-polarized TAM (Li et al. 2015, PLoS One 10(10):e0141817, the disclosures of which are incorporated herein by reference). Another study in colorectal cancer patients also detected increased numbers of CD11 b+ CD33+ HLA-DR− cells, compared to healthy individuals (Zhang et al. 2013, PLoS One 8(2):e57114, the disclosures of which are incorporated herein by reference).

Similarly, CD11b+ myeloid cells were also identified in bladder tumors, where they accounted for 10-20% of all nucleated cells (Eruslanov et al. 2012, Int J Cancer 130(5): 1109-19, the disclosures of which are incorporated herein by reference). An even higher frequency of CD11b+ cells was observed in pancreatic cancer where over 60% of the CD45+ cells were CD11b+ CD15+ CD33+ (Porembka et al. 2012, Cancer Immunol Immunother 61(9):1373-85, the disclosures of which are incorporated herein by reference). Also, one study concluded that the major myeloid cell population within non-small cell lung carcinoma is a CD11b+ CD15+ CD66b+ neutrophil-like population. Interestingly, once these cells migrate from blood to the tumor tissue, these cells display an altered expression profile, including upregulated FcγRI (Eruslanov et al. 2014, *J Clin Invest.* 124(12):5466-80, the disclosures of which are incorporated herein by reference).

FcγRI Expression on Tumor-Infiltrating Cells

Although numerous studies have identified a high infiltration of myeloid cells within human tumors, no study has thoroughly explored the expression of FcγRs on these cells in detail. Several publications have, however, demonstrated the presence of FcγRI-expressing cells within tumor tissue.

A study by Morimura et al (Morimura et al. 1990, Acta Neuropathol. 80(3):287-94, the disclosures of which are incorporated herein by reference) evaluated gliomas from 12 human samples by immunocytochemistry and compared these to peritumoral control tissue. This study demonstrated a high presence of macrophages (using the marker CD163, RM3/1) in gliomas, compared to peritumoral tissue, as well as an increase in FcγRI and FcγRII (CD32). A more recent study by Griesinger et al (Griesinger et al. 2013, J Immunol. 191(9):4880-8, the disclosures of which are incorporated herein by reference) confirmed these observations by performing flow cytometric analyses of various pediatric brain tumor types. Here, a high frequency of CD45+ CD11b+ myeloid cells was observed for tissues from pilocytic astrocytoma and ependymoma patients. These cells also expressed high levels of FcγRI.

In addition to brain tumors, FcγRI expression has also been shown for other types of tumors. Grugan et al (Grugan et al. 2012, J Immunol. 189(11):5457-66, the disclosures of which are incorporated herein by reference) demonstrated the presence of CD11b+ CD14+ cells within human breast tumor tissue. These cells were shown to express high levels of FcγRI and FcγRIIa, as well as FcγRIIb and FcγRIII. Also, CD45+ CD11b+ CD14+ CD68+ TAM were identified in gastrointestinal stromal tumors displaying expression of FcγRI (Cavnar et al. 2013, J Exp Med. 210(13):2873-86, the disclosures of which are incorporated herein by reference). CD45+ CD11b+ FcγRI+ cells were also identified in colorectal cancer patients and these cells displayed a higher expression of FcγRI in tumor tissue, compared to healthy control tissue (Norton et al. 2016, Clin Transl Immunology. 5(4): e76, the disclosures of which are incorporated herein by reference). FcγRI expression has also been demonstrated for melanoma metastases (Hansen et al. 2006, Acta Oncol 45(4):400-5, the disclosures of which are incorporated herein by reference).

Binding of IgG to the FcγRs or C1q depends on residues located in the hinge region and the CH2 domain. Two regions of the CH2 domain are critical for FcγRs and C1q binding, and have unique sequences in IgG2 and IgG4. Substitutions into human IgG1 of IgG2 residues at positions 233-236 and IgG4 residues at positions 327, 330 and 331 were shown to greatly reduce ADCC and CDC (Armour et al., 1999, *Eur J Immunol.* 29(8):2613-24; Shields et al., 2001, *J Bio Chem.* 276(9):6591-604, the disclosures of which are incorporated herein by reference). Furthermore, Idusogie et al. demonstrated that alanine substitution at different positions, including K322, significantly reduced complement activation (Idusogie et al., 2000, *J Immunol.* 164(8):4178-84, the disclosures of which are incorporated herein by reference). Similarly, mutations in the CH2 domain of murine IgG2A were shown to reduce the binding to FcγRI, and C1q (Steurer. et al., 1995. *J Immunol.* 155(3): 1165-74, the disclosures of which are incorporated herein by reference).

Numerous mutations have been made in the CH2 domain of human IgG1 and their effect on ADCC and CDC tested in vitro (see references cited above). Notably, alanine substitution at position 333 was reported to increase both ADCC and CDC (Shields et al., 2001, supra; Steurer et al., 1995, supra). Lazar et al. described a triple mutant (S239D/I332E/A330L) with a higher affinity for FcγRIIIa and a lower affinity for FcγRIIb resulting in enhanced ADCC (Lazar et al., 2006, *PNAS* 103(11):4005-4010, the disclosures of which are incorporated herein by reference). The same mutations were used to generate an antibody with increased ADCC (Ryan et al., 2007, *Mol. Cancer Ther.* 6:3009-3018, the disclosures of which are incorporated herein by reference). Richards et al. studied a slightly different triple mutant (S239D/I332E/G236A) with improved FcγRIIIa affinity and FcγRIIa/FcγRIIb ratio that mediates enhanced phagocytosis of target cells by macrophages (Richards et al., 2008. *Mol Cancer Ther.* 7(8):2517-27, the disclosures of which are incorporated herein by reference).

Due to their lack of effector functions, IgG4 antibodies represent a preferred IgG subclass for receptor modulation without cell depletion. IgG4 molecules can exchange half-molecules in a dynamic process termed Fab-arm exchange. This phenomenon can also occur in vivo between therapeutic antibodies and endogenous IgG4.

The S228P mutation has been shown to prevent this recombination process allowing the design of less unpredictable therapeutic IgG4 antibodies (Labrijn et al., 2009, *Nat Biotechnol.* 27(8):767-71, the disclosures of which are incorporated herein by reference).

In a further embodiment, the effector function of the Fc region may be altered through modification of the carbohydrate moieties within the CH2 domain therein, for example by modifying the relative levels of fucose, galactose, bisecting N-acetylglucosamine and/or sialic acid during production (see Jefferis, 2009, *Nat Rev Drug Discov.* 8(3):226-34 and Raju, 2008, *Curr Opin Immunol.*, 20(4):471-8; the disclosures of which are incorporated herein by reference)

Thus, it is known that therapeutic antibodies lacking or low in fucose residues in the Fc region may exhibit enhanced ADCC activity in humans (for example, see Peipp et al., 2008, *Blood* 112(6):2390-9, Yamane-Ohnuki & Satoh, 2009, MAbs 1(3):230-26, Iida et al., 2009, BMC Cancer 9; 58 (the disclosures of which are incorporated herein by reference). Low fucose antibody polypeptides may be produced by expression in cells cultured in a medium containing an inhibitor of mannosidase, such as kinfunensine (see Example I below).

Other methods to modify glycosylation of an antibody into a low fucose format include the use of the bacterial enzyme GDP-6-deoxy-D-lyxo-4-hexulose reductase in cells not able to metabolise rhamnose (e.g. using the GlymaxX® technology of ProBioGen AG, Berlin, Germany).

Another method to create low fucose antibodies is by inhibition or depletion of alpha-(1,6)-fucosyltransferase in the antibody-producing cells (e.g. using the Potelligent® CHOK1SV technology of Lonza Ltd, Basel, Switzerland).

An exemplary heavy chain constant region amino acid sequence which may be combined with any VH region sequence disclosed herein (to form a complete heavy chain) is the IgG1 heavy chain constant region sequence reproduced here:

[SEQ ID NO: 12]
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Other heavy chain constant region sequences are known in the art and could also be combined with any VH region disclosed herein. For example, as indicated above, a preferred constant region is a modified IgG4 constant region such as that reproduced here:

[SEQ ID NO: 13]
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

This modified IgG4 sequence results in stabilization of the core hinge of IgG4 making the IgG4 more stable, preventing Fab arm exchange.

Another preferred constant region is a modified IgG4 constant region such as that reproduced here:

[SEQ ID NO: 14]
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNRYTQKSLSLSLGK

This modified IgG4 sequence exhibits reduced FcRn binding and hence results in a reduced serum half-life relative to wild type IgG4. In addition, it exhibits stabilization of the core hinge of IgG4 making the IgG4 more stable, preventing Fab arm exchange.

Also suitable for use in the polypeptides of the invention is a wild type IgG4 constant region such as that reproduced here:

[SEQ ID NO: 15]
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

An exemplary light chain constant region amino acid sequence which may be combined with any VL region sequence disclosed herein (to form a complete light chain) is the kappa chain constant region sequence reproduced here:

[SEQ ID NO: 16]
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Other light chain constant region sequences are known in the art and could also be combined with any VL region disclosed herein.

In an exemplary embodiment of the invention, the antibody polypeptide may comprise the IgG4 constant regions of SEQ ID NOs: 13 and 16, respectively.

Thus, exemplary antibody polypeptides of the invention comprise:
(a) a heavy chain comprising a variable region of SEQ ID NO: 1 together with a constant region of SEQ ID NO: 13; and
(b) a light chain comprising a variable region of SEQ ID NO: 2 together with a constant region of SEQ ID NO:16.

For example, the antibody polypeptides may be an intact IgG4 molecule comprising or consisting of two heavy chains having an amino acid sequence of SEQ ID NO: 17 and two light chains having an amino acid sequence of SEQ ID NO: 18.

Alternative exemplary polypeptides of the invention comprise:
(a) a heavy chain comprising a variable region of SEQ ID NO: 19 together with a constant region of SEQ ID NO: 13; and
(b) a light chain comprising a variable region of SEQ ID NO: 20 together with a constant region of SEQ ID NO:16.

For example, the antibody polypeptides may be an intact IgG4 molecule comprising or consisting of two heavy chains having an amino acid sequence of SEQ ID NO: 29 and two light chains having an amino acid sequence of SEQ ID NO: 30.

In one embodiment of the first or second aspect of the invention, the antibody polypeptide of the invention is or comprises a "fusion" polypeptide.

In addition to being fused to a moiety in order to improve pharmacokinetic properties, it will be appreciated that the polypeptide of the invention may also be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag, such as His6, or to an epitope recognised by an antibody such as the well-known Myc tag epitope. Fusions to any variant or derivative of said polypeptide are also included in the scope of the invention. It will be appreciated that fusions (or variants, derivatives or fusions thereof) which retain or improve desirable properties, such as IL-1R binding properties or in vivo half-life are preferred.

Thus, the fusion may comprise an amino acid sequence as detailed above together with a further portion which confers a desirable feature on the said polypeptide of the invention; for example, the portion may useful in detecting or isolating the polypeptide, or promoting cellular uptake of the polypeptide. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art or may be a lipophilic molecule or polypeptide domain that is capable of promoting cellular uptake of the polypeptide, as known to those skilled in the art.

It will be appreciated by persons skilled in the art that the antibody polypeptides of the invention may comprise or consist of one or more amino acids which have been modified or derivatised.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. The term 'peptidomimetic' refers to a compound that mimics the conformation and desirable features of a particular peptide as a therapeutic agent.

For example, the said polypeptide includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237, which is incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the said polypeptide may be a peptidomimetic compound wherein one or more of the amino acid residues are linked by a -y($CH_2NH$)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will also be appreciated that the said polypeptide may conveniently be blocked at its N- or C-terminus so as to help reduce susceptibility to exo-proteolytic digestion.

A variety of un-coded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166, which are incorporated herein by reference.

Typically, the antibody polypeptide of the invention will be a 'naked' antibody polypeptide, i.e. without any additional functional moieties such as cytotoxic or detectable moieties. For example, where the therapeutic effect is mediated by a direct effect of the antibody of the invention on immune cells, e.g. to reduce inflammation, it may be advantageous for the antibody to lack any cytotoxic activity.

However, in alternative embodiment, the antibody polypeptides of the invention may be augmented with a functional moiety to facilitate their intended use, for example as a diagnostic (e.g. in vivo imaging) agent or therapeutic agent. Thus, in one embodiment, the antibody polypeptide is linked, directly or indirectly, to a therapeutic moiety. A suitable therapeutic moiety is one that is capable of reducing or inhibiting the growth, or in particular killing, a cancer cell (or associated stem cells or progenitor cells). For example, the therapeutic agent may be a cytotoxic moiety, such as a radioisotope (e.g. $^{90}$Y, $^{177}$Lu, $^{99}$Tc$^m$, etc) or cytotoxic drug (e.g. antimetabolites, toxins, cytostatic drugs, etc).

Alternatively, the cytotoxic moiety may comprise or consist of one or more moieties suitable for use in activation therapy, such as photon activation therapy, neutron activation therapy, neutron-induced Auger electron therapy, synchrotron irradiation therapy or low energy X-ray photon activation therapy.

Optionally, the antibody polypeptide of the invention may further comprise a detectable moiety. For example, a detectable moiety may comprise or consist of a radioisotope, such as a radioisotope selected from the group consisting of $^{99m}$Tc, $^{111}$In, $^{67}$Ga, $^{68}$Ga, $^{72}$As, $^{89}$Zr, $^{123}$I and $^{201}$Tl Optionally, the agent may comprise a pair of detectable and cytotoxic radionuclides, such as $^{86}$Y/$^{90}$Y or $^{124}$I/$^{211}$At. Alternatively, the antibody polypeptide may comprise a radioisotope that is capable of simultaneously acting in a multimodal manner as a detectable moiety and also as a cytotoxic moiety to provide so-called "Multimodality theragnostics". The binding moieties may thus be coupled to nanoparticles that have the capability of multi-imaging (for example, SPECT, PET, MRI, Optical, or Ultrasound) together with therapeutic capability using cytotoxic drugs, such as radio-nuclides or chemotherapy agents.

Therapeutic and/or detectable moieties (such as a radioisotope, cytotoxic moiety or the like) may be linked directly, or indirectly, to the antibody or fragment thereof. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10, tetraacetic acid (DOTA), deferoxamine (DFO), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), derivatives of 3,6,9,15-Tetraazabicyclo[9.3.1]-pentadeca-1 (15), 11,13-triene-4-(S)-(4-isothiocyanato-benzyl)-3,6,9-triacetic acid (PCTA), derivatives of 5-S-(4-Aminobenzyl)-1-oxa-4,7,10-triazacyclododecane-4,7,10-tris(acetic acid) (DO3A) and other chelating moieties.

One preferred linker is DTPA, for example as used in $^{177}$Lu-DTPA-[antibody polypeptide of the invention]. A further preferred linker is deferoxamine, DFO, for example as used in $^{89}$Zr-DFO-[antibody polypeptide of the invention].

However, it will be appreciated by persons skilled in the art that many medical uses of the antibody polypeptides of the invention will not require the presence of a cytotoxic or diagnostic moiety.

As discussed above, methods for the production of antibody polypeptides of the invention are well known in the art.

Conveniently, the antibody polypeptide is or comprises a recombinant polypeptide. Suitable methods for the production of such recombinant polypeptides are well known in the art, such as expression in prokaryotic or eukaryotic hosts cells (for example, see Green & Sambrook, 2012, *Molecular Cloning, A Laboratory Manual*, Fourth Edition, Cold Spring Harbor, N.Y., the relevant disclosures in which document are hereby incorporated by reference).

Although the antibody may be a polyclonal antibody, it is preferred if it is a monoclonal antibody, or that the antigen-binding fragment, variant, fusion or derivative thereof, is derived from a monoclonal antibody.

Suitable monoclonal antibodies may be prepared by known techniques, for example those disclosed in "*Monoclonal Antibodies; A manual of techniques*", H Zola (CRC Press, 1988) and in "*Monoclonal Hybridoma Antibodies: Techniques and Application*", SGR Hurrell (CRC Press, 1982). Polyclonal antibodies may be produced which are poly-specific or mono-specific. It is preferred that they are mono-specific.

Antibody polypeptides of the invention can also be produced using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

It will be appreciated by persons skilled in the art that antibody polypeptides of the invention may alternatively be synthesised artificially, for example using well known liquid-phase or solid phase synthesis techniques (such as t-Boc or Fmoc solid-phase peptide synthesis).

A third aspect of the invention provides an isolated nucleic acid molecule encoding an antibody or antigen-binding fragment of the first or second aspect of the invention, or a component polypeptide chain thereof. By "nucleic acid molecule" we include DNA (e.g. genomic DNA or complementary DNA) and mRNA molecules, which may be single- or double-stranded. By "isolated" we mean that the nucleic acid molecule is not located or otherwise provided within a cell.

In one embodiment, the nucleic acid molecule is a cDNA molecule.

Preferably, the nucleic acid molecule comprises one or more nucleotide sequence selected from either SEQ ID NO: 9 and SEQ ID NO: 10, reproduced below.

Nucleotide Sequence Encoding VH Region of "1630"

[SEQ ID NO: 9]
GAGGTGCAGCTGTTGGAGAGCGGGGGAGGCTTGGTACAGCCTGGGGGTC

CCTGCGCCTCTCCTGTGCAGCCAGCGGATTCACCTTTGGTTACTCTTACA

TGTCTTGGGTCCGCCAGGCTCCAGGGAAGGGGCTGGAGTGGGTCTCATCT

ATTGGTTCTGGTTCTTCTTACACATACTATGCAGACTCCGTGAAGGGCCG

GTTCACCATCTCCCGTGACAATTCCAAGAACACGCTGTATCTGCAAATGA

ACAGCCTGCGTGCCGAGGACACGGCTGTATATTATTGTGCGCGCGTTTAC

TCTTCTCCGGGTATTGACTATTGGGGCCAGGGAACCCTGGTCACCGTCTC

CTCA

Nucleotide Sequence Encoding VL Region of "1631"

[SEQ ID NO: 10]
GACATCCAGATGACCCAGTCTCCATCCTCCCTGAGCGCATCTGTAGGAGA

CCGCGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCACGTTTCAGTGGCAGTGGAAG

CGGGACAGATTTCACTCTCACCATCAGCAGTCTGCAACCTGAAGATTTTG

CAACTTATTACTGTCAACAGTACTACACTTGGGTTCCGTTCACTTTTGGC

CAGGGGACCAAGCTGGAGATCAAA

In an alternative preferred embodiment, the nucleic acid molecule comprises one or more nucleotide sequence selected from either SEQ ID NO: 27 and SEQ ID NO: 28, reproduced below.

Nucleotide Sequence Encoding VH Region of "2674"

[SEQ ID NO: 27]
gaggtgcagttgttggaatctggcggaggattggtgcagcctggcggatc tctgagactgtcttgtgccgcctctggcttcaacttcggctactcctaca tgtcctgggtccgacaggtcctggcaaaggactggaatgggtgtcctcc atcggctccaccagctctcacacctactacgccgattccgtgaagggcag attcaccatcagccgggacaactccaagaacaccctgtacctgcagatga actccctgagagccgaggacaccgccgtgtactactgtgccagagtgtac tcctctcctggcatcgattattggggccagggcacactggtcaccgtgtc ctctgcttctaccaagggaccctctgtgttccctctggctccttgctcca gatccacctctgagtctaccgctgctctgggctgcctggtcaaggattac tttcctgagcctgtgaccgtgtcttggaactccggtgctctgacatccgg cgtgcacacatttccagctgtgctgcagtcctccggcctgtactctctgt cctctgtcgtgaccgtgccttctagctctctgggcaccaagacctacacc tgtaacgtggaccacaagccttccaacaccaaggtggacaagcgcgtgga atctaagtacggccctccatgtccaccatgtcctgctccagaattcctcg gcggaccaagcgtgttcctgtttcctccaaagcctaaggacaccctgatg atctctcggacccctgaagtgacctgcgtggtggtggatgtgtctcaaga ggacccagaagtgcagttcaattggtacgtggacggcgtggaagtgcaca acgccaagaccaagcctagagaggaacagttcaactccacctacagagtg gtgtccgtgctgaccgtgctgcaccaggattggctgaacggcaaagagta caagtgcaaggtgtccaacaagggcctgccttccagcatcgaaaagacca tctccaaggctaagggccagcctcgggaacctcaggtttacaccctgcct ccaagccaagaggaaatgaccaagaaccaggtgtccctgacctgcctcgt gaagggattctaccttccgatatcgccgtggaatgggagtctaacggcc agccagagaacaactacaagacaacccctcctgtgctggactccgacggc tctttcttcctgtattctcgcctgaccgtggacaagtctcggtggcaaga gggcaacgtgttctcctgctctgtgatgcacgaggccctgcacaaccact acacacagaagtccctgtctctgccctgggcaag Nucleotide Sequence Encoding VL Region of "2675"

[SEQ ID NO: 28]
gacatccagatgacccagtctccatcctctctgtctgcctctgtgggcga cagagtgaccatcacctgtcgggcttctcagtccatcggcagcaccctga actggtatcagcagaagcctggcaaggcccctaagctgctgatctatggc gctagctctctgcagtctggcgtgccctctagattttccggctctggctc tggcaccgacttcaccctgacaatcagttccctgcagcctgaggacttcg ccacctactactgccagcagtactacacctgggtgccctttacctttggc cagggcaccaagctggaaatcaagagaaccgtggccgctccttccgtgtt catcttcccaccatctgacgagcagctgaagtccggcacagcttctgtcg tgtgcctgctgaacaacttctaccctcgggaagccaaggtgcagtggaag gtggacaatgccctgcagtccggcaactcccaagagtctgtgaccgagca ggactccaaggactctacctacagcctgtcctccacactgaccctgtcta aggccgactacgagaagcacaaggtgtacgcctgcgaagtgacccatcag ggactgtctagccccgtgaccaagtccttcaacagaggcgagtgt It will be appreciated by persons skilled in the art that the nucleic acid molecule may be codon-optimised for expression of the antibody polypeptide in a particular host cell, e.g. for expression in human cells (for example, see Angov, 2011, Biotechnol. J. 6(6):650-659, the disclosures of which are incorporated herein by reference).

Also included within the scope of the invention are the following:

(a) a fourth aspect of the invention provides a vector (such as an expression vector) comprising a nucleic acid molecule according to the third aspect of the invention;

(b) a fifth aspect of the invention provides a host cell (such as a mammalian cell, e.g. human cell, or Chinese hamster ovary cell, e.g. CHOK1SV cells) comprising a nucleic acid molecule according to the third aspect of the invention or a vector according to the fourth aspect of the invention; and (c) a sixth aspect of the invention provides a method of making an antibody polypeptide according to the first or second aspect of the invention comprising culturing a population of host cells according to the fifth aspect of the invention under conditions in which said polypeptide is expressed, and isolating the polypeptide therefrom.

A seventh aspect of the invention provides a pharmaceutical composition comprising a pharmaceutically effective amount of an antibody or antigen-binding fragment according to the first or second aspect of the invention and a pharmaceutically-acceptable diluent, carrier, adjuvant or excipient.

It will be appreciated by persons skilled in the art that additional compounds may also be included in the pharmaceutical compositions, including, chelating agents such as EDTA, citrate, EGTA or glutathione.

The pharmaceutical compositions may be prepared in a manner known in the art that is sufficiently storage stable and suitable for administration to humans and animals. For example, the pharmaceutical compositions may be lyophilised, e.g. through freeze drying, spray drying, spray cooling, or through use of particle formation from supercritical particle formation.

By "pharmaceutically acceptable" we mean a non-toxic material that does not decrease the effectiveness of the CD137-binding activity of the antibody polypeptide of the invention.

Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), the disclosures of which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the antibody polypeptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the antibody polypeptide of the invention. The adjuvant may be one or more of zinc, copper or silver salts with different anions, for example, but not limited to fluoride, chloride, bromide, iodide, thiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly(vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g. for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The antibody polypeptides of the invention may be formulated into any type of pharmaceutical composition known in the art to be suitable for the delivery thereof.

In one embodiment, the pharmaceutical compositions of the invention may be in the form of a liposome, in which the antibody polypeptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(caprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylene-glycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the antibody polypeptide may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active antibody polypeptide. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, vaginal and rectal. Also, administration from implants is possible.

In one preferred embodiment, the pharmaceutical compositions are administered parenterally, for example, intravenously, intracerebroventricularly, intraarticularly, intraarterially, intraperitoneally, intrathecally, intraventricularly, intrasternally, intracranially, intramuscularly or subcutaneously, or they may be administered by infusion techniques. They are conveniently used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Thus, the pharmaceutical compositions of the invention are particularly suitable for parenteral, e.g. intravenous, administration.

Alternatively, the pharmaceutical compositions may be administered intranasally or by inhalation (for example, in the form of an aerosol spray presentation from a pressurised container, pump, spray or nebuliser with the use of a suitable propellant, such as dichlorodifluoromethane, trichlorofluoro-methane, dichlorotetrafluoro-ethane, a hydrofluoroalkane such as 1,1,1,2-tetrafluoroethane (HFA 134A3 or 1,1, 1,2,3,3,3-heptafluoropropane (HFA 227EA3), carbon dioxide or other suitable gas). In the case of a pressurised aerosol, the dosage unit may be determined by providing a valve to deliver a metered amount. The pressurised container, pump, spray or nebuliser may contain a solution or suspension of the active polypeptide, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the antibody polypeptides of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For ophthalmic use, the antibody polypeptides of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the antibody polypeptide of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The pharmaceutical compositions will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the does may be provided as a continuous infusion over a prolonged period.

In the context of diagnostic use of the antibody polypeptides of the invention, a 'pharmaceutically effective amount', or 'effective amount', or 'diagnostically effective', as used herein, refers to that amount which provides a detectable signal for diagnosis, e.g. for in vivo imaging purposes.

The antibody polypeptides can be formulated at various concentrations, depending on the efficacy/toxicity of the polypeptide being used. For example, the formulation may comprise the active antibody polypeptide at a concentration of between 0.1 µM and 1 mM, more preferably between 1 µM and 500 µM, between 500 µM and 1 mM, between 300 µM and 700 µM, between 1 µM and 100 µM, between 100 µM and 200 µM, between 200 µM and 300 µM, between 300 µM and 400 µM, between 400 µM and 500 µM, between 500 µM and 600 µM, between 600 µM and 700 µM, between 800 µM and 900 µM or between 900 µM and 1 mM. Typically, the formulation comprises the active antibody polypeptide at a concentration of between 300 µM and 700 µM.

Typically, the therapeutic dose of the antibody polypeptide (with or without a therapeutic moiety) in a human patient will be in the range of 100 µg to 1 g per administration (based on a body weight of 70 kg, e.g. between 300 µg to 700 mg per administration). For example, the maximum therapeutic dose may be in the range of 0.1 to 10 mg/kg per administration, e.g. between 0.1 and 5 mg/kg or between 1 and 5 mg/kg or between 0.1 and 2 mg/kg. It will be appreciated that such a dose may be administered at different intervals, as determined by the oncologist/physician; for example, a dose may be administered daily, twice-weekly, weekly, bi-weekly or monthly.

It will be further appreciated by persons skilled in the art that the polypeptides and pharmaceutical formulations of the present invention have utility in both the medical and veterinary fields. Thus, the methods of the invention may be used in the treatment of both human and non-human animals (such as horses, dogs and cats). Preferably, however, the patient is human.

For veterinary use, the agents, medicaments and pharmaceutical compositions of the invention are administered as a suitably acceptable formulation in accordance with normal veterinary practice and the veterinary surgeon will determine the dosing regimen and route of administration which will be most appropriate for a particular animal.

An eighth aspect of the invention provides an antibody or antigen-binding fragment thereof according to the first or second aspect of the invention for use in medicine.

In one embodiment, the antibody polypeptides and formulations of the invention may be used to treat patients or subjects who suffer from or are at risk of suffering from a cancer.

By 'treatment' we include both therapeutic and prophylactic treatment of the patient. The term 'prophylactic' is used to encompass the use of an agent, or formulation thereof, as described herein which either prevents or reduces the likelihood of a cancer, or the spread, dissemination, or metastasis of cancer cells in a patient or subject. The term 'prophylactic' also encompasses the use of an agent, or formulation thereof, as described herein to prevent recurrence of a cancer in a patient who has previously been treated for the neoplastic disorder.

The cancer may be associated with formation of solid tumours or may be a haematologic cancer. Cancer types that may be treated include carcinomas, sarcomas, lymphomas, leukemias, blastomas and germ cell tumours.

For example, the antibody or antigen-binding fragment thereof may be for use in the treatment of a cancer selected from the group consisting of prostate cancer; breast cancer; colorectal cancer; kidney cancer; pancreatic cancer; ovarian cancer; lung cancer; cervical cancer; rhabdomyosarcoma; neuroblastoma; bone cancer; multiple myeloma; leukemia (such as acute lymphoblastic leukemia [ALL] and acute myeloid leukemia [AML]), skin cancer (e.g. melanoma), bladder cancer and glioblastoma.

In one embodiment, the cancer may be selected from the list of cancers in Table 16 or Table 17.

Typically, the therapeutic agents of the invention will be administered in parenteral form, for example by injection into the bloodstream or at/near the site of a tumour.

In one embodiment, the agent for treating a patient who has been pre-screened and identified as having a tumour with cells expressing CD137 and FcγR, such as FcγRI, FcγRIIA, FcγRIIB or combinations thereof.

Related aspects of the invention provide the following:
(i) use of an antibody or antigen-binding fragment thereof according to the first or second aspect of the invention in the preparation of a medicament for treating cancer; and
(ii) a method for treating an individual with cancer, the method comprising the step of administering to an individual in need thereof an effective amount of an antibody or antigen-binding fragment thereof according to the first or second aspect of the invention.

It will be further appreciated that the antibody-based agents of the invention may be used as a sole treatment for cancer in a patient or as part of a combination treatment (which further treatment may be a pharmaceutical agent, radiotherapy and/or surgery).

Thus, the patient may also receive one or more further treatments for cancer, for example pharmaceutical agents (such as chemotherapeutic agents), radiotherapy and/or surgery.

For example, the pharmaceutical compositions of the invention may be administered in combination with other therapeutic agents used in the treatment of cancers, such as antimetabolites, alkylating agents, anthracyclines and other cytotoxic antibiotics, vinca alkyloids, etoposide, platinum compounds, taxanes, topoisomerase I inhibitors, antiproliferative immunosuppressants, corticosteroids, sex hormones and hormone antagonists, and other therapeutic antibodies (such as trastuzumab).

In one embodiment, the one or more further treatments are selected from the group consisting of conventional chemotherapeutic agents (such as alkylating agents, antimetabolites, plant alkaloids and terpenoids, topoisomerase inhibitors and antineoplastics), radiotherapeutic agents, antibody-based therapeutic agents (such as gemtuzumab, alemtuzumab, rituximab, trastuzumab, nimotuzumab, cetuximab, bevacizumab), and steroids.

A ninth aspect of the invention provides a method of identifying a patient susceptible to treatment with an antibody according to the first or second aspect of the invention, comprising screening a patient to identify if they have a tumour with cells expressing CD137 and FcγR.

Optionally, the FcγR that is screened for is FcγRIIA. In one embodiment, the FcγRIIA is the R131 allotype.

Suitable biomarker screening methods are well known in the art. For example, a tumour biopsy sample may be taken from the patient and analysed to determine the level of expression (at an RNA level and/or protein level) of CD137 and/or FcγRs therein; for example using immunohistochemistry, flow cytometry or proteomic approaches.

Preferences and options for a given aspect, feature or parameter of the invention should, unless the context indicates otherwise, be regarded as having been disclosed in combination with any and all preferences and options for all other aspects, features and parameters of the invention.

The listing or discussion of an apparently prior-published document in this specification should not necessarily be taken as an acknowledgement that the document is part of the state of the art or is common general knowledge.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the above description and the accompanying drawings. It should be understood, however, that the above description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

The following drawings form part of the present specification and are included to further demonstrate certain aspects of the present invention. The invention may be better understood by reference to one or more of these drawings in combination with the detailed description of specific embodiments presented herein.

Preferred, non-limiting examples which embody certain aspects of the invention will now be described, with reference to the following figures:

FIG. 2 shows the CD137 variants in Example 6.

EXAMPLES

Figure 1:
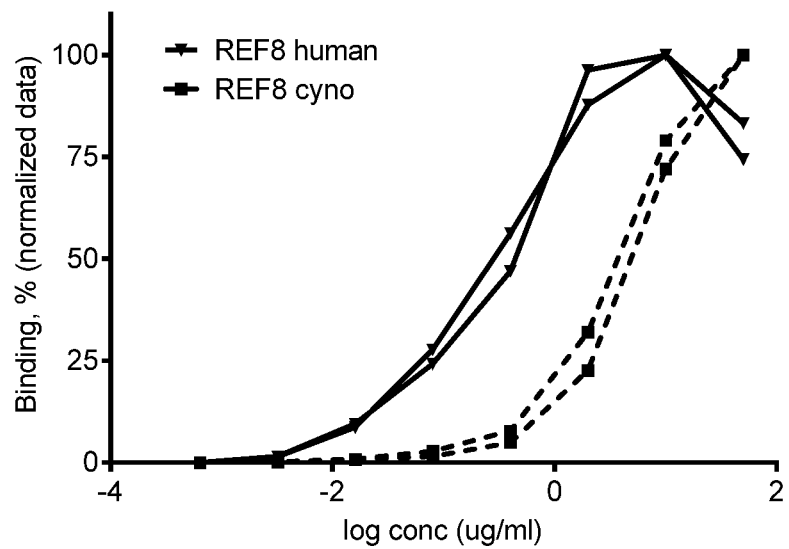
FIG. 1 shows binding to CD137 human and cynomolgus CD137. Data from separate two experiments included.
Figure 1:
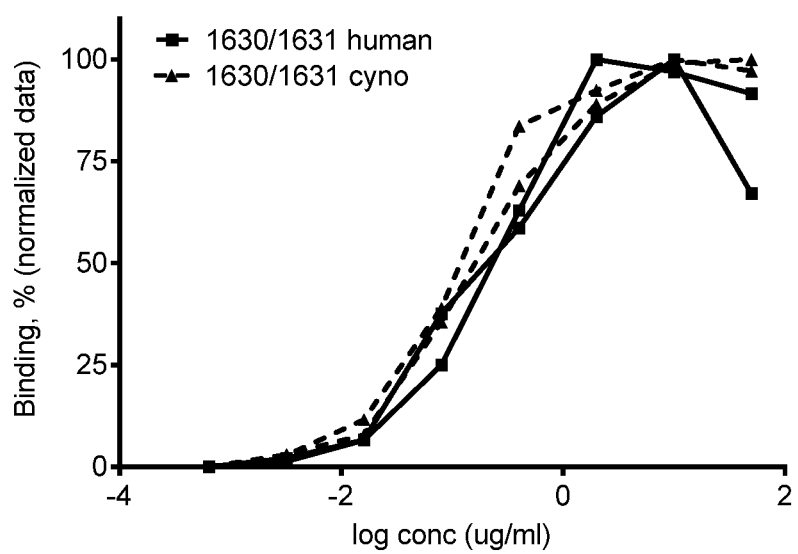

Example 1—Selection of CD137 Antibodies from Alligator GOLD

Phage display selections were performed using a human antibody (scFv) library, Alligator GOLD. Selections towards recombinant CD137 in soluble form, coated onto the surface of beads or tubes, or expressed on the surface of CD137-transfected cells were performed. CTLA4-Fc and an irrelevant His-tagged protein were used as non-targets included in excess in the selections. Prior to each selection round, the phage stocks were pre-selected towards non-target proteins, beads or CD137 negative cells to remove unspecific binders.

To identify specific binders from the phage selection, approximately 4500 individual clones were screened in phage format using ELISA coated with either recombinant target (CD137-Fc) or non-target protein, followed by confirmation as soluble scFv for some clones. Clones exhibiting specific binding to CD137 were sequenced and unique clones were produced as IgG for further characterization.

Example 2—Binding to Human CD137 Measured by ELISA

Aim

The aim was to determine binding potency of the CD137 antibody.

Material and Methods

Binding of CD137 antibodies to recombinant human CD137 was determined by sandwich ELISA. Briefly, ELISA plates (Greiner #655074) coated with recombinant human CD137-Fc (R&D #838-4B) were incubated with serial dilutions of the various CD137 antibodies to be investigated. CD137 antibodies were detected using HRP-conjugated goat-anti-human kappa light chain (AbD Serotec # STAR127P) and developed with SuperSignal ELISA Pico Chemiluminescent substrate (Pierce #37069). EC50 values of the various antibodies were determined in 2-6 separate experiments.

Two different reference antibodies with specificity for CD137, synthesized from published amino acid sequence information, were used in this study (designated "REF1" and "REF2").

The other reference antibodies used, namely REF3, REF4 and REF8, are human CD137-specific monospecific IgG antibodies obtained from the Alligator GOLD library. They are agonistic and stimulate T cells upon binding to CD137. The binding epitopes of the reference antibodies has been established as outlined in Examples 6-8 (see below).

The reference antibodies were selected because they have previously undergone at least some clinical testing and so represent the benchmark against which new anti-CD137 antibodies can be judged for improved properties and/or function.

Results and Conclusion

Exemplary antibody 1630/1631 exhibits EC50 values in a similar range as those of the reference antibodies, i.e. sub nM. Data is summarized in Table 1.

TABLE 1

EC50 values (nM) of CD137 antibodies determined by ELISA for human CD137.

| Antibody | Mean | SD | n |
|---|---|---|---|
| REF1 | 0.75 | 0.137 | 8 |
| REF2 | 0.33 | 0.069 | 5 |
| REF3 | 0.39 | 0.037 | 3 |
| REF4 | 0.41 | 0.050 | 4 |
| REF8 | 0.38 | 0.137 | 2 |
| 1630/1631 | 0.27 | 0.078 | 4 | n = number of data points.

Example 3—Binding to Human and Cynomolgus CD137 Measured by Flow Cytometry

Aim

The aim of this study was to determine the binding to human and cynomolgus (*Macaca fascicularis*) CD137.

Material and Methods

Binding and EC50 was determined using flow cytometric of CHO cells transfected with human CD137, cynomolgus CD137 or empty vector. The extracellular part of human or cynomolgus CD137 was fused to the transmembrane and intracellular part of human CD40 and cloned into pcDNA3.1. The vector was subsequently stably transfected into CHO cells. Expression of CD137 was confirmed by flow cytometry using CD137 antibody (human CD137-PE, BD Biosciences #555956) for 30 min at 4° C. CD137-transfected and empty vector-transfected cells were incubated with CD137 antibodies for at least 1 h at 4° C. to saturate the binding. In order to minimize antibody internalization, 0.05% sodium azide was used in the incubation buffer and all work was performed on ice. The CD137 antibodies were detected using PE-conjugated anti-hIgG antibody (109-115-098, Jackson Immunoresearch laboratories), incubated for 30 min at 4° C. Directly after staining the cells were fixed with a paraformaldehyde solution (10× concentrate BD CellFIX, BD biosciences #340181). Cells were analyzed by flow cytometry using FACSVerse (BD Biosciences). The median fluorescence intensity (MFI) for each sample was determined and the dose response data was analysed using Graph Pad Prism.

MFI data was normalized for each antibody, where 0% is defined as the lowest value and 100% is the highest value in the dose titration for each antibody. EC50 and 95% confidence interval were calculated with Graph Pad Prism based on data from the two experiments (non-linear regression (curve fit), constraints set to 0 and 100).

Results and Conclusion

Binding to CHO-huCD137, CHO-cyCD137 and CHO-pcDNA was confirmed in two separate experiments (FIG. 1). 1630/1631 binds to human CD137 with EC50 comparable with the two reference antibodies REF1 and REF2. 1630/1631 binds well to cynomolgus CD137. Reference antibody REF1 and REF8 (FIG. 1) binds very weakly or not at all to cynomolgus CD137. REF8 exhibits weak binding and does not reach a complete saturation.

The EC50 determination is presented as 95% confidence intervals for each CD137 antibody tested in order to include the inter and intra assay variations (Table 2).

TABLE 2

95% confidence intervals for the EC50 of each CD137 antibody determined as an average from two experiments of normalized data.

| Antibody | Binding to human CD137, EC50 (µg/mL) | Binding to cyno CD137, EC50 (µg/mL) | Ratio, cyno:human |
|---|---|---|---|
| REF1 | 1.00-1.99 | Nd | Nd |
| REF2 | 0.21-0.31 | 0.13-0.24 | 0.69 |
| REF3 | 0.20-0.36 | Nd | Nd |
| REF4 | 0.16-0.27 | 0.11-0.17 | 0.67 |
| REF8 | 0.20-0.42 | >3 | >14 |
| 1630/1631 | 0.17-0.26 | 0.12-0.16 | 0.63 |

Nd: Not detectable

Example 4—Affinity Measured by Biacore

Aim

The aim was to estimate the affinity, on rate and off rate of the different CD137 antibodies.

Material and Methods

Human CD137 (R&D systems) was immobilized to the Biacore™ sensor chip, CM5, using conventional amine coupling. The tested antibody and control (serially diluted ½ 10-0.63 nM) were analyzed for binding in HBS-P (GE, # BR-1003-68) at a flow rate of 30 µl/ml. The association was followed for 5 minutes and the dissociation for 15 minutes. Regeneration was performed twice using 10 mM Glycine pH 1.7 for 30 seconds. The kinetic parameters and the affinity constants were calculated using 1:1 Langmuir model.

Results and Conclusion

The affinities of the antibodies were in the nanomolar to sub-nanomolar range (Table 3) measured using bivalent antibodies flowed over CD137 coated on the chip surface.

TABLE 3

Kinetic parameters measured by surface plasmon resonance

| Antibody | ka (1/Ms) | kd (1/s) | KD (M) |
|---|---|---|---|
| REF4 | 6.76E+05 | 6.60E-04 | 9.76E-10 |
| REF8 | 3.92E+05 | 5.19E-04 | 1.32E-09 |
| 1630/1631 | 1.85E+06 | 1.18E-03 | 6.41E-10 |
| REF2 | 1.05E+06 | 4.45E-04 | 4.24E-10 |

Example 5—Target Specificity of the CD137 Antibodies

Aim

The aim with this study was to evaluate the risk that any of the CD137 antibody binds targets other than CD137.

Material and Methods

Binding to TNFR superfamily members for which ELISA methods had already been established (CD40 and OX40) was evaluated to detect potential propensity to cross react to non-target proteins. In addition, a BLAST search was performed identifying TNFRSF21 as the most similar sequence (34% sequence identity). Since this sequence similarity is rather low, determination of non-target binding to OX40 and CD40 was considered sufficient.

ELISA plates (Greiner #655074) were coated with 50 µl/well of recombinant human OX40 (R&D #1493-CD), CD40-Fc (Ancell #504-820) or CD137 (R&D #838-4B) diluted to a final concentration of 0.5 µg/ml in PBS for 1 h at 37° C. or overnight at 4° C. Plates were washed with PBS+0.05% TWEEN20 (PBST), followed by block with PBST+1% bovine serum albumin (BSA). Antibody samples were prepared as serial 1/10 dilutions from 10-0.01 µg/ml in PBST+1% BSA and incubated for 1 h in room temperature, followed by detection using a horse radish peroxidase-conjugated anti-human kappa light chain antibody (AbD Serotec # STAR127P) and developed using SuperSignal ELISA Pico Chemiluminescent substrate (Pierce Thermo-Scientific #37069).

Results and Conclusion

TABLE 4

Summary of CD137 antibody unspecific binding to OX40 and CD40

| Antibody | Binding to OX40 and CD40 | EC50 CD137 |
|---|---|---|
| REF3 | No | |
| REF4 | Weak; EC50 > 6 µg/ml (40 nM) | 0.4 nM |
| REF8 | No | |
| 1630/1631 | No | 0.4 nM |
| 2674/2675 | No | 0.3 nM |

The results from the two experiments were similar. One antibody (REF4) exhibited weak binding to OX40 and CD40, whereas none of the remaining antibody showed any detectable binding to either OX40 or CD40. An overview of antibodies analyzed, and results from the two experiments is shown in Table 4.

Further, binding to primary PBL from multiple blood donors was tested. The binding of 1630/1631 and 2674/2675 to PBL was similar to Reference antibodies. No relevant unspecific binding to non-target proteins was detected.

Example 6—Domain Mapping of Antibodies Binding to CD137

Aim

The aim was to define distinct classes of epitope specificity, and compare to the properties of reference antibody.

Material and Methods

The ability of each antibody to bind to a panel of human/mouse CD137 chimeras expressed on the surface of transfected cells was analyzed by flow cytometry.

The chimeras were designed by exchanging domains or modules of the human CD137 with the corresponding mouse domain. Genes of CD137 human/mouse chimeras were synthesized (GenScript) and constructs cloned into pcDNA3.1 vector (Invitrogen) and transiently transfected into FreeStyle 293-F cells (Invitrogen). The transfected cells were incubated with CD137 antibodies and control antibodies, followed by incubation with anti-human IgG-PE (Jackson Immunoresearch) for detection and analyzed with FACS Verse (BD Biosciences). Binding to the different chimeric constructs was calculated as relative MFI compared to the binding of the isotype control, followed by normalization to the full-length human CD137 construct to minimize the effect of affinity differences between individual antibodies.

Results and Conclusion

Three binding patterns was observed as described below FIG. 2. Data is summarized in Table 5.

Pattern A

Antibody REF1 depends on domain 1 for binding to human CD137.

Pattern B

Antibodies REF3, REF4, 2674/2675 and 1630/1631 are mainly dependent on domain 2 for binding to human CD137.

Pattern C

Antibodies REF2 (Reference antibody) and REF8 appear to be mainly dependent on domains 3B-4A for binding to human CD137.

TABLE 5

Median fluorescence intensity (MFI) for antibody sample/isotype control, normalized to full-length human CD137.

| | | Domain | | | | | | |
|---|---|---|---|---|---|---|---|---|
| | | 1 | 2 | | | | 3B-4A | |
| Clone | Description | REF1 | 1630/1631 | 2674/2675 | REF3 | REF4 | REF2 | REF8 |
| 1550 | Human CD137 with mouse domains 1, 2A and 2B (aa 24-86) | 0.12 | 0.11 | 0.13 | 0.05 | 0.05 | 0.22 | 0.17 |
| 1551 | Human CD137 with mouse domains 2A, 2B and 3A (aa 47-96) | 0.41 | 0.10 | 0.15 | 0.04 | 0.05 | 0.37 | 0.33 |
| 1552 | Human CD137 with mouse domains 2B, 3A and 3B (aa 64-118) | 0.76 | 0.25 | 0.13 | 0.05 | 0.06 | 0.19 | 0.18 |
| 1553 | Human CD137 with mouse domains 3A, 3B and 4A (aa 87-133) | 1.07 | 0.91 | 1.08 | 0.65 | 0.65 | 0.17 | 0.17 |
| 1554 | Human CD137 with mouse domains 3B, 4A and 4B (aa 97-159) | 0.82 | 0.85 | 0.88 | 0.84 | 0.51 | 0.16 | 0.17 |
| 1555 | Human CD137 with mouse domains 1 and 4B and region of unknown function (aa 24-46 and aa 139-186) | 0.11 | 0.35 | 0.38 | 0.24 | 0.26 | 0.26 | 0.32 |
| 1030* | Human full length CD137 | 1 | 1 | 1 | 1 | 1 | 1 | 1 |

Example 7—CD137 Ligand Blocking

Aim and Background

The aim was to determine if the CD137 antibodies block the CD137 ligand binding.

If the CD137 antibodies bind to epitopes close to the ligand binding region, binding to the antigen can lead to partly or total block of ligand biding. Binding close to the CD137 ligand binding epitope may also affect the ligand binding due to steric hindrance or conformational changes of the CD137 ligand binding epitope. All CD137 antibodies were titrated against a fixed concentration of CD137L for evaluation of ligand blocking properties.

Material and Method

CHO-cells transfected with human CD137 were used for the ligand competition. The extracellular part of human CD137 was fused to the transmembrane and intracellular part of hCD40 and cloned into pcDNA3.1. The vector was subsequently stably transfected into CHO cells. The expression of CD137 was confirmed by staining with commercial antibody targeting CD137.

The CHO-huCD137 were pre-incubated with CD137 monoclonal antibodies, titrating down from a predetermined saturating concentration (0.25 µg/ml), for 1 h at +4 C before the addition of CD137 ligand at a concentration at EC50. After co-incubation for another 30 min at +4 C, the cells were washed and bound CD137 ligand was detected with anti-FLAG-APC (Cell signaling technology). Before analyzation the cells were fixed with paraformaldehyde (10× concentrate BD CellFIX, BD biosciences). Analyzation was performed with FACSverse and the MFI (Median Fluorescence Intensity) was calculated with FlowJo software.

Results and Conclusion

Figure 3:
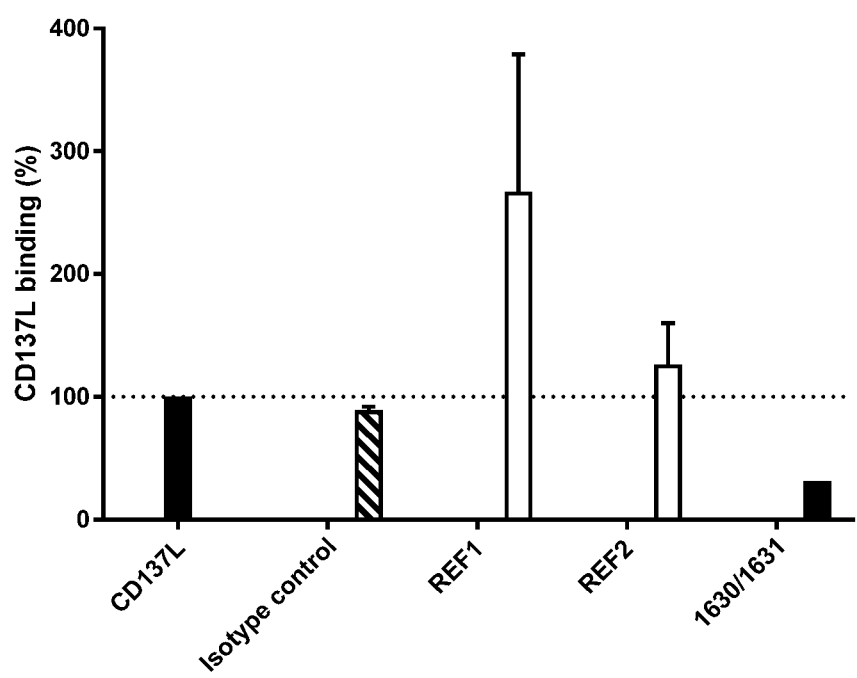
FIG. 3 shows a summary of two experiments of CD137 mAb competition with CD137L binding to CHO-huCD137 cells when titrated (from left to right 25 µg/ml).

It can be concluded that all CD137 mAbs tested were not blocking the CD137 ligand binding (Table 6, FIG. 3). CD137 mAbs belonging to group B and C, binding to domain 2B-4A, block the CD137L (including 2674/2675 and 1630/1631). REF1 belonging to group A which bound to domain 1, did not block CD137 ligand. REF1 increased the binding of the CD137L.

TABLE 6

Maximal CD137 ligand competition of the CD137 antibodies.

| Group (domain mapping) | CD137 mAb | CD137L, max inhib. |
|---|---|---|
| A | REF1 | −167% |
| B | 1630 | 69% |
| B | 2674/2675 | 66% |
| C | REF2 | −26% |

Example 8—Competition ELISA

Aim and Background

By competing each CD137 antibody with each another, it is possible to determine antibodies binding to similar epitopes based on their blocking pattern. The competition ELISA is performed by co-incubating biotinylated CD137 antibodies with non-biotinylated CD137 antibodies when binding to coated CD137-Fc. Competition is defined as loss of signal from the biotinylated CD137 antibody. Low competition values could either be due to no competition between the antibodies or binding kinetics of the antibodies. Binding of one antibody could also lead to steric hindrance or conformational changes when binding the antigen which affects the binding of the other CD137 antibody.

Material and Method

CD137 antibodies were biotinylated (EZ-link NHS-LC-Biotin, ThermoFisher) and intact binding properties to CD137-Fc was verified with ELISA by comparing EC50 between biotinylated and non-biotinylated anti-CD137 mAbs. Non-biotinylated anti-CD137 (anti-CD137-bio) was pre-incubated to CD137-Fc at concentrations 30 times higher than the determined EC50 for 0.5 h. Without washing, anti-CD137-bio was added and co-incubated for another 1 h. The binding of anti-CD137-bio was detected with Streptavidin-HRP (Pierce). Competition was calculated as the relative number by dividing the binding measured to other antibodies relative to its maximum competition (competing with itself). The relative values obtained were normalized against the maximum blocking capacity (Table 7).

TABLE 7

Summary of CD137 antibody competition ELISA from two experiments.

|  | REF1 | REF4 | 1630/1631 | REF2 | REF8 |
|---|---|---|---|---|---|
| REF1 | 100 | 7 | 5 | 5 | 4 |
| REF2 | 15 | 41 | 70 | 94 | 61 |
| REF4 | 18 | 58 | 91 | 63 | 50 |
| REF8 | 4 | 49 | 91 | 100 | 82 |
| 1630/1631 | 14 | 31 | 56 | 23 | 16 |

Result and Conclusion

The competition ELISA was repeated two times. In both experiments, several of the CD137 mAbs did not fully compete with itself (Table 7). The antibody REF1 that belongs to domain mapping group A, displayed a unique pattern in the competition ELISA. The other CD137 antibodies that were analyzed displayed similar blocking patterns. Differences in binding kinetics between those antibodies may explain some of the minor variations in the binding patterns among these antibodies, although it cannot be excluded that the small variations within groups reflects actual differences in the binding epitope.

Example 9—In Vitro Efficacy of CD137 Antibodies

Aim

The aim was to identify CD137 antibodies with agonistic activity.

Material and Methods

Agonistic activity of CD137 antibodies was evaluated in a T cell assay based on primary human $CD8^+$ T cells. Briefly, $CD8^+$ T cells were separated from human peripheral blood mononuclear cells by MACS separation (Miltenyi #130-096-495) according to the manufacturer's protocol. Cells were incubated in 96-well microtiter plates (NuncThermo Scientific #268200), pre-coated with anti-CD3 antibody (clone OKT3, Affymetrix eBioscience #16-0037) and titrated concentrations of the CD137 antibody to be tested. Following 72 or 96-hour incubation, culture medium was harvested and IFN-γ levels were determined by ELISA (BD #555142).

Each clone was analyzed in at least 6 donors and compared to the reference CD137 antibody REF1 and the negative control antibody.

Due to large intra-donor variations the stimulation index (SI, fold induction by antibody compared to negative control) was determined for each sample and normalized to the stimulation index for the reference antibody REF1.

Results and Conclusion

Figure 4:
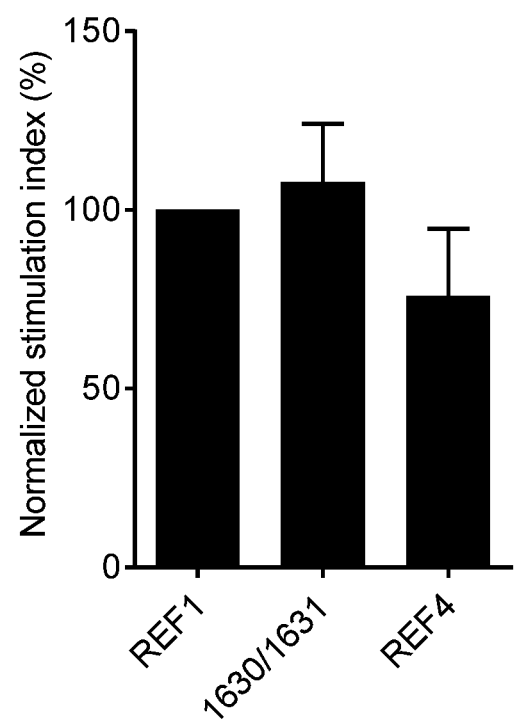
FIG. 4 shows the stimulation index of clones normalized to reference REF1.
Figure 5:
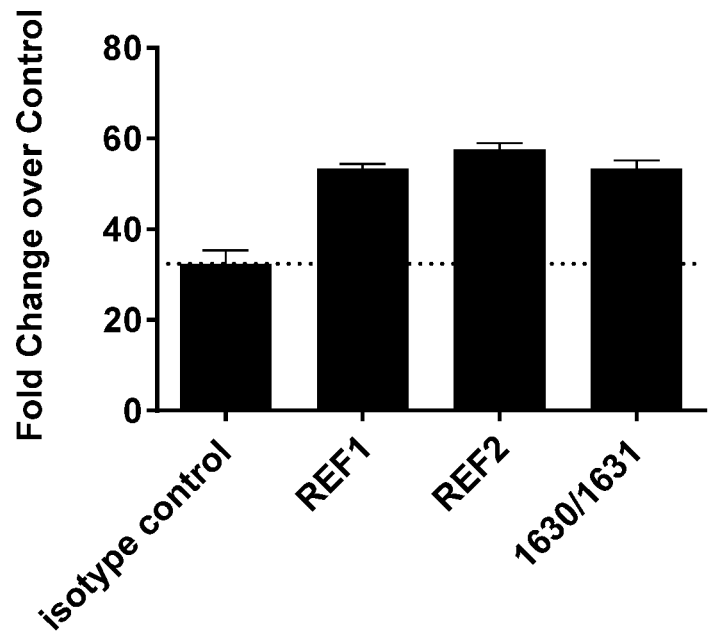
FIG. 5 shows the induction of NF-κB mediated signaling by the antibodies with and without cross-linking.
Figure 5:
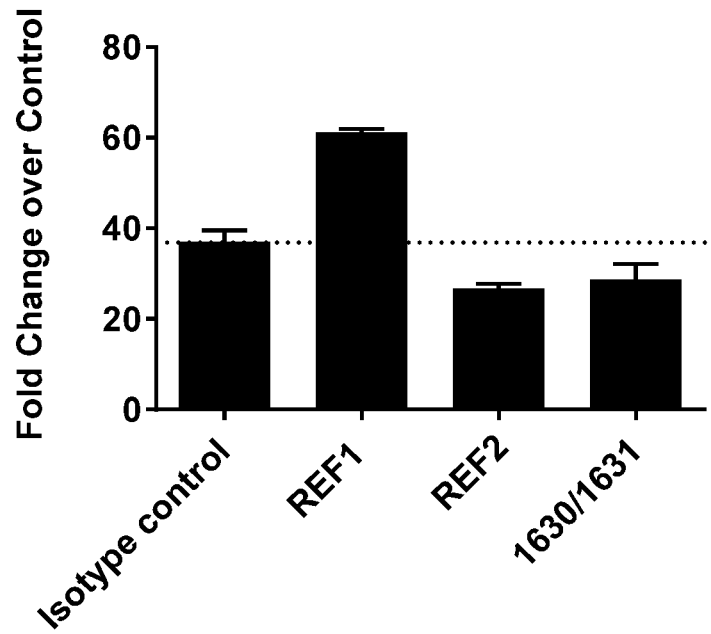

Several clones with efficacy comparable to the reference REF1 were identified. Data is summarized in FIG. 4.

Table 8 indicates the absolute IFN-γ levels induced by CD137 stimulation. However, all antibodies were not analyzed head-to-head in all donors, and the normalized SI is more relevant for comparison of the efficacy.

TABLE 8

IFN-γ production levels induced by the various antibody.

| Clone name | Mean IFN-γ (pg/ml) | Min IFN-γ (pg/ml) | Max IFN-γ (pg/ml) | n |
|---|---|---|---|---|
| Ctrl IgG | 2502 | 337 | 8526 | 13 |
| REF1 | 42268 | 2256 | 136802 | 12 |
| REF4 | 26749 | 11952 | 51832 | 8 |
| REF8 | 52448 | 7727 | 123127 | 8 |
| 1630/1631 | 51236 | 3361 | 145055 | 8 |

Example 10—In Vitro NFkB Reporter Assay 293T cells (30 million) were transfected with plasmids which encode for human CD137, firefly luciferase under NF-κB promoter and renilla. After 5 hours of transfection, the antibodies were added at three different concentrations. 18 hours later, cells were harvested and luciferase reporter assay (Promega) was performed. The cells were cultured with soluble antibodies without crosslinking, as well as with cross-linking, at 5 μg/ml with crosslinking using anti-IgG antibody.

Results

1630/1631 stimulates CD137 inducing NF-κB mediated signaling when cross linked but not in the absence of a cross linking agent. In contrast, REF1 induce CD137 signaling also in the absence of a cross linking agent.

Example 11—In Vivo Anti-Tumour Effect in HT-29 Colon Cancer Model

Summary

The anti-tumour effect of 1630/1631 was investigated using hPBMC humanized immunodeficient mice and subcutaneous tumour models of HT-29 colon carcinoma. 1630/1631 demonstrated statistically significant tumour volume inhibition.

Material and Methods

Leukocyte concentrates were obtained from Lund University Hospital.

Female SCID-Beige mice (7-8w) from Taconic's Denmark were used in the experiments. All experiments were done by approval of Malmö/Lund ethical committee.

HT-29 colon cancer were obtained from ATCC and cultivated according to ATCC recommendations. The HT-29 cell line growing in log phase was injected subcutaneously ($4 \times 10^6$ cells in 200 μL at day 0 (D0)). Human PBMC ($7 \times 10^6$ in 100 μL) isolated from leukocyte concentrates was injected intraperitoneally at the same day. Intraperitoneal treatments (100 μg) were done at days 6, 13, and 20.

Tumour was measured with a calliper in width, length and height of which the tumour volume calculated (w/2×l/2×h/2×pi×(4/3)). The animals were terminated before the tumour volume reached 2 cm$^3$, at wounding, or affected health of the mice.

The data were analyzed by Mann-Whitney test using the GraphPad Prism program.

Results

Figure 6:
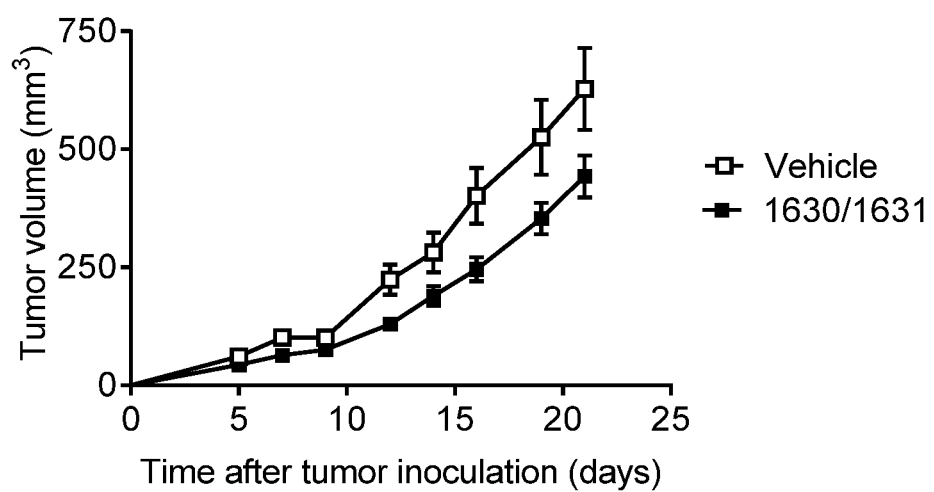
FIG. 6 shows the effect of treatment with the 1630/1631 antibody on tumour volume in a mouse tumour model.

Pooled data from mice engrafted with 4 different donors demonstrated statistically significant anti-tumour efficacy at days 12-16 in the form of inhibition of tumour growth when treated with the 1630/1631 antibody (p=0.0675 to p=0.0132, Mann-Whitney non parametric, 2-tail) in comparison to the vehicle group. The percentage of tumour volume inhibition ranged from 29-42% with 1630/1631 between days 10 and 21 (see FIG. 6 and Table 9).

In conclusion, the anti-tumour effect of 1630/1631 was investigated using hPBMC humanized immunodeficient mice and subcutaneous tumour models of HT-29 colon carcinoma. 1630/1631 demonstrated statistically significant tumour volume inhibition.

TABLE 9

Statistical analysis and percent tumour inhibition

| Day after tumour inoculation | Tumour growth inhibition (tumour volume) compared to vehicle (%) | p-value (Mann-Whitney 2-tail) |
|---|---|---|
| D12 | 42.1 | 0.0132 |
| D14 | 32.6 | 0.0675 |
| D16 | 38.7 | 0.0304 |
| D19 | 32.7 | 0.1918 |
| D21 | 29.5 | 0.0911 |

Example 12—Optimization of CD137 Parental Antibody Clone 1630/1631

The aim of the optimization was to generate improved variants of the 1630/1631 antibody with regard to affinity and biophysical properties. Phage selections towards recombinant CD137 coated onto the surface of beads were performed and prior to each selection round, the phage stocks were pre-selected towards non-target proteins as well as beads. Prior to the fourth round of selection a thermal incubation step at 65° C. were performed. Overall the selection strategy was designed to promote the isolation of clones with a slow off-rate as well as a fast on-rate by prolonging the washing steps and decreasing the incubation time between the phage pool and CD137.

After phage selections, screening was performed in a soluble scFv format to identify target binding clones as well as to evaluate the diversity. An extended primary screening was performed to identify clones with improved temperature stability, cynomolgus reactivity as well as affinity or off-rate. A total of 50 clones were re-cloned into the final IgG4 format having the S228P stabilizing mutation. Further evaluation of optimized variants was performed in the final format and was focused on binding in an ELISA set-up, cell-binding as determined by FACS, affinity, temperature stability as determined by both an ELISA set-up as well as DSF, SE-HPLC, Schrödinger modelling and specificity.

Example 13—Improved Stability of Clone 2674/2675

The aim with the DSF analysis was to determine the Tm of the clone 2674/2675 compared to the parental clone 1630/1631 to evaluate the improvement in temperature stability after optimization.

Material and Method

All antibodies were analyzed with differential scanning fluorometry (DSF) at SARomics Biostructure. Samples were diluted to 0.1 mg/ml in sterile filtered PBS and a volume of 150 µl were delivered to SARomics.

The samples for the DSF measurements (0.1 mg/ml in PBS buffer) were made up of 63 µl sample+7 µl PBS buffer, 1:100 fold diluted SYPRO Orange). In total, the SYPRO Orange was diluted 1:1000-fold. Duplicate measurements were made for each construct using a Stratagene MX3000P, qPCR machine. Measurements were performed in the temperature range 25° C.-95° C. The average melting temperature Tm was calculated for all samples.

Results and Conclusions

Melting curves for all samples were obtained and the determined Tm1 as well as Tm2 for 2674/2675 and parental clone 1630/1631 can be seen in Table 10 below. 2674/2675 had an improved Tm2 by 1-2° C. as compared to the parental clone 1630/1631.

TABLE 10

Determined Tm1 as well as Tm2 values and the average Tm2 difference of 2674/2675 compared to 1630/1631 parental clone as measured by DSF

| | Tm1 (° C.) | Tm2 (° C.) | Improved Tm2 (° C.) |
|---|---|---|---|
| 2674 | 66.3 | 73.4 | 2 |
| 1630 | 66.3 | 71.4 | — |

Example 14—Reduced Aggregation Propensity of Clone 2674/2675 Analyzed by Antibody Aggregation Prediction at Schödinger The aim with the Schrödinger analysis of the optimized variants was to evaluate the size of the hydrophobic patch as well as the aggregation propensity of 2674/2675 in comparison to the parental clone 1630.

Material and Methods

Sequences for the different variants were sent to Schrödinger and 3D structures were generated. The 3D models were analyzed with Protein Surface Analyzer and ranked with Aggscore. REF9-24 are clones obtained during optimization based on binding capacity for human CD137.

Results and Conclusions

Figure 7:
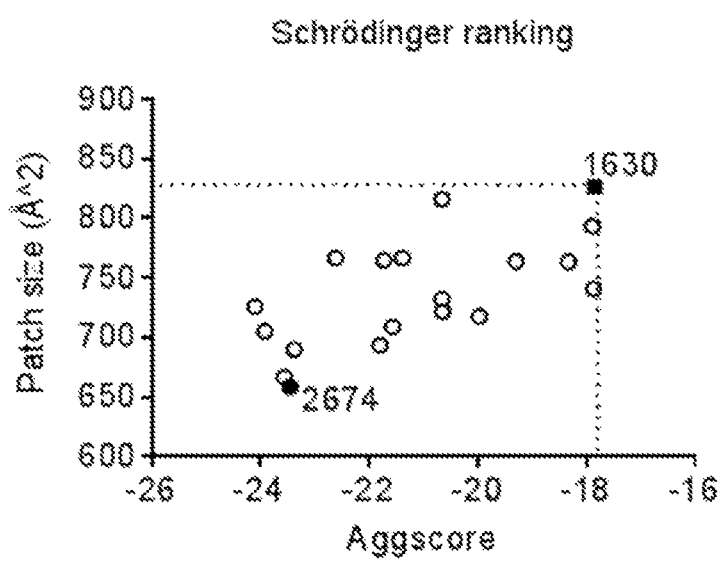
FIG. 7 shows determined patch size and Aggscore for 2674/2675 as well as the parental clone 1630/1631 clone via Schrödinger analysis.

The defined patch size and aggscore for the clones 2674/2675 and REF9-24 (clones obtained during selection) as well as parental clone 1630/1631 can be seen in FIG. 7. It can be concluded that the introduced mutations clearly disrupted the hydrophobic patch and reduced the aggregation propensity according to the modelling analysis.

Example 15—Binding of 2674/2675 to Human and Cynomolgus CD137 Measured by ELISA

Aim and Background

The aim of the evaluation was to determine binding of 2674/2675 compared with parental clone 1630/1631 in ELISA to both human and cynomolgus CD137.

Material and Methods

Binding of CD137 antibodies to recombinant human CD137 was determined by sandwich ELISA. Briefly, ELISA plates (Greiner #655074) coated with recombinant human CD137-Fc (R&D #838-4B) were incubated with serial dilutions of the various CD137 antibodies to be investigated. CD137 antibodies were detected using HRP-conjugated goat-anti-human kappa light chain (AbD Serotec # STAR127P) and developed with SuperSignal ELISA Pico Chemiluminescent substrate (Pierce #37069). EC50 values of the various antibodies were determined in 2-6 separate experiments.

Results and Conclusions

2674/2675 exhibits EC50 values in a similar range as parental clone 1630/1631, i.e. sub nM. Data is summarized in Table 11 below.

TABLE 11

Determined EC50 values as measured by ELISA for 2674/2675 and parental clone 1630/1631.

| | EC50 (nM) human CD137 | EC50 (nM) cyno CD137 |
|---|---|---|
| 2674/2675 | 0.34 | 0.57 |
| 1630/1631 | 0.41 | 0.85 |

Example 16—Binding of 2674/2675 to Human and Cynomolgus CD137, Octet

Aim

The aim was to compare relative binding affinities for 2674/2675 and 1630/1631 to human and cynomolgus CD137 using the Octet platform.

Materials and Method

CD137 affinity was determined using the Octet Red 96 platform (ForteBio). 2674/2675, 1630/1631, REF1, REF 2 and 1188 isotype control were coupled at 10 µg/ml to ARG2 biosensors (ForteBio #18-5092) by amine coupling with EDC and NHS. 7 2-fold serial dilutions of CD137 (Acro Biosystems #41B-H5227 and #41B-052H4) from 100 nM was prepared in 1× kinetic buffer (ForteBio #18-1092). Association was measured for 180 s followed by dissociation for 180 s in 1× kinetic buffer. 10 mM Glycine pH 2.2 was used for regeneration.

Data generated was referenced by reference well subtraction (1188), the baseline was aligned with the y-axis, inter-step correlation by alignment against association was performed and the data was smoothed by a Savitzky-Golay filtering in the data analysis software (v.9.0.0.14). The processed data was fitted using a 1:1 Langmuir binding model with $X^2$ as a measurement of fitting accuracy.

Results and Conclusion

The binding affinities of 2674/2675, 1630/1631 and REF antibodies to human and cynomolgus CD137 are presented in Table 12. The affinity for 2674/2675 to human CD137 was improved by a factor 2 compared to 1630/1631. The affinity for 2674/2675 to cynomolgus CD137 was in the same range as 1630/1631.

TABLE 12

Affinity for human and cynomolgus CD137 to immobilized 2674/2675, 1630/1631 and REF antibodies

| Immobilized antibodies | Human CD137 | | | Cynomolgus CD137 | | |
|---|---|---|---|---|---|---|
| | KD (M) | kon (1/Ms) | koff (1/s) | KD (M) | kon (1/Ms) | koff (1/s) |
| 2674/2675 | 6.9E−09 | 3.5E+05 | 2.4E−03 | 2.5E−08 | 1.6E+05 | 4.0E−03 |
| 1630/1631 | 1.4E−08 | 1.6E+05 | 2.3E−03 | 1.8E−08 | 1.4E+05 | 2.5E−03 |
| REF1 | 3.0E−09 | 4.6E+05 | 1.4E−03 | no binding | | |
| REF 2 | 6.1E−09 | 6.8E+05 | 4.1E−03 | 1.0E−08 | 5.2E+05 | 5.3E−03 |

Example 17—Binding Affinity of 2674/2675 to Human FcγRs

Aim

The aim was to determine relative binding affinities for 2674/2675 to human FcγRs using the Octet platform.

Materials and Methods

FcγR affinity was determined using the Octet RED96 platform equipped with Anti-Human Fab-CH1 (FAB2G) sensor tips (ForteBio). Antibodies were diluted to 200 nM in 1× Kinetics Buffer (ForteBio) and loaded to a set of 8 parallel sensors for 300 seconds to reach an immobilization response of >1.5 nm. The immobilized antibodies were then assayed against 7 2-fold dilutions of FcγRs, starting at 100 nM. One immobilized sensor was assayed against 1× Kinetics Buffer for referencing and the entire assay was repeated without immobilization of antibodies to allow for double referencing. FcγRs included were obtained from R&D Systems (human FcγRI, #1257-FC-050; human FcγRIIa, #1330-CD-050; human FcγRIIb, #1460-CD-050; human FcγRIIIa (V158), #4325-FC-050; human FcγRIIIa (F158), #8894-FC-050). Binding to FcγRs was carried out for 60 seconds, followed by dissociation for 60 seconds in 1× Kinetics Buffer and regeneration of sensor tips using 10 mM glycine, pH 1.7. Data generated was referenced by standard double referencing, the baseline was aligned with the y-axis, inter-step correlation by alignment against dissociation was performed and the data was smoothed by a Savitzky-Golay filtering in the data analysis software (v.9.0.0.14). The processed data was fitted using a 1:1 Langmuir binding model with $X^2$ as a measurement of fitting accuracy. To improve curve fitting quality of dissociation curves generated against FcγRs with very fast dissociation rates, only the initial 10 seconds of the dissociation curves were included in the curve fitting.

Results and Conclusions

The binding affinities human FcγRs of 2674/2675 and REF antibodies are presented in Table 13. 2674/2675 has a stronger binding to human FcγRI than all other assayed Fc receptors, as expected of an IgG4 antibody binding to the high affinity receptor FcγRI. 2674/2675 has a comparable binding to human FcγRs as REF1 antibody.

TABLE 13

Determined binding affinities, KD (M), for 2674/2675 and REF antibodies to human FcγRs

| KD (M) | FcγRI | FcγRIIa | FcγRIIb | FcγRIIIa 176V | FcγRIIIa 176F |
|---|---|---|---|---|---|
| 2674/2675 | 2.11E−09 | 1.00E−06 | 7.79E−07 | <det. limit | <det. limit |
| REF1 | 1.88E−09 | 6.74E−07 | 6.23E−07 | <det. limit | <det. limit |
| REF2 | <det. limit | 5.87E−07 | 2.70E−06 | <det. limit | <det. limit |

Example 18—Binding of 2674/2675 to Human and Cynomolgus CD137 Measured by FACS The aim of this study was to determine the binding to human and cynomolgus CD137.

Material and Methods

Binding and EC50 was determined using flow cytometric of CHO cells transfected with human CD137, cynomolgus CD137 or empty vector. The extracellular part of human or cynomolgus CD137 was fused to the transmembrane and intracellular part of human CD40 and cloned into pcDNA3.1. The vector was subsequently stably transfected into CHO cells. Expression of CD137 was confirmed by flow cytometry using CD137 antibody (human CD137-PE, BD Biosciences #555956) for 30 min at 4° C. CD137-transfected and empty vector-transfected cells were incubated with CD137 antibodies for at least 1 h at 4° C. to saturate the binding. In order to minimize antibody internalization, 0.05% sodium azide was used in the incubation buffer and all work was performed on ice. The CD137 antibodies were detected using PE-conjugated anti-hIgG antibody (109-115-098, Jackson Immunoresearch laboratories), incubated for 30 min at 4° C. Directly after staining the cells were fixed with a paraformaldehyde solution (10× concentrate BD CellFIX, BD biosciences #340181). Cells were analyzed by flow cytometry using FACSVerse (BD Biosciences). The median fluorescence intensity (MFI) for each sample was determined and the dose response data was analysed using Graph Pad Prism.

MFI data was normalized for each antibody, where 0% is defined as the lowest value and 100% is the highest value in the dose titration for each antibody. EC50 and 95% confidence interval were calculated with Graph Pad Prism based on data from the two experiments (non-linear regression (curve fit), constraints set to 0 and 100).

Results and Conclusion

Figure 8:
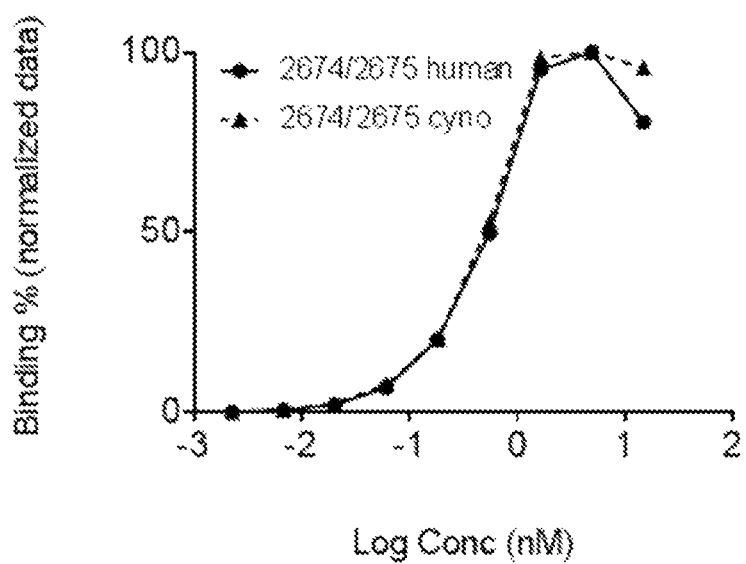
FIG. 8 shows binding of 2674/2675 to human and cynomolgus CD137.

2674/2675 have a comparable binding to human CD137 as the parental clone 1630 and the REF1 and REF2 CD137 mAbs FIG. 8 and Table 14. 2674/2675 and 1630/1631 have comparable binding to cynomolgus CD137 while REF1 does not bind to cynomolgus CD137 at all.

TABLE 14

95% confidence intervals for the EC50 of each CD137 antibody determined as an average from 3 experiments of normalized data.

|  | Hu CD137 EC50 (nM) 95% conf interval | Cy CD137 EC50 (nM) 95% conf interval |
| --- | --- | --- |
| 2674/2675 | 0.26-0.37 | 0.46-0.77 |
| 1630/1631 | 0.23-0.34 | 0.55-0.87 |
| REF1 | 0.33-0.73 | n.d. |
| REF2 | 0.16-0.27 | 0.41-0.56 |

Nd: Not detectable

Example 19-CD137 Reporter Assay with FcγR Expressing Cells for Crosslink of CD137 mAb Aim and Background Functional evaluation of 2674/2675 with the parental clone 1630/1631 in the CD137 reporter assay when crosslinking CD137 mAbs with FcγR transfected CHO cells.

Materials and Methods

CHO-cells transfected with human FcγRI, FcγRIIa R131, FcγRIIb or empty vector (pcDNA3.1) were used for crosslinking. FcγR genes were cloned into pcDNA3.1. The vector was subsequently stably transfected into CHO cells. The expression of FcγRs was confirmed by staining with commercial antibody targeting CD32 or CD64.

Agonistic function of the CD137 mAbs was evaluated using a CD137 reporter assay (Promega, CD137 Bioassay Kit CS196005). The assay was performed according to the manufacturer's protocol. In brief, FcγR transfected CHO cells and titrating concentrations of CD137 mAbs were diluted in RPMI containing 10% FCS and added to the assay plates before the addition of CD137 (Jurkat/CD137 cells) reporter cells. The assay plate was incubated for 6 h at 37° C. until addition of Bio-Glo™ Luciferase Assay Detection and plate read in the BMG reader.

Results and Conclusions

Figure 9:
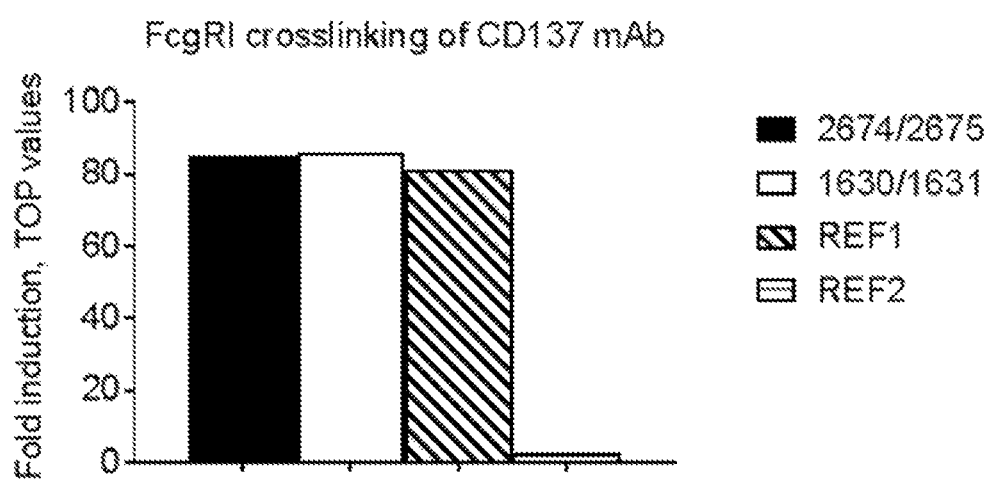
FIG. 9 shows crosslinking of 2674/2675 and parental clone 1630/1631 with FcγRI transfected CHO cells in the CD137 reporter assay.
Figure 10:
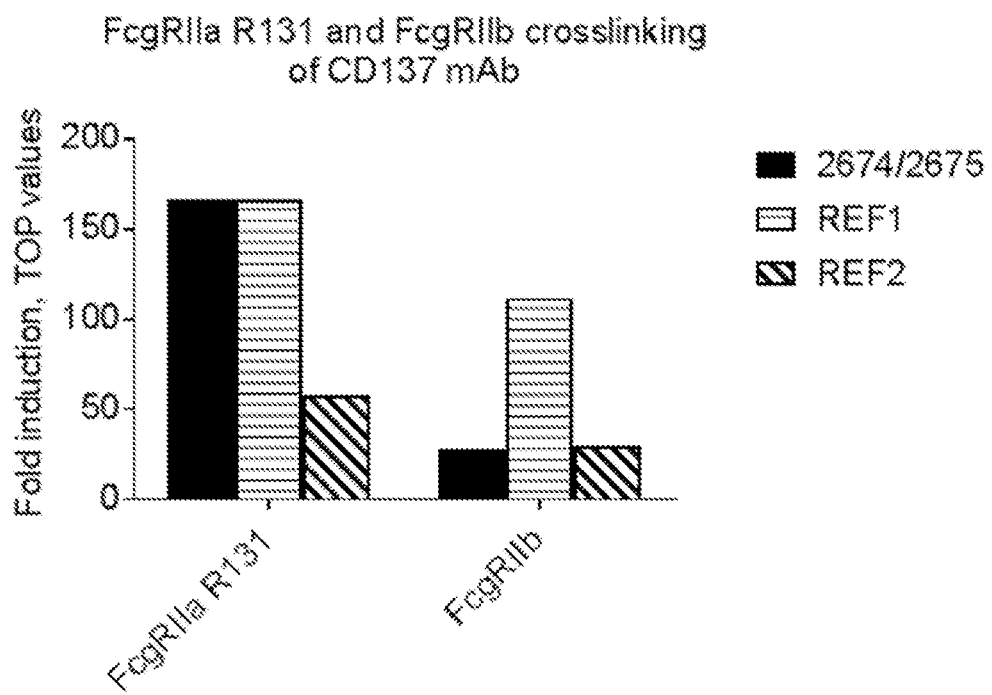
FIG. 10 shows crosslinking of 2674/2675 and parental clone 1630/1631 with FcγRIIa R131 and FcγRIIb in the CD137 reporter assay.
Figure 11:
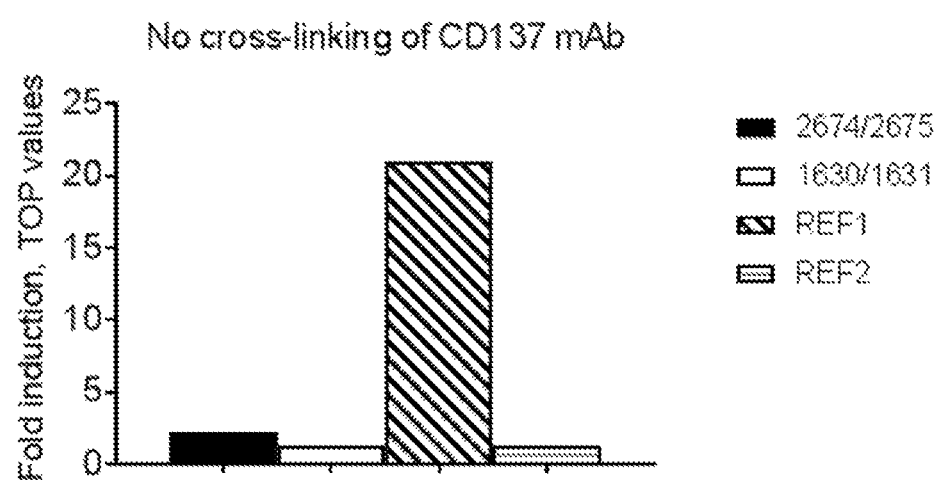
FIG. 11 shows CHO cells transfected with empty vector (pcDNA3.1), used to determine crosslinking independent activation in the reporter cell line.

Crosslinking of the CD137 mAbs in the CD137 reporter assay with FcγRI transfected CHO cells demonstrates that 2674/2675 as well as the parental clone 1630/1631 induces a CD137 dependent activation of NF-κB in the reporter cell line (FIG. 9). It can be concluded that if the CD137 antibody is crosslinking dependent, binding affinities to FcγRI, FcγRIIa R131 and FcγRIIb (shown in previous example) correlate well with the agonistic activity induced in the CD137 reporter assay after FcγR crosslinking (FIG. 10). FcγR cross-linking independent activation of REF1 but not of 2674/2675, 1630/1631 or REF2 was determined using CHO cells transfected with empty vector (FIG. 11).

Example 20—CD8+ T Cell Agonist Assay with FcγRI Expressing CHO Cells for Crosslinking of CD137 Antibodies Aim and Background Functional evaluation of 2674/2675 with the parental clone 1630/1631 in a CD8+ T cell agonist assay when crosslinking the CD137 mAbs with FcγRI expressing cells.

Materials and Methods

CHO-cells transfected with human FcγRI were used for crosslinking. The FcγRI gene were cloned into pcDNA3.1. The vector was subsequently stably transfected into CHO cells. The expression of FcγRI was confirmed by staining with commercial antibody targeting CD64.

Agonistic activity of CD137 antibodies was evaluated in a T cell assay based on primary human CD8+ T cells. Briefly, CD8+ T cells were separated from human peripheral blood mononuclear cells by MACS separation (Miltenyi #130-096-495) according to the manufacturer's protocol. Cells were incubated in 96-well microtiter plates (NuncThermo Scientific #268200) pre-incubated with CHO cells transfected with FcγRI and incubated with tosyl beads coated with anti-CD3 antibody (clone OKT3, Affymetrix eBioscience #16-0037) and titrated concentrations of the CD137 antibody to be tested. Following 72-hour incubation, culture medium was harvested and IFN-γ levels were determined by ELISA (BD #555142).

Each clone was analyzed in at least 5 donors and compared to the reference CD137 antibody REF2. Due to large intra-donor variations, IFN-γ levels were normalized with 2674/2675 within each donor for comparison.

Results and Conclusions

Figure 12:
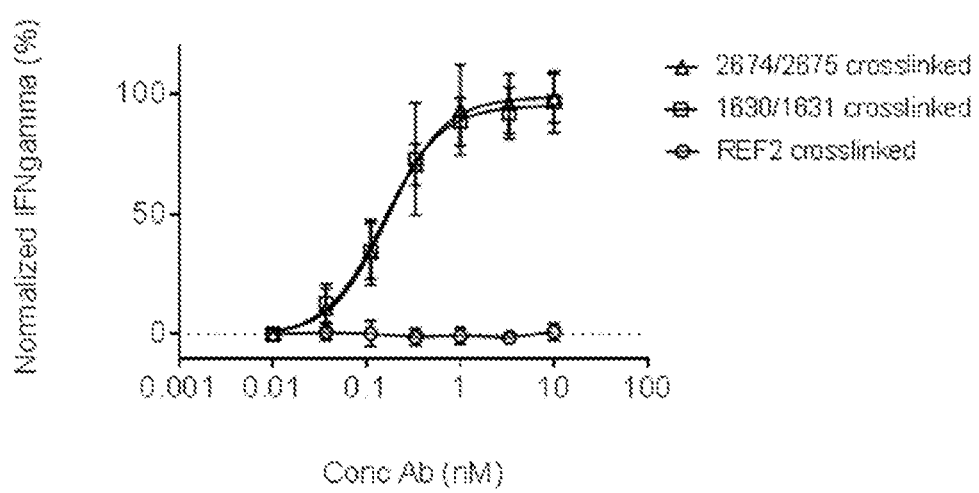
FIG. 12 shows IFN-γ production of CD8+ T cells after stimulation with CD137 mAbs when crosslinked with FcγRI transfected CHO cells. Summary of IFN-γ response normalized against 2674/2675 agonist response in a CD8+ T cell agonist assay (n=5).

Crosslinking with FcγRI expressing CHO cells in the CD8 T cell agonist assay of the CD137 mAbs 2674/2675 and the parental clone 1630/1631, but not REF2, induces T cell activation, measured as an increase in IFN-γ production after 72 h (FIG. 12). IgG binding affinities to FcγRs of 2674/2675, 1630/1631 and REF2 have been determined and was shown in a previous example. It can be concluded that IgG binding affinity to FcγR correlate with the agonistic activity induced in the CD8+ T cells.

Example 21—In Vivo Anti-Tumour Effect in HT-29 Colon Cancer Model

Aim

The anti-tumour effect of 2674/2675 was investigated using hPBMC humanized immunodeficient mice and subcutaneous tumour models of HT-29 colon carcinoma.

Material and Methods

Leukocyte concentrates were obtained from Lund University Hospital. Female SCID-Beige mice (7-8w) from Taconic's Denmark were used in the experiments. All experiments were done by approval of Malmö/Lund ethical committee.

HT-29 colon cancer was obtained from ATCC and cultivated according to ATCC recommendations. The HT-29 cell line growing in log phase was injected subcutaneously ($4\times10^6$ cells in 200 µL at day 0 (D0)). Human PBMC ($10\times10^6$ in 100 µL) isolated from leukocyte concentrates was injected intraperitoneally at the same day. Intraperitoneal treatments (100 µg) were done twice weekly for three weeks starting at day 7.

Tumour was measured with a calliper in width, length and height of which the tumour volume calculated (w/2×l/2×h/2×pi×(4/3)). The animals were terminated before the tumour volume reached 2 cm³, at wounding, or affected health of the mice.

Results and Conclusion

2674/2675 demonstrated anti-tumor efficacy in humanized mouse models in comparison to the vehicle group. The percentage of tumour volume inhibition ranged from 0-35% with 2674/2675 between days 19 and 28 (Table 15).

In conclusion, the anti-tumour effect of 2674/2675 was investigated using hPBMC humanized immunodeficient mice and subcutaneous tumour models of HT-29 colon carcinoma. 2674/2675 demonstrated tumour volume inhibition.

TABLE 15

Percent tumour inhibition

| Day after tumour inoculation | Tumour growth inhibition (tumour volume) compared to vehicle (%) |
|---|---|
| D19 | 9.4 |
| D21 | 24.0 |
| D24 | 27.4 |
| D26 | 24.7 |
| D28 | 35.1 |

Example 22—Gene Expression Analyses of FcγR and CD137 Co Expression in Human Tumor Tissue Aim Assessing the gene expression of various Fcγ receptors, as well as CD137, in a wide range of human cancers using a curated and quality-controlled database of microarray and RNA-seq datasets.

Methods

Figure 13:
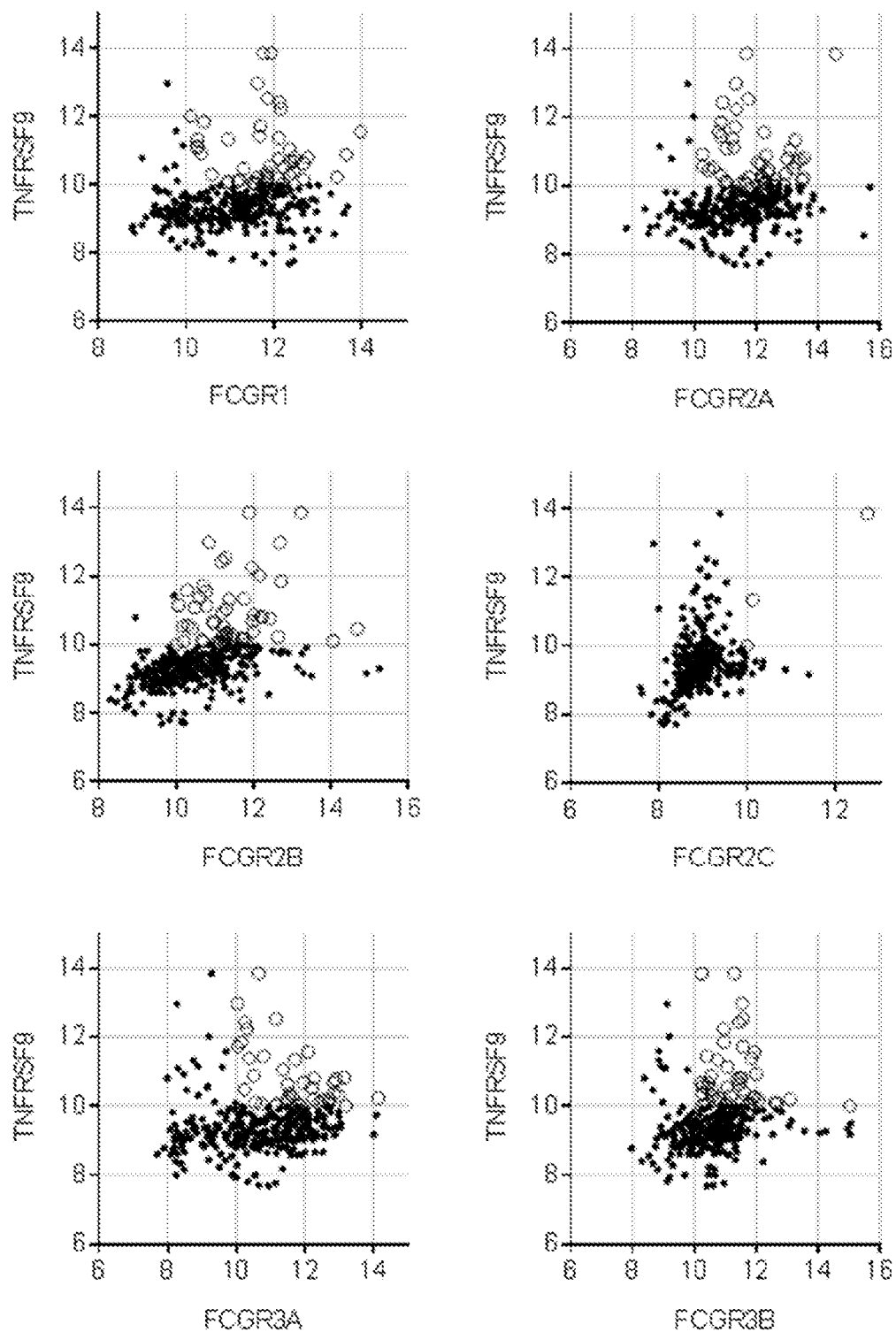
FIG. 13 shows Dot plots showing the correlation between the mean expression values of Fcγ receptor (X axes) and TNFRSF9 (CD137, Y axes) for various human cancers. Cancers with an above average expression (mean expression level 10) of both Fcγ receptor and CD137 have been highlighted as clear symbols.

Mean expression values for FcγRI, FcγRIIa, FcγRIIb, FcγRIIc, FcγRIIIa, FcγRIIIb and CD137 were obtained by performing gene expression profiling using Genevestigator, a curated and quality-controlled database of RNA microarray studies for human tissues (Hruz et al. 2008, *Adv Bioinformatics* 2008:420747, the disclosures of which are incorporated herein by reference). Correlation plots were obtained by plotting the mean expression values of the various Fcγ receptor genes versus CD137 (FIG. 13). Cancers displaying an above average expression (mean expression level ≥10) of both Fcγ receptor and CD137 were identified and the top 10 solid tumor types and hematological malignancies are presented in Table 16 and Table 17, respectively.

Results and Conclusions

Several human tumors with a high expression of Fcγ receptors and an above average expression of CD137 were identified using this method. The tables below provide an example of indications that could be highly sensitive to the antibody defined in this invention. This approach could be used to identify patient cohorts or individual patients that may benefit from treatment with agonistic CD137 antibodies. In fact, this type of approach could be used to identify patients on an individual level that may benefit from the treatment. One could also envisage other methods being used to molecularly characterize the tumor, such as next generation sequencing or methods based on protein analysis such as immunohistochemistry, flow cytometry or proteomic approaches.

TABLE 16

Mean expression values of solid human tumors with an above average expression (mean expression level ≥10) of both Fcγ receptor and CD137 (TNFRSF9), as identified in FIG. 13. The ten tumors with the highest expression of the six Fcγ receptors are shown.

| Cancers with cells expressing FcγRIA and TNFRSF9 | FcγRIA (Mean expression level) | TNFRSF9 (Mean expression level) |
|---|---|---|
| fibrous histiocytoma, malignant, metastatic | 13.43 | 10.22 |
| adenosquamous carcinoma | 12.78 | 10.80 |
| undifferentiated sarcoma | 12.67 | 10.16 |
| clear cell adenocarcinoma, NOS, metastatic | 12.66 | 10.62 |
| acinar cell carcinoma | 12.47 | 10.82 |
| dedifferentiated liposarcoma | 12.45 | 10.67 |
| renal cell carcinoma, unstated behavior | 12.44 | 10.38 |
| intraductal micropapillary carcinoma | 12.36 | 10.68 |
| fibrous histiocytoma, malignant | 12.35 | 11.05 |
| large cell neuroendocrine carcinoma | 12.35 | 10.29 |

| Cancers with cells expressing FcγRIIA and TNFRSF9 | FcγRIIA (Mean expression level) | TNFRSF9 (Mean expression level) |
|---|---|---|
| Langerhans-cell histiocytosis, unifocal | 14.58 | 13.85 |
| acinar cell carcinoma | 13.55 | 10.82 |
| fibrous histiocytoma, malignant, metastatic | 13.54 | 10.22 |
| undifferentiated sarcoma | 13.48 | 10.16 |
| adenocarcinoma with mixed subtypes | 13.43 | 10.77 |
| dedifferentiated liposarcoma | 13.32 | 10.67 |
| undifferentiated sarcoma | 13.22 | 10.52 |
| fibrous histiocytoma, malignant | 13.10 | 11.05 |
| adenosquamous carcinoma | 13.01 | 10.80 |
| dedifferentiated liposarcoma | 12.95 | 10.36 |

| Cancers with cells expressing FcγRIIB and TNFRSF9 | FcγRIIB (Mean expression level) | TNFRSF9 (Mean expression level) |
|---|---|---|
| Langerhans-cell histiocytosis, unifocal | 13.23 | 13.85 |
| fibrous histiocytoma, malignant, metastatic | 12.64 | 10.22 |
| adenocarcinoma with mixed subtypes | 12.42 | 10.77 |
| adenosquamous carcinoma | 12.22 | 10.80 |
| acinar cell carcinoma | 12.19 | 10.82 |
| Hodgkin's disease, NOS | 12.01 | 10.88 |
| renal cell carcinoma, unstated behavior | 12.00 | 10.38 |
| dedifferentiated liposarcoma | 11.98 | 10.67 |
| papillary adenocarcinoma, NOS | 11.81 | 10.02 |
| undifferentiated sarcoma | 11.76 | 10.16 |

| Cancers with cells expressing FcγRIIC and TNFRSF9 | FcγRIIC (Mean expression level) | TNFRSF9 (Mean expression level) |
|---|---|---|
| Langerhans-cell histiocytosis, unifocal | 12.72 | 13.85 |

| Cancers with cells expressing FcγRIIIA and TNFRSF9 | FcγRIIIA (Mean expression level) | TNFRSF9 (Mean expression level) |
|---|---|---|
| fibrous histiocytoma, malignant, metastatic | 14.14 | 10.22 |
| acinar cell carcinoma | 13.14 | 10.82 |
| large cell neuroendocrine carcinoma | 12.97 | 10.29 |
| adenocarcinoma with mixed subtypes | 12.91 | 10.77 |
| renal cell carcinoma, unstated behavior | 12.85 | 10.38 |
| intraductal micropapillary carcinoma, NOS | 12.83 | 10.68 |
| carcinoma, NOS | 12.70 | 10.19 |
| carcinoma, NOS | 12.68 | 10.06 |
| undifferentiated sarcoma | 12.52 | 10.16 |
| carcinoma, NOS | 12.42 | 10.10 |

TABLE 16-continued

Mean expression values of solid human tumors with an above average expression (mean expression level ≥10) of both Fcγ receptor and CD137 (TNFRSF9), as identified in FIG. 13. The ten tumors with the highest expression of the six Fcγ receptors are shown.

| Cancers with cells expressing FcγRIIIB and TNFRSF9 | FcγRIIIB (Mean expression level) | TNFRSF9 (Mean expression level) |
|---|---|---|
| carcinoma, NOS | 13.09 | 10.19 |
| carcinoma, NOS | 12.66 | 10.06 |
| carcinoma, NOS | 12.61 | 10.10 |
| tubular adenocarcinoma | 12.06 | 10.18 |
| carcinoma, NOS, micro-dissected | 12.00 | 10.92 |
| adenocarcinoma, intestinal type | 11.97 | 10.26 |
| fibrous histiocytoma, malignant, metastatic | 11.89 | 10.22 |
| neoplasm, malignant | 11.81 | 10.05 |
| adenocarcinoma, NOS | 11.74 | 10.06 |
| renal cell carcinoma, unstated behavior | 11.61 | 10.38 |

TABLE 17

Mean expression values of hematological malignancies with an above average expression (mean expression level ≥10) of both Fcγ receptor and CD137, as identified in FIG. 13. The ten malignancies with the highest expression of the six Fcγ receptors are shown.

| Cancers with cells expressing FcγRIA and TNFRSF9 | FcγRIA (Mean expression level) | TNFRSF9 (Mean expression level) |
|---|---|---|
| (extranodal) NK/T-cell lymphoma, nasal and nasal-type | 13.97 | 11.56 |
| Hodgkin's disease, NOS | 13.65 | 10.88 |
| malignant lymphoma, large B-cell, diffuse | 12.15 | 12.23 |
| primary mediastinal B-cell lymphoma | 12.13 | 12.43 |
| anaplastic large cell lymphoma, T-cell and Null cell type (ALCL), unstated behavior | 12.11 | 11.38 |
| angioimmunoblastic T-cell lymphoma | 11.93 | 13.85 |
| mature T-cell lymphoma, NOS | 11.86 | 12.53 |
| mature T-cell lymphoma, NOS, unstated behavior | 11.69 | 11.72 |
| anaplastic large cell lymphoma, T-cell and Null cell type (ALCL) | 11.67 | 11.43 |
| angioimmunoblastic T-cell lymphoma, unstated behavior | 11.63 | 12.98 |

| Cancers with cells expressing FcγRIIA and TNFRSF9 | FcγRIIA (Mean expression level) | TNFRSF9 (Mean expression level) |
|---|---|---|
| mycosis fungoides | 13.27 | 11.34 |
| Hodgkin's disease, NOS | 12.33 | 10.88 |
| (extranodal) NK/T-cell lymphoma, nasal and nasal-type | 12.26 | 11.56 |
| mature T-cell lymphoma, NOS | 11.76 | 12.53 |
| angioimmunoblastic T-cell lymphoma | 11.69 | 13.85 |
| malignant lymphoma, large B-cell, diffuse | 11.37 | 12.23 |
| angioimmunoblastic T-cell lymphoma, unstated behavior | 11.34 | 12.98 |
| mature T-cell lymphoma, NOS, unstated behavior | 11.33 | 11.72 |
| adult T-cell leukemia/lymphoma (HTLV-1 positive), unstated behavior | 11.28 | 11.13 |
| anaplastic large cell lymphoma, T-cell and Null cell type (ALCL), unstated behavior | 11.23 | 11.38 |

| Cancers with cells expressing FcγRIIB and TNFRSF9 | FcγRIIB (Mean expression level) | TNFRSF9 (Mean expression level) |
|---|---|---|
| chronic lymphocytic B-cell leukemia, unstated behavior, micro-dissected | 14.69 | 10.46 |
| mantle cell lymphoma | 14.06 | 10.11 |

TABLE 17-continued

Mean expression values of hematological malignancies with an above average expression (mean expression level ≥10) of both Fcγ receptor and CD137, as identified in FIG. 13. The ten malignancies with the highest expression of the six Fcγ receptors are shown.

| | | |
|---|---|---|
| (extranodal) marginal zone B-cell lymphoma, NOS | 12.73 | 11.85 |
| malignant lymphoma, nodular, NOS, unstated behavior | 12.69 | 12.97 |
| malignant lymphoma, nodular, NOS | 12.16 | 12.02 |
| Hodgkin's disease, NOS | 12.01 | 10.88 |
| malignant lymphoma, large B-cell, diffuse | 11.97 | 12.23 |
| angioimmunoblastic T-cell lymphoma | 11.89 | 13.85 |
| mycosis fungoides | 11.76 | 11.34 |
| Hodgkin's disease, NOS, micro-dissected | 11.38 | 11.32 |

| Cancers with cells expressing FcγRIIC and TNFRSF9 | FcγRIIC (Mean expression level) | TNFRSF9 (Mean expression level) |
|---|---|---|
| juvenile myelomonocytic leukemia | 10.00 | 10.00 |

| Cancers with cells expressing FcγRIIIA and TNFRSF9 | FcγRIIIA (Mean expression level) | TNFRSF9 (Mean expression level) |
|---|---|---|
| juvenile myelomonocytic leukemia | 13.19 | 10.00 |
| (extranodal) NK/T-cell lymphoma, nasal and nasal-type | 12.09 | 11.56 |
| mycosis fungoides | 11.71 | 11.34 |
| mature T-cell lymphoma, NOS | 11.16 | 12.53 |
| anaplastic large cell lymphoma, T-cell and Null cell type (ALCL) | 10.80 | 11.43 |
| angioimmunoblastic T-cell lymphoma | 10.65 | 13.85 |
| Hodgkin's disease, NOS | 10.51 | 10.88 |
| anaplastic large cell lymphoma, T-cell and Null cell type (ALCL), unstated behavior | 10.38 | 11.38 |
| malignant lymphoma, large B-cell, diffuse | 10.31 | 12.23 |
| primary mediastinal B-cell lymphoma | 10.26 | 12.43 |

| Cancers with cells expressing FcγRIIIB and TNFRSF9 | FcγRIIIB (Mean expression level) | TNFRSF9 (Mean expression level) |
|---|---|---|
| juvenile myelomonocytic leukemia | 15.03 | 10.00 |
| (extranodal) NK/T-cell lymphoma, nasal and nasal-type | 11.95 | 11.56 |
| anaplastic large cell lymphoma, T-cell and Null cell type (ALCL), unstated behavior | 11.85 | 11.38 |
| mature T-cell lymphoma, NOS | 11.57 | 12.53 |
| mature T-cell lymphoma, NOS, unstated behavior | 11.56 | 11.72 |
| angioimmunoblastic T-cell lymphoma, unstated behavior | 11.54 | 12.98 |
| primary mediastinal B-cell lymphoma | 11.44 | 12.43 |
| angioimmunoblastic T-cell lymphoma | 11.30 | 13.85 |
| adult T-cell leukemia/lymphoma (HTLV-1 positive), unstated behavior | 11.08 | 11.13 |
| (extranodal) marginal zone B-cell lymphoma, NOS | 10.95 | 11.85 |

REFERENCES

Almeida J, Bueno C, Alguero M C et al. Comparative analysis of the morphological, cytochemical, immunophenotypical, and functional characteristics of normal human peripheral blood lineage (−)/CD16(+)/HLA-DR (+)/CD14(−/lo) cells, CD14(+) monocytes, and CD16(−) dendritic cells. Clin Immunol. 2001 September; 100(3): 325-38.

Akhmetzyanova, I., Zelinskyy, G., Littwitz-Salomon, E., Malyshkina, A., Dietze, K. K., Streeck, H., Brandau, S., and Dittmer, U. (2016) CD137 Agonist Therapy Can Reprogram Regulatory T Cells into Cytotoxic CD4+ T Cells with Antitumour Activity. J. Immunol. 196, 484-492.

Ascierto, P. A., Simeone, E., Sznol, M., Fu, Y. X., and Melero, I. (2010) Clinical experiences with anti-CD137 and anti-PD1 therapeutic antibodies. Semin. Oncol. 37, 508-516.

Baessler T, Charton J E, Schmiedel B J, Grünebach F, Krusch M, Wacker A, Rammensee H G, Salih H R. CD137 ligand mediates opposite effects in human and mouse NK cells and impairs NK-cell reactivity against human acute myeloid leukemia cells. Blood. 2010 Apr. 15; 115(15):3058-69. doi: 10.1182/blood-2009-06-227934. Erratum in: Blood. 2010 Dec. 23; 116(26):6152. PubMed PMID: 20008791.

Bartkowiak, T. and Curran, M. A. (2015) 4-1BB Agonists: Multi-Potent Potentiators of Tumour Immunity. Front Oncol. 5, 117.

Bronte V, Brandau S, Chen S H et al. Recommendations for myeloid-derived suppressor cell nomenclature and characterization standards. Nat Commun. 2016 Jul. 6; 7:12150.

Bruhns P, Iannascoli B, England P et al. Specificity and affinity of human Fcgamma receptors and their polymorphic variants for human IgG subclasses. Blood. 2009 Apr. 16; 113(16):3716-25.

Bulliard Y, Jolicoeur R, Zhang J, Dranoff G, Wilson N S, Brogdon J L. OX40 engagement depletes intratumoural Tregs via activating FcγRs, leading to antitumour efficacy. Immunol Cell Biol. 2014 July; 92(6):475-80. doi: 10.1038/icb.2014.26. PubMed PMID: 24732076.

Cavnar M J, Zeng S, Kim T S et al. KIT oncogene inhibition drives intratumoral macrophage M2 polarization. J Exp Med. 2013 Dec. 16; 210(13):2873-86.

Cheeseman H M, Carias A M, Evans A B et al. Expression Profile of Human Fc Receptors in Mucosal Tissue: Implications for Antibody-Dependent Cellular Effector Functions Targeting HIV-1 Transmission. PLoS One. 2016 May 10; 11(5):e0154656.

Curran, M. A., Kim, M., Montalvo, W., Al-Shamkhani, A., and Allison, J. P. (2011) Combination CTLA-4 blockade and 4-1BB activation enhances tumour rejection by increasing T-cell infiltration, proliferation, and cytokine production. PLoS. ONE. 6, e19499.

Dubrot, J., Milheiro, F., Alfaro, C., Palazon, A., Martinez-Forero, I., Perez-Gracia, J. L., Morales-Kastresana, A., Romero-Trevejo, J. L., Ochoa, M. C., Hervas-Stubbs, S., Prieto, J., Jure-Kunkel, M., Chen, L., and Melero, I. (2010) Treatment with anti-CD137 mAbs causes intense accumulations of liver T cells without selective antitumour immunotherapeutic effects in this organ. Cancer Immunol. Immunother. 59, 1223-1233.

Gauttier, V., Judor, J. P., Le, G., V, Cany, J., Ferry, N., and Conchon, S. (2014) Agonistic anti-CD137 antibody treatment leads to antitumour response in mice with liver cancer. Int. J. Cancer 135, 2857-2867.

Gray, J. C., French, R. R., James, S., Al-Shamkhani, A., Johnson, P. W., and Glennie, M. J. (2008) Optimising anti-tumour CD8 T-cell responses using combinations of immunomodulatory antibodies. Eur. J. Immunol. 38, 2499-2511.

Guilliams M, Bruhns P, Saeys Y et al. The function of Fcγ receptors in dendritic cells and macrophages. Nat Rev Immunol. 2014 February; 14(2):94-108.

Guo, Z., Cheng, D., Xia, Z., Luan, M., Wu, L., Wang, G., and Zhang, S. (2013) Combined TIM-3 blockade and CD137 activation affords the long-term protection in a murine model of ovarian cancer. J. Transl. Med. 11, 215.

Elliott L A, Doherty G A, Sheahan K et al. Human Tumor-Infiltrating Myeloid Cells: Phenotypic and Functional Diversity. Front Immunol. 2017 Feb. 6; 8:86

Eruslanov E B, Bhojnagarwala P S, Quatromoni J G et al. Tumor-associated neutrophils stimulate T cell responses in early-stage human lung cancer. J Clin Invest. 2014 December; 124(12): 5466-80.

Eruslanov E, Neuberger M, Daurkin I et al. Circulating and tumor-infiltrating myeloid cell subsets in patients with bladder cancer. Int J Cancer. 2012 Mar. 1; 130(5):1109-19.

Griesinger A M, Birks D K, Donson A M et al. Characterization of distinct immunophenotypes across pediatric brain tumor types. J Immunol. 2013 Nov. 1; 191(9):4880-8.

Grugan K D, McCabe F L, Kinder M et al. Tumor-associated macrophages promote invasion while retaining Fc-dependent anti-tumor function. J Immunol. 2012 Dec. 1; 189 (11):5457-66.

Hansen B D, Schmidt H, von der Maase H et al. Tumour-associated macrophages are related to progression in patients with metastatic melanoma following interleukin-2 based immunotherapy. Acta Oncol. 2006; 45(4): 400-5.

Hogarth P M, Pietersz G A. Fc receptor-targeted therapies for the treatment of inflammation, cancer and beyond. Nat Rev Drug Discov. 2012 Mar. 30; 11(4):311-31.

Holbrook E. Kohrt, A. Dimitrios Colevas, Roch Houot,1,2,3 Kipp Weiskopf, Matthew J. Goldstein, Peder Lund, Antonia Mueller, Idit Sagiv-Barfi, Aurelien Marabelle, Ruth Lira, Emily Troutner, Lori Richards, 1 Amanda Rajapaska, Jonathan Hebb, Cariad Chester, Erin Waller, Anton Ostashko, Wen-Kai Weng, Lieping Chen, Debra Czerwinski, Yang-Xin Fu, John Sunwoo, and Ronald Levy. Targeting CD137 enhances the efficacy of cetuximab. The Journal of Clinical Investigation Volume 124 Number 6 June 2014

Horton H M, Bernett M J, Peipp M, Pong E, Karki S, Chu S Y, Richards J O, Chen H, Repp R, Desjarlais J R, Zhukovsky E A. Fc-engineered anti-CD40 antibody enhances multiple effector functions and exhibits potent in vitro and in vivo antitumour activity against hematologic malignancies. Blood. 2010 Oct. 21; 116(16):3004-12. doi: 10.1182/blood-2010-01-265280. PubMed PMID: 20616215.

Hruz T, Laule O, Szabo G, Wessendorp F, Bleuler S, Oertle L, Widmayer P, Gruissem W, Zimmermann P: Genevestigator v3: a reference expression database for the meta-analysis of transcriptomes. *Adv Bioinformatics* 2008, 2008:420747.

Hu W, Li X, Zhang C et al. Tumor-associated macrophages in cancers. Clin Transl Oncol. 2016 March; 18(3):251-8.

Kim, J. A., Averbook, B. J., Chambers, K., Rothchild, K., Kjaergaard, J., Papay, R., and Shu, S. (2001) Divergent effects of 4-1BB antibodies on antitumour immunity and on tumour-reactive T-cell generation. Cancer Res 61, 2031-2037.

Kwong, B., Gai, S. A., Elkhader, J., Wittrup, K. D., and Irvine, D. J. (2013) Localized immunotherapy via liposome-anchored Anti-CD137+IL-2 prevents lethal toxicity and elicits local and systemic antitumour immunity. Cancer Res. 73, 1547-1558.

Lee, H. W., Park, S. J., Choi, B. K., Kim, H. H., Nam, K. O., and Kwon, B. S. (2002) 4-1BB promotes the survival of CD8+ T lymphocytes by increasing expression of Bcl-xL and Bfl-1. J Immunol 169, 4882-4888.

Lee, S. J., Myers, L., Muralimohan, G., Dai, J., Qiao, Y., Li, Z., Mittler, R. S., and Vella, A. T. (2004) 4-1BB and OX40 dual costimulation synergistically stimulate primary specific CD8 T cells for robust effector function. J. Immunol. 173, 3002-3012.

Li Y, Lee P Y, Kellner E S et al. Monocyte surface expression of Fcgamma receptor RI (CD64), a biomarker reflecting type-I interferon levels in systemic lupus erythematosus. Arthritis Res Ther. 2010; 12(3):R90

Li C, Luo X, Lin Y et al. A Higher Frequency of CD14+ CD169+ Monocytes/Macrophages in Patients with Colorectal Cancer. PLoS One. 2015 Oct. 28; 10(10): e0141817.

Li, F. and Ravetch, J. V. (2011) Inhibitory Fcgamma receptor engagement drives adjuvant and anti-tumour activities of agonistic CD40 antibodies. Science 333, 1030-1034.

Lu J, Chu J, Zou Z et al. Structure of FcγRI in complex with Fc reveals the importance of glycan recognition for high-affinity IgG binding. Proc Natl Acad Sci USA. 2015 Jan. 20; 112(3):833-8

McMillin, D. W., Hewes, B., Gangadharan, B., Archer, D. R., Mittler, R. S., and Spencer, H. T. (2006) Complete regression of large solid tumours using engineered drug-resistant hematopoietic cells and anti-CD137 immunotherapy. Hum. Gene Ther 17, 798-806.

Melero, I., Shuford, W. W., Newby, S. A., Aruffo, A., Ledbetter, J. A., Hellstrom, K. E., Mittler, R. S., and Chen, L. (1997) Monoclonal antibodies against the 4-1BB T-cell activation molecule eradicate established tumours. Nat Med 3, 682-685.

Melero I, Daniel Hirschhorn-Cymerman, Aizea Morales-Kastresana, et al. Agonist Antibodies to TNFR Molecules That Costimulate T and NK cells Clin Cancer Res 2013; 19:1044-1053. Published online Mar. 3, 2013.

Melero I, Antonio M. Grimaldi, Jose L. Perez-Gracia, et al. Clinical Development of Immunostimulatory Monoclonal Antibodies and Opportunities for Combination. Clin Cancer Res 2013; 19:997-1008.

Miller, R. E., Jones, J., Le, T., Whitmore, J., Boiani, N., Gliniak, B., and Lynch, D. H. (2002) 4-1BB-specific monoclonal antibody promotes the generation of tumour-specific immune responses by direct activation of CD8 T cells in a CD40-dependent manner. J Immunol 169, 1792-1800.

Morales-Kastresana, A., Sanmamed, M. F., Rodriguez, I., Palazon, A., Martinez-Forero, I., Labiano, S., Hervas-Stubbs, S., Sangro, B., Ochoa, C., Rouzaut, A., Azpilikueta, A., Bolanos, E., Jure-Kunkel, M., Gutgemann, I., and Melero, I. (2013) Combined immunostimulatory monoclonal antibodies extend survival in an aggressive transgenic hepatocellular carcinoma mouse model. Clin. Cancer Res. 19, 6151-6162.

Morimura T, Neuchrist C, Kitz K et al. Monocyte subpopulations in human gliomas: expression of Fc and complement receptors and correlation with tumor proliferation. Acta Neuropathol. 1990; 80(3):287-94.

Norton S E, Dunn E T, McCall J L et al. Gut macrophage phenotype is dependent on the tumor microenvironment in colorectal cancer. Clin Transl Immunology. 2016 Apr. 29; 5(4):e76.

Niu, L., Strahotin, S., Hewes, B., Zhang, B., Zhang, Y., Archer, D., Spencer, T., Dillehay, D., Kwon, B., Chen, L., Vella, A. T., and Mittler, R. S. (2007) Cytokine-mediated disruption of lymphocyte trafficking, hemopoiesis, and induction of lymphopenia, anemia, and thrombocytopenia in anti-CD137-treated mice. J. Immunol. 178, 4194-4213.

Overdijk M B, Verploegen S, Ortiz Buijsse A, Vink T, Leusen J H, Bleeker W K, Parren P W. Crosstalk between human IgG isotypes and murine effector cells. J Immunol. 2012 Oct. 1; 189(7):3430-8. PubMed PMID: 22956577.

Palazón A, Iván Martinez-Forero, Alvaro Teijeira, et al. The HIF-1a Hypoxia Response in Tumour-Infiltrating T Lymphocytes Induces Functional CD137 (4-1BB) for Immunotherapy Cancer Discovery 2012; 2:608-623. Published OnlineFirst Jun. 19, 2012.

Palazón A, Teijeira A, Martinez-Forero I, Hervás-Stubbs S, Roncal C, Peñuelas I, Dubrot J, Morales-Kastresana A, Pérez-Gracia J L, Ochoa M C, Ochoa-Callejero L, Martinez A, Luque A, Dinchuk J, Rouzaut A, Jure-Kunkel M, Melero I. Agonist anti-CD137 mAb act on tumour endothelial cells to enhance recruitment of activated T lymphocytes. Cancer Res. 2011 Feb. 1; 71(3):801-11. doi:10.1158/0008-5472.CAN-10-1733. PubMed PMID: 21266358.

Pan, P. Y., Zang, Y., Weber, K., Meseck, M. L., and Chen, S. H. (2002) OX40 ligation enhances primary and memory cytotoxic T lymphocyte responses in an immunotherapy for hepatic colon metastases. Mol Ther 6, 528-536.

Porembka M R, Mitchem J B, Belt B A et al. Pancreatic adenocarcinoma induces bone marrow mobilization of myeloid-derived suppressor cells which promote primary tumor growth. Cancer Immunol Immunother. 2012 September; 61(9):1373-85.

Pulle, G., Vidric, M., and Watts, T. H. (2006) IL-15-dependent induction of 4-1BB promotes antigen-independent CD8 memory T cell survival. J Immunol 176, 2739-2748.

Rabu, C., Quemener, A., Jacques, Y., Echasserieau, K., Vusio, P., and Lang, F. (2005) Production of recombinant human trimeric CD137L (4-1BBL). Cross-linking is essential to its T cell co-stimulation activity. J Biol Chem 280, 41472-41481.

Roussel M, Ferrell P B Jr, Greenplate A R et al. Mass cytometry deep phenotyping of human mononuclear phagocytes and myeloid-derived suppressor cells from human blood and bone marrow. J Leukoc Biol. 2017 August; 102(2):437-447

Sallin, M. A., Zhang, X., So, E. C., Burch, E., Cai, L., Lin, W., Chapoval, A. I., and Strome, S. E. (2014) The anti-lymphoma activities of anti-CD137 monoclonal antibodies are enhanced in FcgammaRIII (−/−) mice. Cancer Immunol. Immunother. 63, 947-958.

Sanmamed, M. F., Pastor, F., Rodriguez, A., Perez-Gracia, J. L., Rodriguez-Ruiz, M. E., Jure-Kunkel, M., and Melero, I. (2015) Agonists of Co-stimulation in Cancer Immunotherapy Directed Against CD137, OX40, GITR, CD27, CD28, and ICOS. Semin. Oncol. 42, 640-655.

Shuford, W. W., Klussman, K., Tritchler, D. D., Loo, D. T., Chalupny, J., Siadak, A. W., Brown, T. J., Emswiler, J., Raecho, H., Larsen, C. P., Pearson, T. C., Ledbetter, J. A., Aruffo, A., and Mittler, R. S. (1997) 4-1BB costimulatory signals preferentially induce CD8+ T cell proliferation and lead to the amplification in vivo of cytotoxic T cell responses. J Exp. Med 186, 47-55.

So, T., Lee, S. W., and Croft, M. (2008) Immune regulation and control of regulatory T cells by OX40 and 4-1BB. Cytokine Growth Factor Rev. 19, 253-262.

Solito S, Marigo I, Pinton L et al. Myeloid-derived suppressor cell heterogeneity in human cancers. Ann N Y Acad Sci. 2014 June; 1319:47-65.

Stewart R, Hammond S, Oberst M, Wilkinson R. (2014) The role of Fc gamma receptors in the activity of immunomodulatory antibodies for cancer. J Immunother. 2:29

St Rose, M. C., Taylor, R. A., Bandyopadhyay, S., Qui, H. Z., Hagymasi, A. T., Vella, A. T., and Adler, A. J. (2013) CD134/CD137 dual costimulation-elicited IFN-gamma maximizes effector T-cell function but limits Treg expansion. Immunol. Cell Biol. 91, 173-183.

Sun Y, Subudhi S K, Fu Y X. Co-stimulation agonists as a new immunotherapy for autoimmune diseases. Trends Mol Med. 2003 November; 9(11):483-9. Review. PubMed PMID: 14604826.

Taraban, V. Y., Rowley, T. F., O'Brien, L., Chan, H. T., Haswell, L. E., Green, M. H., Tutt, A. L., Glennie, M. J., and Al-Shamkhani, A. (2002) Expression and costimulatory effects of the TNF receptor superfamily members CD134 (OX40) and CD137 (4-1BB), and their role in the generation of anti-tumour immune responses. Eur J Immunol 32, 3617-3627.

Uno, T., Takeda, K., Kojima, Y., Yoshizawa, H., Akiba, H., Mittler, R. S., Gejyo, F., Okumura, K., Yagita, H., and Smyth, M. J. (2006) Eradication of established tumours in mice by a combination antibody-based therapy. Nat. Med. 12, 693-698.

Vidarsson G, Dekkers G, Rispens T. IgG subclasses and allotypes: from structure to effector functions. Front Immunol. 2014 Oct. 20; 5:520. doi:10.3389/fimmu.2014.00520. Review. PubMed PMID: 25368619; PubMed Central PMCID: PMC4202688.

Vinay, D. S. and Kwon, B. S. (2012) Immunotherapy of cancer with 4-1BB. Mol. Cancer Ther. 11, 1062-1070.

Wang W, Erbe A K, Hank J A, Morris Z S, Sondel P M. NK Cell-Mediated Antibody-Dependent Cellular Cytotoxicity in Cancer Immunotherapy. Front Immunol. 2015 Jul. 27; 6:368. doi: 10.3389/fimmu.2015.00368. Review. PubMed PMID: 26284063; PubMed Central PMCID: PMC4515552.

Wei, H., Zhao, L., Li, W., Fan, K., Qian, W., Hou, S., Wang, H., Dai, M., Hellstrom, I., Hellstrom, K. E., and Guo, Y. (2013) Combinatorial PD-1 blockade and CD137 activation has therapeutic efficacy in murine cancer models and synergizes with cisplatin. PLoS. ONE. 8, e84927.

Westwood, J. A., Darcy, P. K., Guru, P. M., Sharkey, J., Pegram, H. J., Amos, S. M., Smyth, M. J., and Kershaw, M. H. (2010) Three agonist antibodies in combination with high-dose IL-2 eradicate orthotopic kidney cancer in mice. J. Transl. Med. 8, 42.

Westwood, J. A., Matthews, G. M., Shortt, J., Faulkner, D., Pegram, H. J., Duong, C. P., Chesi, M., Bergsagel, P. L., Sharp, L. L., Huhn, R. D., Darcy, P. K., Johnstone, R. W., and Kershaw, M. H. (2014a) Combination anti-CD137 and anti-CD40 antibody therapy in murine myc-driven hematological cancers. Leuk. Res. 38, 948-954.

White A L, Chan H T, French R R, Willoughby J, Mockridge C I, Roghanian A, Penfold C A, Booth S G, Dodhy A, Polak M E, Potter E A, Ardern-Jones M R, Verbeek J S, Johnson P W, Al-Shamkhani A, Cragg M S, Beers S A, Glennie M J. Conformation of the human immunoglobulin G2 hinge imparts superagonistic properties to immunostimulatory anticancer antibodies. Cancer Cell. 2015 Jan. 12; 27(1):138-48. doi:10.1016/j.ccell.2014.11.001. PubMed PMID: 25500122; PubMed Central PMCID: PMC4297290.

Westwood, J. A., Potdevin Hunnam, T. C., Pegram, H. J., Hicks, R. J., Darcy, P. K., and Kershaw, M. H. (2014b) Routes of delivery for CpG and anti-CD137 for the treatment of orthotopic kidney tumours in mice. PLoS. ONE. 9, e95847.

Wilcox, R. A., Flies, D. B., Zhu, G., Johnson, A. J., Tamada, K., Chapoval, A. I., Strome, S. E., Pease, L. R., and Chen, L. (2002) Provision of antigen and CD137 signaling breaks immunological ignorance, promoting regression of poorly immunogenic tumours. J Clin Invest 109, 651-659.

Wilson, N. S., Yang, B., Yang, A., Loeser, S., Marsters, S., Lawrence, D., Li, Y., Pitti, R., Totpal, K., Yee, S., Ross, S., Vernes, J. M., Lu, Y., Adams, C., Offringa, R., Kelley, B., Hymowitz, S., Daniel, D., Meng, G., and Ashkenazi, A. (2011b) An Fcgamma receptor-dependent mechanism drives antibody-mediated target-receptor signaling in cancer cells. Cancer Cell 19, 101-113.

Wyzgol, A., Muller, N., Fick, A., Munkel, S., Grigoleit, G. U., Pfizenmaier, K., and Wajant, H. (2009) Trimer stabilization, oligomerization, and antibody-mediated cell surface immobilization improve the activity of soluble trimers of CD27L, CD40L, 41BBL, and glucocorticoid-induced TNF receptor ligand. J Immunol 183, 1851-1861.

Zhang, N., Sadun, R. E., Arias, R. S., Flanagan, M. L., Sachsman, S. M., Nien, Y. C., Khawli, L. A., Hu, P., and Epstein, A. L. (2007) Targeted and untargeted CD137L fusion proteins for the immunotherapy of experimental solid tumours. Clin. Cancer Res. 13, 2758-2767.

Zhang B, Wang Z, Wu L et al. Circulating and tumor-infiltrating myeloid-derived suppressor cells in patients with colorectal carcinoma. PLoS One. 2013; 8(2):e57114

The invention claimed is:

1. An antibody or an antigen-binding fragment thereof with binding specificity for domain 2 of human CD137 wherein the antibody or antigen-binding fragment is a CD137 agonist and comprises a heavy chain variable region and a light chain variable region comprising the amino acid sequences of SEQ ID NO: 19 and SEQ ID NO: 20.

2. The antibody or antigen-binding fragment thereof according to claim 1 wherein the antibody or antigen-binding fragment exhibits one or more of the following properties:
   a) the ability to stimulate CD137 and activate T cells and other immune cells via a cross-linking dependent mechanism; and/or
   b) cross-reactivity with cyano-CD137 antibodies.

3. The antibody or antigen-binding fragment thereof according to claim 1 wherein the antibody or antigen binding fragment is capable of binding an Fc receptor.

4. The antibody or antigen-binding fragment thereof according to claim 1 wherein the ability of the antibody to activate T cells is dependent upon binding to both CD137 and Fc receptors.

5. The antibody or antigen-binding fragment thereof according to claim 1 wherein the antibody or antigen-binding fragment is incapable of inducing the following upon binding to cells expressing CD137:
   a) antibody-dependent cellular cytotoxicity (ADCC);
   b) antibody-dependent cellular phagocytosis (ADCP); and/or
   c) complement-dependent cytotoxicity (CDC).

6. The antibody or antigen-binding fragment thereof according to claim 1 wherein the antibody or antigen-binding fragment is capable of inducing tumour immunity.

7. The antibody or antigen-binding fragment thereof according to claim 1 comprising an intact antibody.

8. The antibody or antigen-binding fragment thereof according to claim 1 comprising an antigen-binding fragment selected from the group consisting of Fv fragments and Fab-like fragments.

9. The antibody or antigen-binding fragment according to claim 1 wherein the antibody or antigen-binding fragment thereof is human or humanised.

10. The antibody or antigen-binding fragment thereof according to claim 1 comprising a heavy chain constant region, or part thereof.

11. The antibody or antigen-binding fragment thereof according to claim 10 wherein the heavy chain constant region comprises an amino acid sequence selected from the group consisting of SEQ ID NO: 12, 13, 14 and 15.

12. The antibody or antigen-binding fragment thereof according to claim 1 comprising a light chain constant region, or part thereof.

13. The antibody or antigen-binding fragment thereof according to claim 12 wherein the light chain constant region comprises an amino acid sequence of SEQ ID NO: 16.

14. The antibody or antigen-binding fragment thereof according to claim 1 comprising an Fc region.

15. The antibody or antigen-binding fragment thereof according to claim 1 comprising a heavy chain comprising a variable region of SEQ ID NO: 19 together with a constant region of SEQ ID NO: 13; and a light chain comprising a variable region of SEQ ID NO: 20 together with a constant region of SEQ ID NO: 16.

16. The antibody or antigen-binding fragment thereof according to claim 1 wherein the antibody is an intact IgG4 molecule comprising
   two heavy chains having an amino acid sequence of SEQ ID NO: 29 and two light chains having an amino acid sequence of SEQ ID NO: 30.

17. A pharmaceutical composition comprising an effective amount of an antibody or antigen-binding fragment thereof according to claim 1 and a pharmaceutically-acceptable diluent, carrier or excipient.

* * * * *

SEQUENCE LISTING

```
<160> NUMBER OF SEQ ID NOS: 30

<210> SEQ ID NO 1
<211> LENGTH: 118
<212> TYPE: PRT
<213> ORGANISM: Artificial Sequence
<220> FEATURE:
<223> OTHER INFORMATION: 1630/1631 heavy chain variable region

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Tyr Ser
            20                  25                  30

Tyr Met Ser Trp Val Arg Gln Ala Pro Gly Lys Gly Leu Glu Trp Val
        35                  40                  45
```

```
Ser Ser Ile Gly Ser Gly Ser Ser Tyr Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Tyr Ser Pro Gly Ile Asp Tyr Trp Gly Gln Gly Thr
            100                 105                 110

Leu Val Thr Val Ser Ser
            115

<210> SEQ ID NO 2
<211> LENGTH: 108
<212> TYPE: PRT
<213> ORGANISM: Artificial Sequence
<220> FEATURE:
<223> OTHER INFORMATION: 1630/1631 light chain variable region

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Thr Trp Val Pro
                 85                  90                  95

Phe Thr Phe Gly Gln Gly Thr Lys Leu Glu Ile Lys
            100                 105

<210> SEQ ID NO 3
<211> LENGTH: 8
<212> TYPE: PRT
<213> ORGANISM: Artificial Sequence
<220> FEATURE:
<223> OTHER INFORMATION: Heavy chain variable region CDR

<400> SEQUENCE: 3

Gly Phe Thr Phe Gly Tyr Ser Tyr
 1               5

<210> SEQ ID NO 4
<211> LENGTH: 8
<212> TYPE: PRT
<213> ORGANISM: Artificial Sequence
<220> FEATURE:
<223> OTHER INFORMATION: Heavy chain variable region CDR

<400> SEQUENCE: 4

Ile Gly Ser Gly Ser Ser Tyr Thr
 1               5

<210> SEQ ID NO 5
<211> LENGTH: 11
<212> TYPE: PRT
<213> ORGANISM: Artificial Sequence
<220> FEATURE:
<223> OTHER INFORMATION: Heavy chain variable region CDR
```

<400> SEQUENCE: 5

Ala Arg Val Tyr Ser Ser Pro Gly Ile Asp Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Light chain variable region CDR

<400> SEQUENCE: 6

Gln Ser Ile Ser Ser Tyr
1               5

<210> SEQ ID NO 7

<400> SEQUENCE: 7

000

<210> SEQ ID NO 8
<211> LENGTH: 10
<212> TYPE: PRT
<213> ORGANISM: Artificial Sequence
<220> FEATURE:
<223> OTHER INFORMATION: Light chain variable region CDR

<400> SEQUENCE: 8

Gln Gln Tyr Tyr Thr Trp Val Pro Phe Thr
1               5                   10

<210> SEQ ID NO 9
<211> LENGTH: 354
<212> TYPE: DNA
<213> ORGANISM: Artificial Sequence
<220> FEATURE:
<223> OTHER INFORMATION: 1630 VH

<400> SEQUENCE: 9
gaggtgcagc tgttggagag cggggggaggc ttggtacagc ctggggggtc cctgcgcctc      60
tcctgtgcag ccagcggatt cacctttggt tactcttaca tgtcttgggt ccgccaggct     120
ccagggaagg ggctggagtg gtctcatct attggttctg gttcttctta cacatactat      180
gcagactccg tgaagggccg gttcaccatc tcccgtgaca attccaagaa cacgctgtat     240
ctgcaaatga acagcctgcg tgccgaggac acggctgtat attattgtgc gcgcgtttac     300
tcttctccgg gtattgacta ttggggccag ggaaccctgg tcaccgtctc ctca           354

<210> SEQ ID NO 10
<211> LENGTH: 324
<212> TYPE: DNA
<213> ORGANISM: Artificial Sequence
<220> FEATURE:
<223> OTHER INFORMATION: 1631 VL

<400> SEQUENCE: 10
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240

-continued

```
gaagattttg caacttatta ctgtcaacag tactacactt gggttccgtt cactttggc      300 cagggggacca agctggagat caaa                                           324
```

<210> SEQ ID NO 11
<211> LENGTH: 255
<212> TYPE: PRT
<213> ORGANISM: Homo sapiens

<400> SEQUENCE: 11

```
Met Gly Asn Ser Cys Tyr Asn Ile Val Ala Thr Leu Leu Leu Val Leu
1               5                  10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255
```

<210> SEQ ID NO 12
<211> LENGTH: 330
<212> TYPE: PRT
<213> ORGANISM: Homo sapiens

<400> SEQUENCE: 12

```
Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 327
<212> TYPE: PRT
<213> ORGANISM: Artificial Sequence
<220> FEATURE:
<223> OTHER INFORMATION: Modified IgG4 constant region

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95
```

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 14
<211> LENGTH: 327
<212> TYPE: PRT
<213> ORGANISM: Artificial Sequence
<220> FEATURE:
<223> OTHER INFORMATION: Modified IgG4 constant region

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

```
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn Arg Tyr Thr Gln Lys Ser
305                 310                 315                 320

Leu Ser Leu Ser Leu Gly Lys
                325

<210> SEQ ID NO 15
<211> LENGTH: 327
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
```

```
                        165                 170                 175
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 16
<211> LENGTH: 107
<212> TYPE: PRT
<213> ORGANISM: Homo sapiens

<400> SEQUENCE: 16

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 17
<211> LENGTH: 445
<212> TYPE: PRT
<213> ORGANISM: Artificial Sequence
<220> FEATURE:
<223> OTHER INFORMATION: 1630/1631- Full sequence Heavy chain

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Tyr Ser
            20                  25                  30

Tyr Met Ser Trp Val Arg Gln Ala Pro Gly Lys Gly Leu Glu Trp Val
        35                  40                  45
```

Ser Ser Ile Gly Ser Gly Ser Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Tyr Ser Ser Pro Gly Ile Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 18
<211> LENGTH: 215

```
<212> TYPE: PRT
<213> ORGANISM: Artificial Sequence
<220> FEATURE:
<223> OTHER INFORMATION: 1630/1631 - Full sequence Light chain

<400> SEQUENCE: 18
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Trp Val Pro
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

```
<210> SEQ ID NO 19
<211> LENGTH: 118
<212> TYPE: PRT
<213> ORGANISM: Artificial Sequence
<220> FEATURE:
<223> OTHER INFORMATION: 2674/2675 heavy chain variable region

<400> SEQUENCE: 19
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Phe Gly Tyr Ser
            20                  25                  30

Tyr Met Ser Trp Val Arg Gln Ala Pro Gly Lys Gly Leu Glu Trp Val
        35                  40                  45

Ser Ser Ile Gly Ser Thr Ser Ser His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Ser Ser Pro Gly Ile Asp Tyr Trp Gly Gln Gly Thr
            100                 105                 110

Leu Val Thr Val Ser Ser
        115

<210> SEQ ID NO 20
<211> LENGTH: 108
<212> TYPE: PRT
<213> ORGANISM: Artificial Sequence
<220> FEATURE:
<223> OTHER INFORMATION: 2674/2675 light chain variable region

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Thr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Trp Val Pro
                85                  90                  95

Phe Thr Phe Gly Gln Gly Thr Lys Leu Glu Ile Lys
            100                 105

<210> SEQ ID NO 21
<211> LENGTH: 8
<212> TYPE: PRT
<213> ORGANISM: Artificial Sequence
<220> FEATURE:
<223> OTHER INFORMATION: Heavy chain variable region CDR

<400> SEQUENCE: 21

Gly Phe Asn Phe Gly Tyr Ser Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: Heavy chain variable region CDR

<400> SEQUENCE: 22

Ile Gly Ser Thr Ser Ser His Thr
1               5

<210> SEQ ID NO 23
<211> LENGTH: 11
<212> TYPE: PRT
<213> ORGANISM: Artificial Sequence
<220> FEATURE:
<223> OTHER INFORMATION: Heavy chain variable region CDR

<400> SEQUENCE: 23

Ala Arg Val Tyr Ser Ser Pro Gly Ile Asp Tyr
1               5                   10

<210> SEQ ID NO 24
<211> LENGTH: 6
<212> TYPE: PRT
<213> ORGANISM: Artificial Sequence

```
<220> FEATURE:
<223> OTHER INFORMATION: Light chain variable region CDR

<400> SEQUENCE: 24

Gln Ser Ile Gly Ser Thr
1               5

<210> SEQ ID NO 25

<400> SEQUENCE: 25

000

<210> SEQ ID NO 26
<211> LENGTH: 10
<212> TYPE: PRT
<213> ORGANISM: Artificial Sequence
<220> FEATURE:
<223> OTHER INFORMATION: Light chain variable region CDR

<400> SEQUENCE: 26

Gln Gln Tyr Tyr Thr Trp Val Pro Phe Thr
1               5                   10

<210> SEQ ID NO 27
<211> LENGTH: 1335
<212> TYPE: DNA
<213> ORGANISM: Artificial Sequence
<220> FEATURE:
<223> OTHER INFORMATION: 2674, VH

<400> SEQUENCE: 27
gaggtgcagt tgttggaatc tggcggagga ttggtgcagc ctggcggatc tctgagactg     60
tcttgtgccg cctctggctt caacttcggc tactcctaca gtcctgggt ccgacaggct    120 cctggcaaag gactggaatg ggtgtcctcc atcggctcca ccagctctca cacctactac    180
gccgattccg tgaagggcag attcaccatc agccgggaca ctccaagaa cacccctgtac   240 ctgcagatga actccctgag agccgaggac accgccgtgt actactgtgc cagagtgtac    300
tcctctcctg gcatcgatta ttggggccag ggcacactgg tcaccgtgtc ctctgcttct    360
accaagggac cctctgtgtt ccctctggct ccttgctcca gatccacctc tgagtctacc    420
gctgctctgg gctgcctggt caaggattac tttcctgagc ctgtgaccgt gtcttggaac    480
tccggtgctc tgacatccgg cgtgcacaca tttccagctg tgctgcagtc ctccggcctg    540
tactctctgt cctctgtcgt gaccgtgcct tctagctctc tgggcaccaa gacctacacc    600
tgtaacgtgg accacaagcc ttccaacacc aaggtggaca gcgcgtgga atctaagtac    660 ggccctccat gtccaccatg tcctgctcca gaattcctcg gcggaccaag cgtgttcctg    720
tttcctccaa agcctaagga caccctgatg atctctcgga cccctgaagt gacctgcgtg    780
gtggtggatg tgtctcaaga ggacccagaa gtgcagttca attggtacgt ggacggcgtg    840
gaagtgcaca acgccaagac caagcctaga gaggaacagt tcaactccac ctacagagtg    900
gtgtccgtgc tgaccgtgct gcaccaggat tggctgaacg gcaaagagta caagtgcaag    960
gtgtccaaca aggcctgcc ttccagcatc gaaaagacca ctccaaggc taagggccag    1020 cctcgggaac ctcaggttta cacctgcct ccaagccaag aggaaatgac caagaaccag    1080
gtgtccctga cctgcctcgt gaagggatc taccttccg atatcgccgt ggaatgggag    1140
tctaacggcc agccagagaa caactacaag acaaccccctc ctgtgctgga ctccgacggc    1200 tcttcttcc tgtattctcg cctgaccgtg gacaagtctc ggtggcaaga gggcaacgtg    1260
```

```
ttctcctgct ctgtgatgca cgaggccctg cacaaccact acacacagaa gtccctgtct    1320
ctgtccctgg gcaag                                                     1335
```

<210> SEQ ID NO 28
<211> LENGTH: 645
<212> TYPE: DNA
<213> ORGANISM: Artificial Sequence
<220> FEATURE:
<223> OTHER INFORMATION: 2675, VL

<400> SEQUENCE: 28

```
gacatccaga tgacccagtc tccatcctct ctgtctgcct ctgtgggcga cagagtgacc      60
atcacctgtc gggcttctca gtccatcggc agcaccctga actggtatca gcagaagcct     120
ggcaaggccc ctaagctgct gatctatggc gctagctctc tgcagtctgg cgtgccctct     180
agattttccg gctctggctc tggcaccgac ttcaccctga caatcagttc cctgcagcct     240
gaggacttcg ccacctacta ctgccagcag tactacaccc tgggtgccct tacctttggc     300
cagggcacca agctggaaat caagagaacc gtggccgctc cttccgtgtt catcttccca     360
ccatctgacg agcagctgaa gtccggcaca gcttctgtcg tgtgcctgct gaacaacttc     420
taccctcggg aagccaaggt gcagtggaag gtggacaatg ccctgcagtc cggcaactcc     480
caagagtctg tgaccgagca ggactccaag gactctacct acagcctgtc ctccacactg     540
accctgtcta aggccgacta cgagaagcac aaggtgtacg cctgcgaagt gacccatcag     600
ggactgtcta gcccgtgac caagtccttc aacagaggcg agtgt                     645
```

<210> SEQ ID NO 29
<211> LENGTH: 445
<212> TYPE: PRT
<213> ORGANISM: Artificial Sequence
<220> FEATURE:
<223> OTHER INFORMATION: 2674/2675 - Full sequence heavy chain

<400> SEQUENCE: 29

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Phe Gly Tyr Ser
            20                  25                  30

Tyr Met Ser Trp Val Arg Gln Ala Pro Gly Lys Gly Leu Glu Trp Val
        35                  40                  45

Ser Ser Ile Gly Ser Thr Ser His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Ser Ser Pro Gly Ile Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 30
<211> LENGTH: 215
<212> TYPE: PRT
<213> ORGANISM: Artificial Sequence
<220> FEATURE:
<223> OTHER INFORMATION: 2674/2675 - Full sequence light chain

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Thr
            20                  25                  30

Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Trp Val Pro
            85                  90                  95
```

```
Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215
```